United States Patent
Narita et al.

(10) Patent No.: US 9,055,866 B2
(45) Date of Patent: Jun. 16, 2015

(54) INTERNAL OBSERVATION DEVICE FOR OBJECT HAVING LIGHT SCATTERING PROPERTIES, INTERNAL BODY OBSERVATION DEVICE, ENDOSCOPE FOR INTERNAL OBSERVATION AND INTERNAL OBSERVATION METHOD

(75) Inventors: Toshiharu Narita, Hachioji (JP); Ken Fujinuma, Machida (JP); Ryosuke Ito, Kunitachi (JP); Kenji Taira, Kodaira (JP); Hideyuki Takaoka, Fuchu (JP); Shinichi Takimoto, Hachioji (JP); Hiroyuki Nishida, Sagamihara (JP); Hiroya Fukuyama, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 344 days.

(21) Appl. No.: 12/978,932

(22) Filed: Dec. 27, 2010

(65) Prior Publication Data
US 2011/0263955 A1    Oct. 27, 2011

Related U.S. Application Data

(63) Continuation-in-part of application No. PCT/JP2009/055486, filed on Mar. 19, 2009.

(30) Foreign Application Priority Data

| Jun. 27, 2008 | (JP) | 2008-169459 |
| Jun. 27, 2008 | (JP) | 2008-169460 |
| Sep. 1, 2008 | (JP) | 2008-223957 |
| Sep. 1, 2008 | (JP) | 2008-223958 |
| Sep. 1, 2008 | (JP) | 2008-223959 |
| Sep. 1, 2008 | (JP) | 2008-223960 |
| Dec. 28, 2009 | (JP) | 2009-297178 |

(51) Int. Cl.
A61B 5/00 (2006.01)
A61B 1/00 (2006.01)
(Continued)

(52) U.S. Cl.
CPC ............ *A61B 5/0064* (2013.01); *A61B 5/0062* (2013.01); *A61B 1/00096* (2013.01);
(Continued)

(58) Field of Classification Search
USPC .................................. 600/473, 475, 476, 477
See application file for complete search history.

(56) References Cited

U.S. PATENT DOCUMENTS 5,137,355 A * 8/1992 Barbour et al. ............... 356/342
7,456,874 B1 * 11/2008 Ono ............................. 348/239
(Continued)

FOREIGN PATENT DOCUMENTS

| JP | 2000-105191 | 4/2000 |
| JP | 2001-324444 | 11/2001 |

(Continued)

OTHER PUBLICATIONS

International Search Report of PCT/JP2010/073583 dated Apr. 12, 2011.

*Primary Examiner* — Long V Le
*Assistant Examiner* — Michael Kellogg
(74) *Attorney, Agent, or Firm* — Scully, Scott, Murphy & Presser, P.C.

(57) ABSTRACT

There is provided an inside observation apparatus of an endoscope and the like which can perform an inside observation for irradiating an illumination light to a minute area of a surface of an object (for example, a living tissue) having a light scattering property and detecting a back-scattered light of the illumination light, can increase a detected light amount by a simply and low cost configuration by making an area of a detection region larger than an illumination region, and can reduce a time necessary to detect an body (for example, a blood vessel) to be observed and detect a region deeper than a conventional region.

6 Claims, 32 Drawing Sheets

(51) Int. Cl.
*A61B 1/04* (2006.01)
*A61B 1/07* (2006.01)
*G01N 21/47* (2006.01)
*A61B 1/313* (2006.01)
*A61B 5/1455* (2006.01)

(52) U.S. Cl.
CPC ......... *A61B1/00165* (2013.01); *A61B 1/00172* (2013.01); *A61B 1/042* (2013.01); *A61B 1/07* (2013.01); *A61B 5/0073* (2013.01); *A61B 5/489* (2013.01); *G01N 21/4795* (2013.01); *A61B 5/4887* (2013.01); *A61B 1/0008* (2013.01); *A61B 1/3137* (2013.01); *A61B 5/1455* (2013.01)

(56) References Cited

U.S. PATENT DOCUMENTS

| | | | |
|---|---|---|---|
| 2004/0186382 A1* | 9/2004 | Modell et al. | 600/473 |
| 2005/0107708 A1* | 5/2005 | Wrobel et al. | 600/476 |
| 2006/0084948 A1* | 4/2006 | Rovati et al. | 606/4 |
| 2006/0155193 A1* | 7/2006 | Leonardi et al. | 600/473 |
| 2006/0184047 A1* | 8/2006 | Yamashita et al. | 600/476 |
| 2007/0038116 A1* | 2/2007 | Yamanaka et al. | 600/476 |
| 2007/0038118 A1* | 2/2007 | DePue et al. | 600/476 |

FOREIGN PATENT DOCUMENTS

| | | |
|---|---|---|
| JP | 2002-502654 | 1/2002 |
| JP | 2002-515277 | 5/2002 |
| JP | 2002-531846 | 9/2002 |
| JP | 2003-10189 | 1/2003 |
| JP | 2004-166827 A | 6/2004 |
| JP | 2004-528542 | 9/2004 |
| JP | 2005-538752 | 12/2005 |
| JP | 2006-200943 | 8/2006 |
| JP | 2007-20735 | 2/2007 |
| JP | 2007-330381 | 12/2007 |
| JP | 2008-510586 | 4/2008 |
| JP | 2009-153654 A | 7/2009 |
| WO | WO 2007/105495 A1 | 9/2007 |
| WO | 2009/157229 A1 | 12/2009 |

* cited by examiner

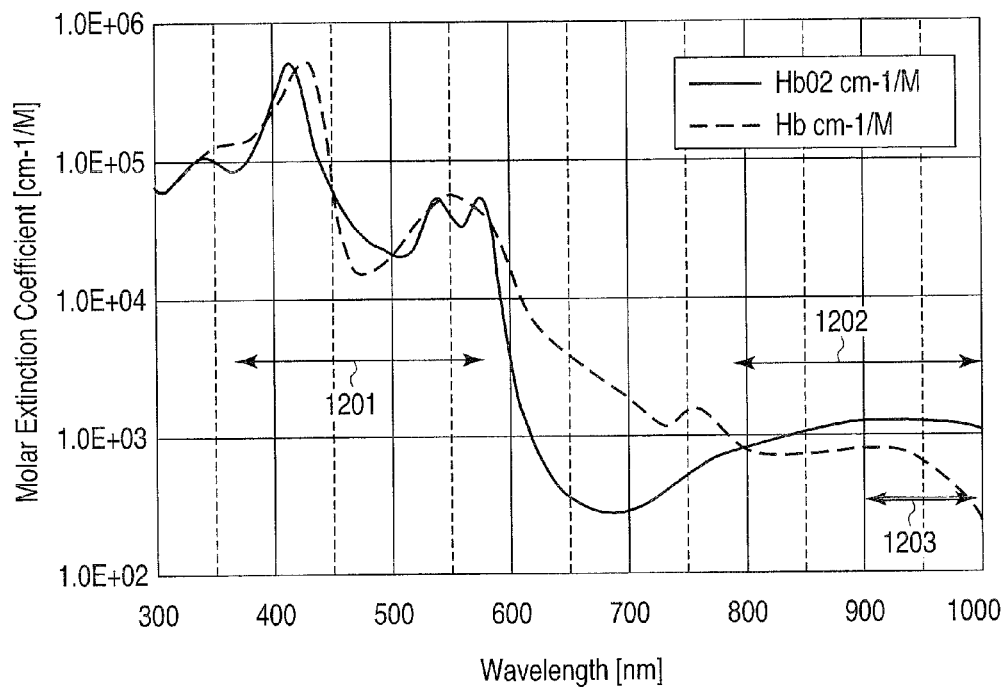
F I G. 12
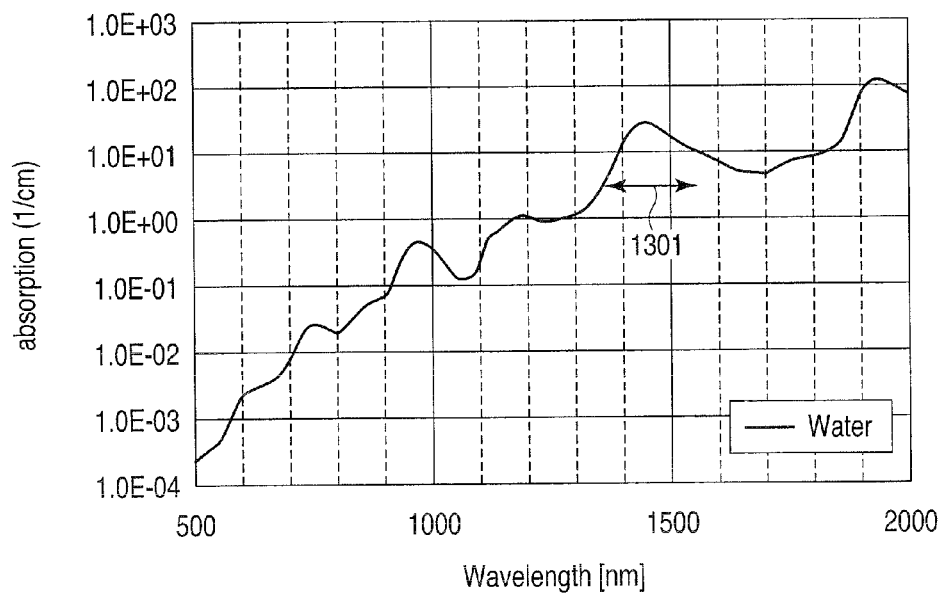
F I G. 13

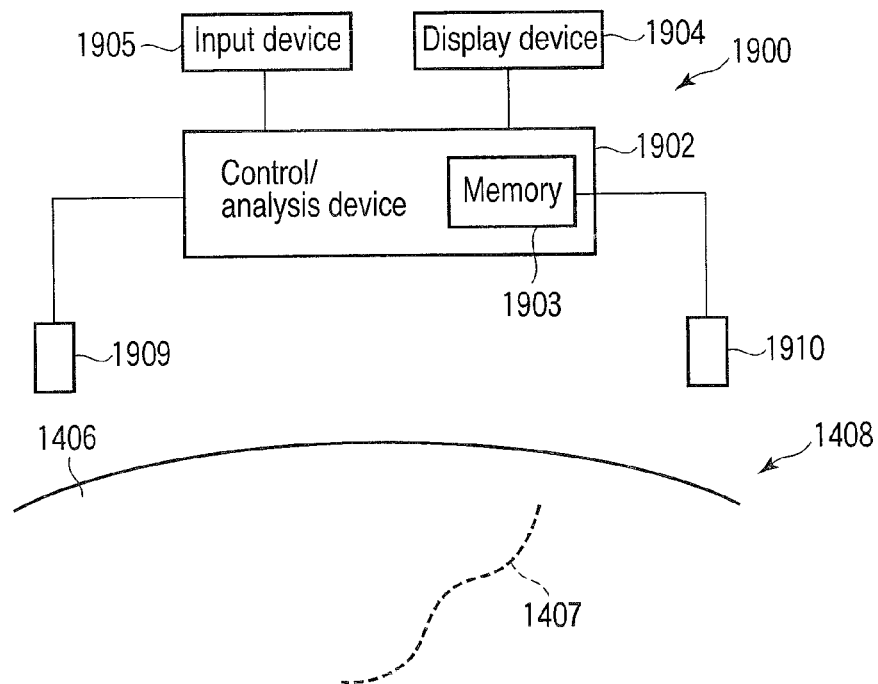
F I G. 19
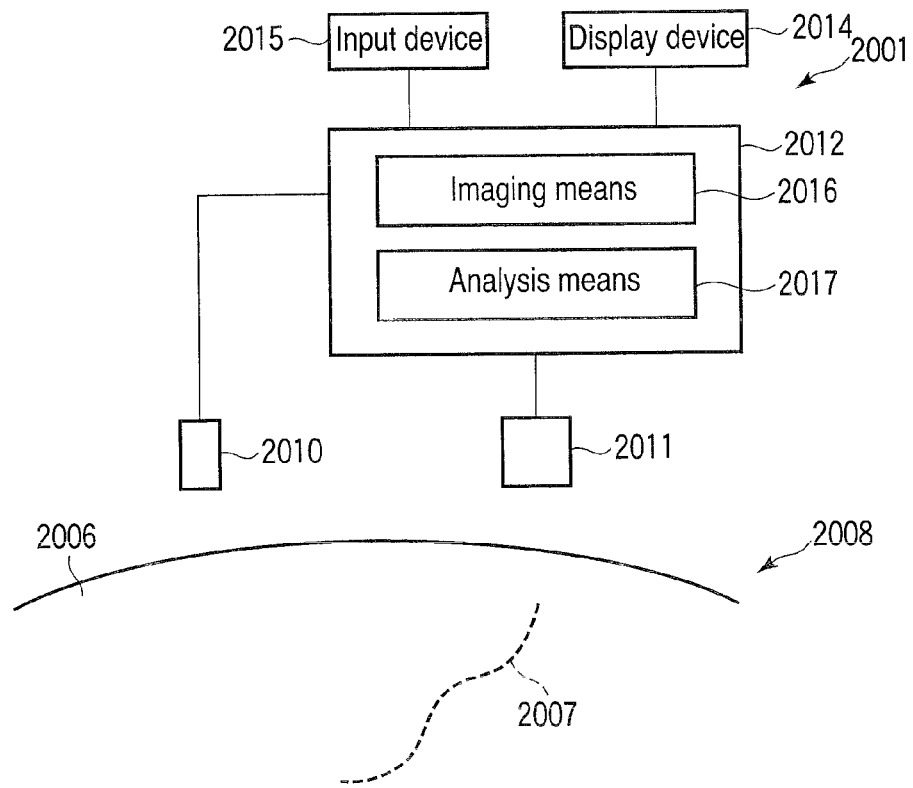
F I G. 20

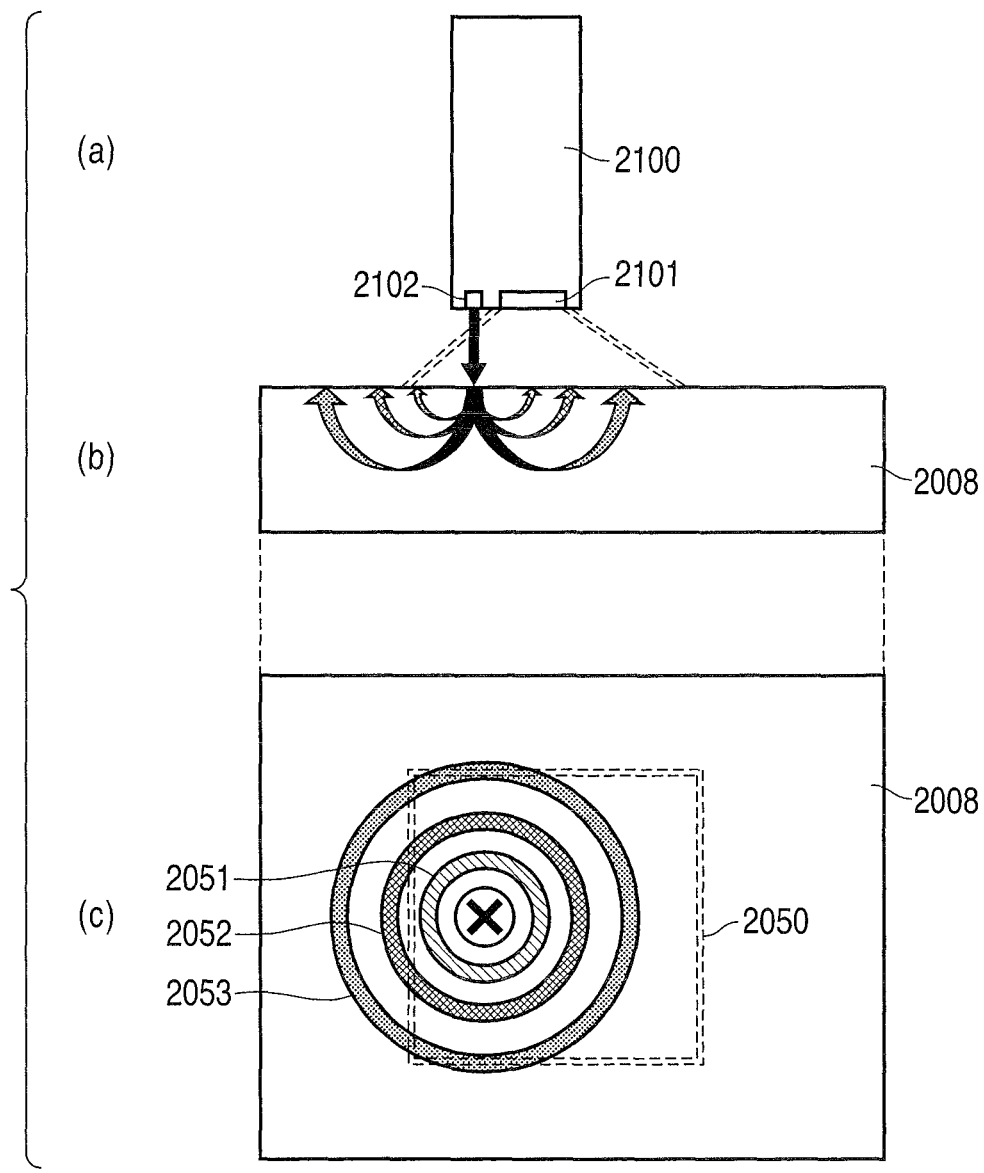
F I G. 21

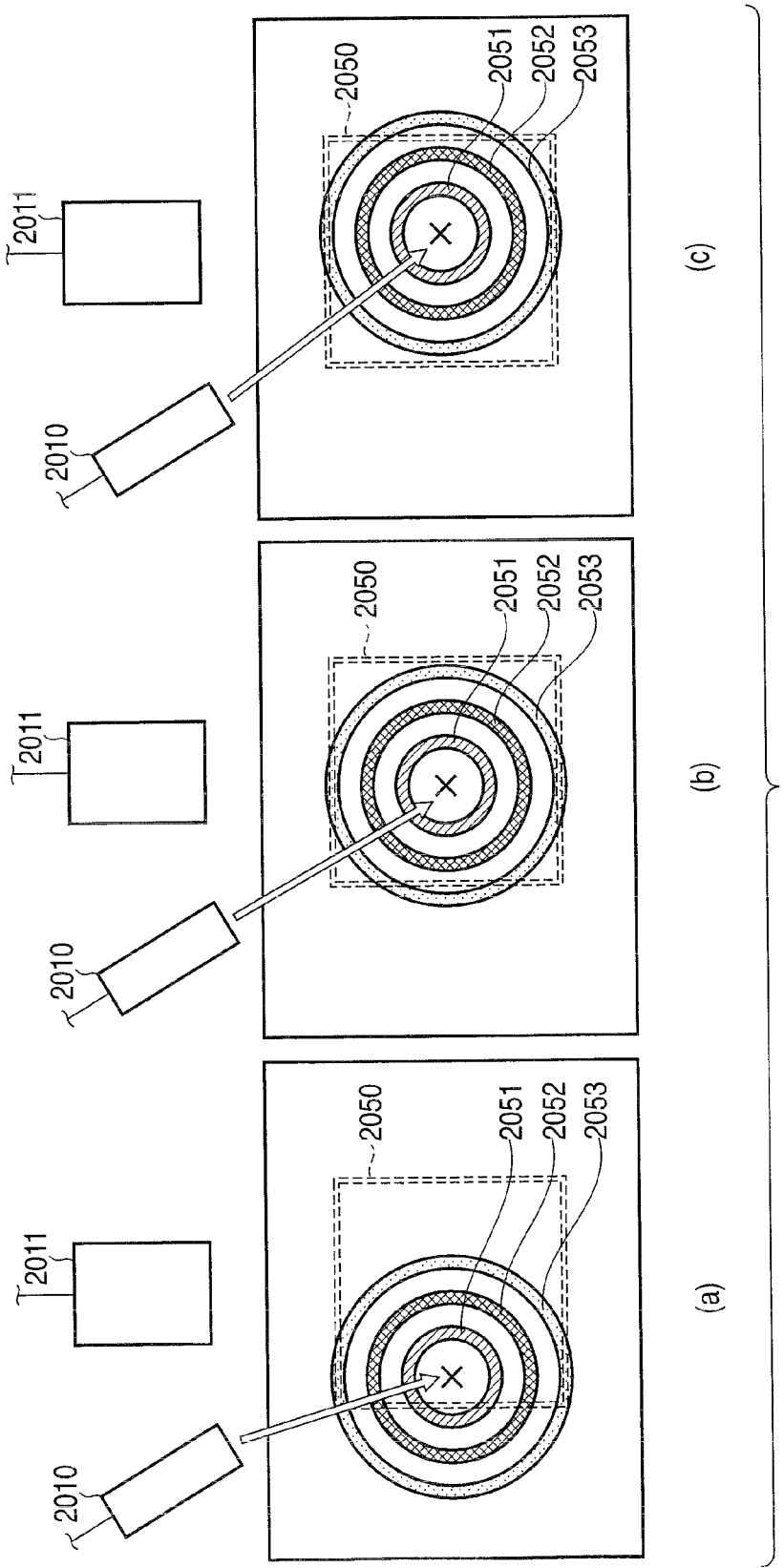
F I G. 22

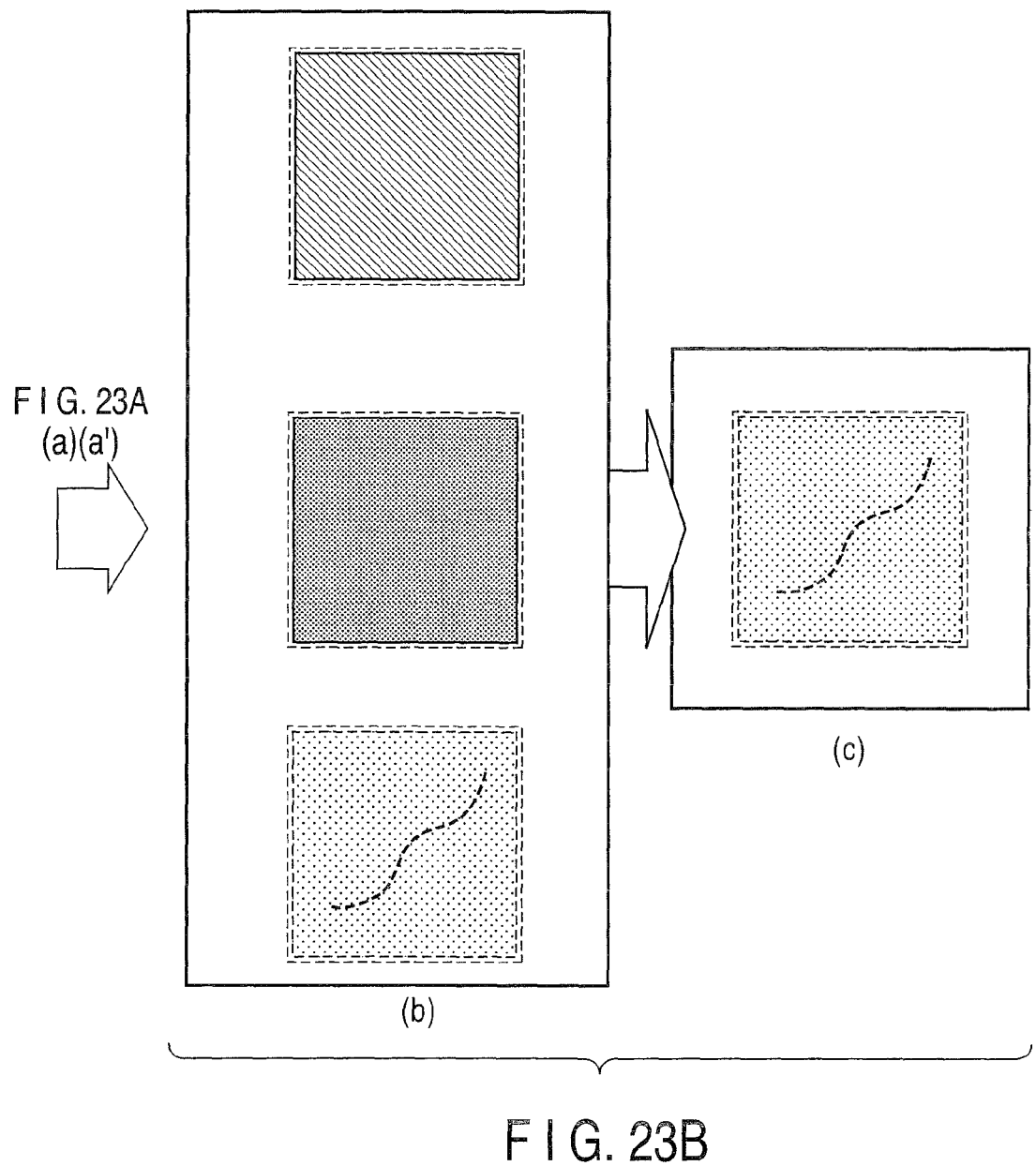

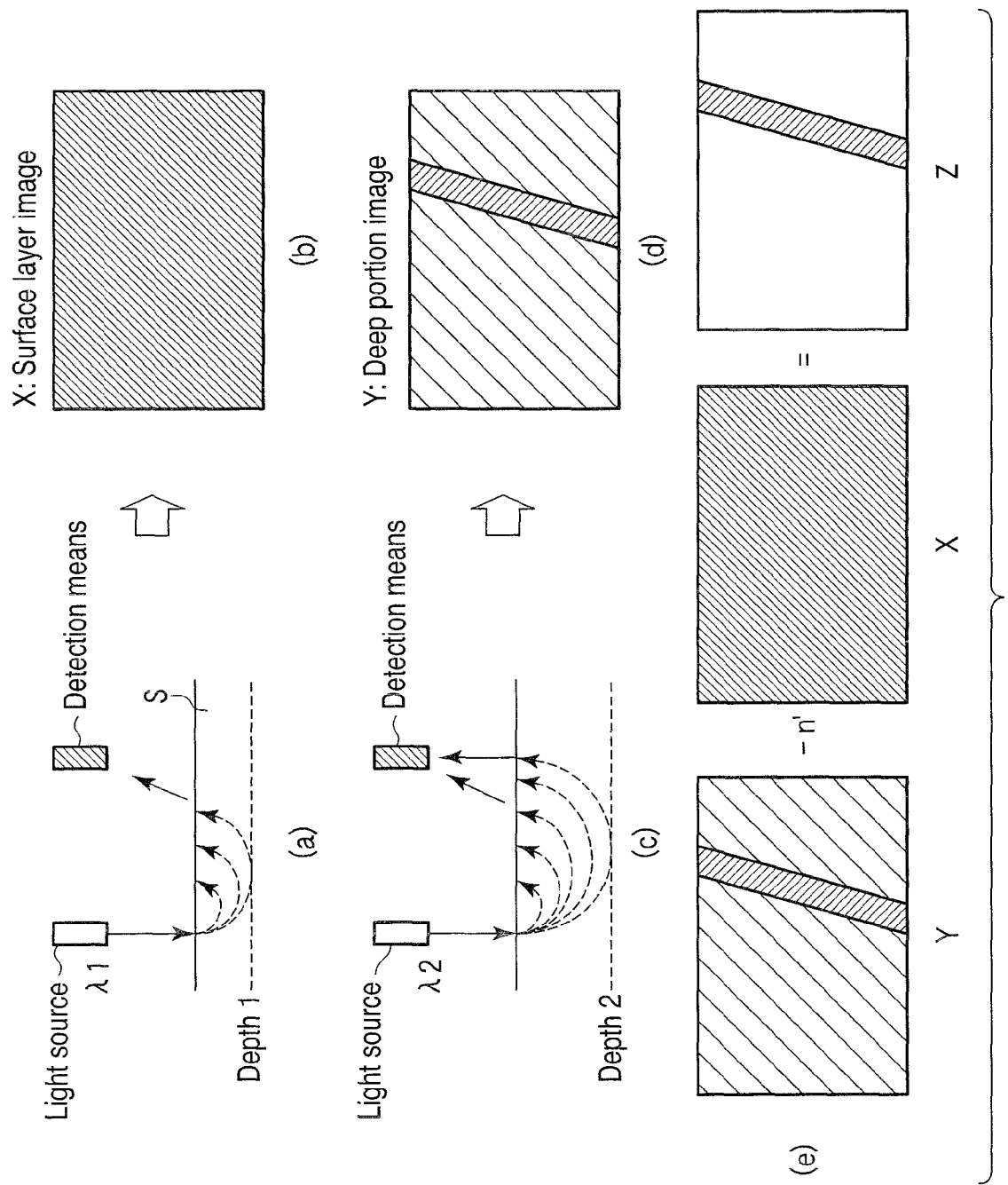
F I G. 25

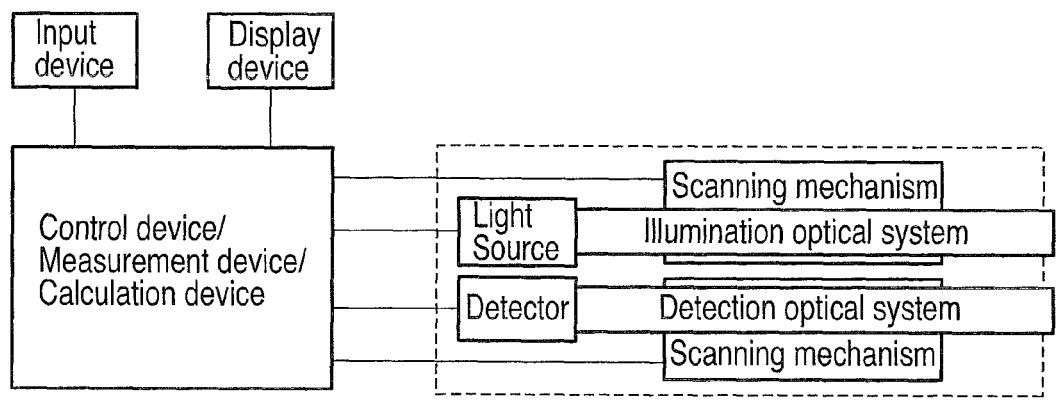
F I G. 27
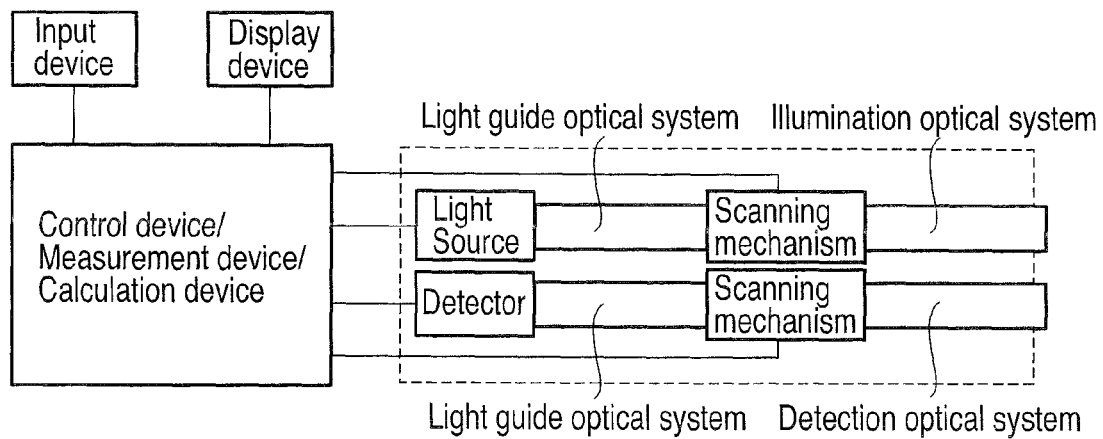
F I G. 28

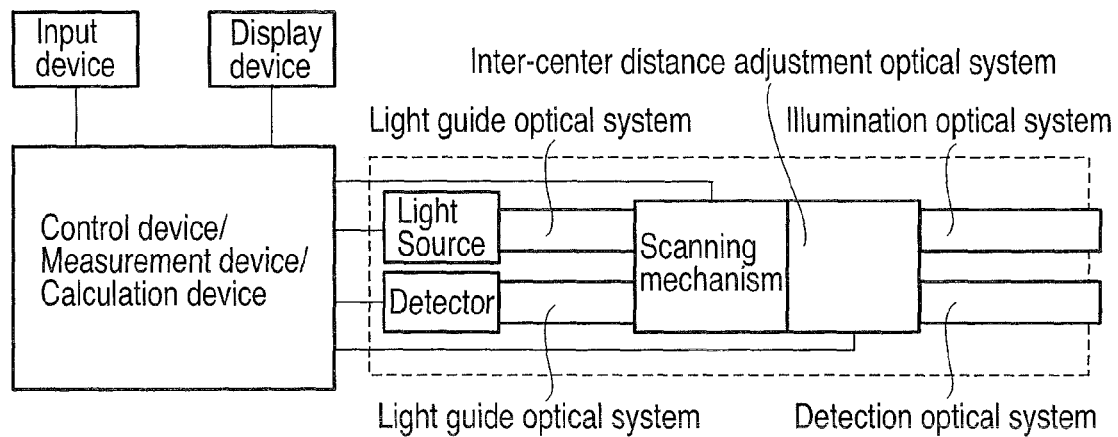
F I G. 29
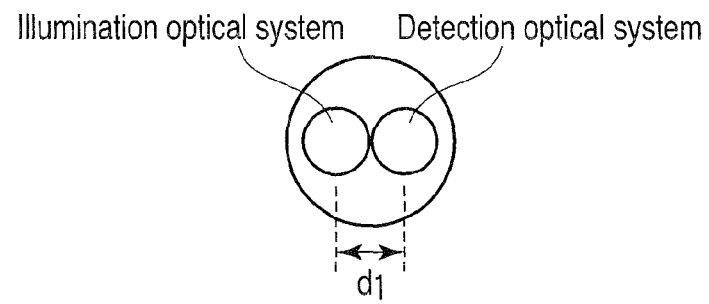
F I G. 30

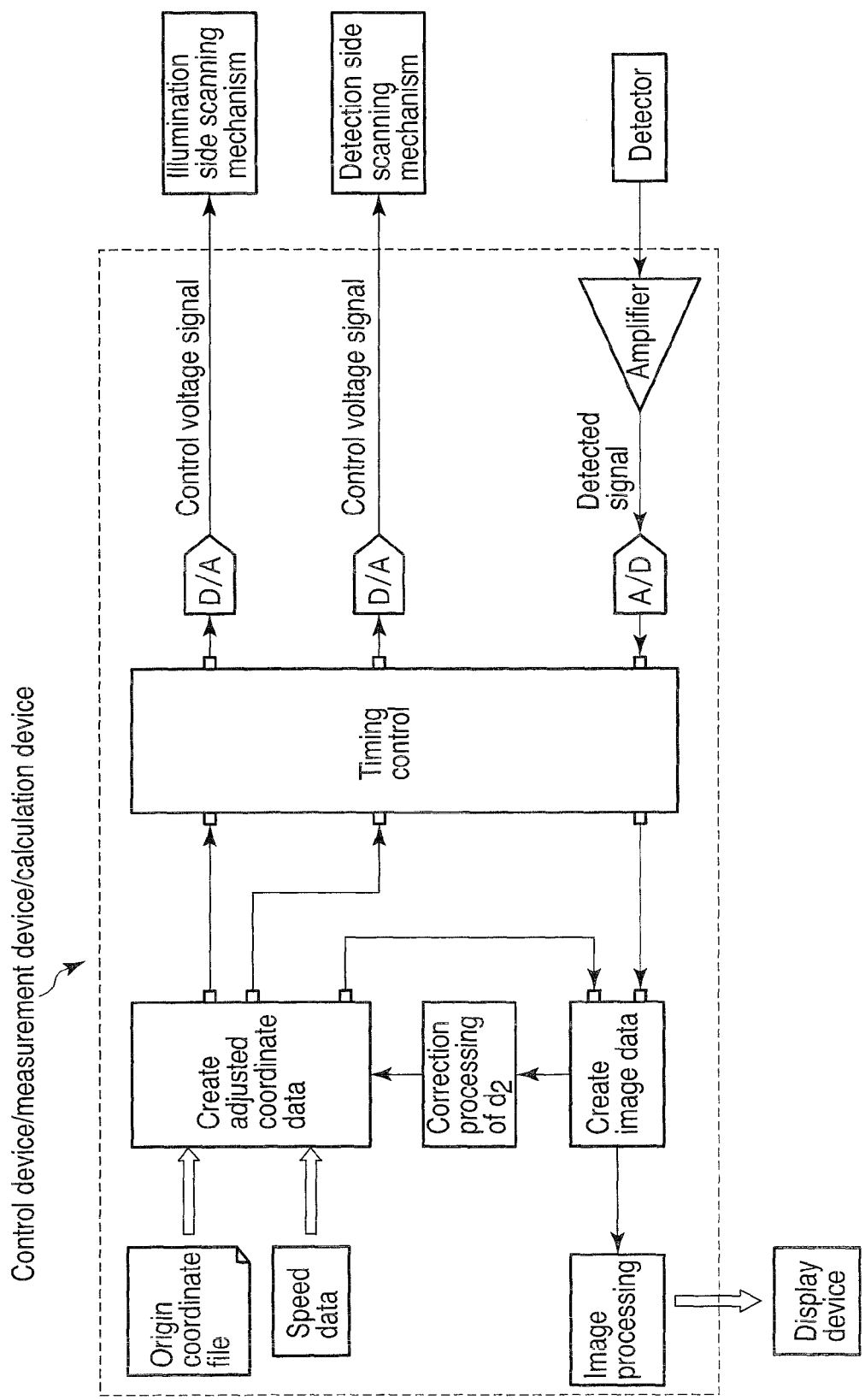
F I G. 41

INTERNAL OBSERVATION DEVICE FOR OBJECT HAVING LIGHT SCATTERING PROPERTIES, INTERNAL BODY OBSERVATION DEVICE, ENDOSCOPE FOR INTERNAL OBSERVATION AND INTERNAL OBSERVATION METHOD

CROSS-REFERENCE TO RELATED APPLICATIONS

This is a Continuation-in-Part Application of PCT application No. PCT/JP2009/055486, filed Mar. 19, 2009, which was published under PCT Article 21(2) in Japanese.

This application is based upon and claims the benefit of priority from the prior Japanese Patent Applications No. 2008-169459, filed Jun. 27, 2008, No. 2008-169460, filed Jun. 27, 2008, No. 2008-223957, filed Sep. 1, 2008, No. 2008-223958, filed Sep. 1, 2008, No. 2008-223959, filed Sep. 1, 2008, No. 2008-223960, filed Sep. 1, 2008, and No. 2009-297178, filed Dec. 28, 2009, the entire contents of all of which are incorporated herein by reference.

BACKGROUND OF THE INVENTION

1. Field of the Invention

The invention relates to an apparatus for and a method of observing an inside of a living body by measuring a back-scattered light generated by an object having a light scattering property, for example, a living body.

2. Description of the Related Art

Ordinarily, it is not easy to optically observe an inside of an object having a light scattering property. In many cases, there are only proposed various methodologies of observing an inside of a living body. As one of the methodologies, an observation using light has an advantage in that a specific object can be observed by selecting a wavelength of a light to be used. In the method, a light having a wavelength, which is absorbed by a specific object to be observed (for example, a heterogeneous portion), is irradiated to a living body and an intensity of a back-scattered light of the object is measured, thereby obtaining position information of a heterogeneous portion existing in an inside of the living body. The back-scattered light is a light which has passed through a deeper portion of a turbid media such as a living body and the like as the distance between an irradiation position and a measure position becomes longer.

Further, the method can obtain not only the position information of the heterogeneous portion but also can obtain depth information of the heterogeneous portion. Further, when the method collects the data of back-scattered lights having the same distances between irradiation positions and measure positions, the method can create a distribution image of the back-scattered lights (that is, two-dimensional data). Jpn. Pat. Appln. KOKAI Publication No. 2006-200943 discloses a living body light observation apparatus including a light irradiation device and a plurality of light detection devices. The light detection devices are disposed at positions which are gradually away from a position of one light irradiation device. Further, Jpn. Pat. Appln. KOKAI Publication No. 2006-200943 discloses a technology for reconfiguring a tomographic image of a living body (that is, three-dimensional data) based on a result of measurement.

Jpn. Pat. Appln. KOKAI Publication No. 2007-20735 discloses a living body light measurement apparatus including a light irradiation device and a plurality of light detection devices. The light detection devices are disposed on, for example, concentric circles at predetermined gaps from the light irradiation device.

BRIEF SUMMARY OF THE INVENTION

An object of the invention is to provide a method and apparatus capable of observing an inside of a living body better than a conventional method and apparatus.

In view of the above problems, the invention provides an apparatus for measuring the interior of turbid media (that is, a turbid media inside observation apparatus), which obtains information of an object to be measured (that is, an object to be observed) in an inside of a turbid media and a measurement method using the apparatus for measuring the interior of turbid media, wherein the apparatus for measuring the interior of turbid media comprises an illumination device (that is, a light irradiation device) configured to irradiate a light having optical characteristics, which are different in the object to be observed and in the turbid media, to the turbid media, a detection device configured to detect a back-scattered light of the light irradiated by the illumination device, and an analysis device configured to confirm whether or not the object to be measured exists in the data obtained by the detection device and to obtain position information including a depth of the object to be measured in the turbid media from distances to the positions where the irradiation position and the object to be measured are confirmed, and the illumination device and the detection device perform a measurement without contacting the turbid media.

According to modes of the invention, there are provided methods and apparatuses capable of observing an inside of a living body better than a conventional method and apparatus.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12 is a graph of a wavelength dependency of a molar extinction coefficient of hemoglobin;

FIG. 13 is a graph of a wavelength dependency of an absorption coefficient of water;

FIG. 19 is a block configuration view of an apparatus for measuring the interior of turbid media according to a fourth embodiment;

FIG. 20 is a block configuration view of an apparatus for measuring the interior of turbid media according to a fifth embodiment;

FIG. 21 is a schematic view of a hard mirror to which a turbid media inside observation apparatus according to a third aspect is applied and a conceptual view showing how a light is transmitted in an inside and on a surface of a turbid media;

FIG. 22 is a conceptual view showing how illumination is scanned;

FIG. 23B is a schematic view showing loci of an equi-depth region obtained by scanning an irradiation position;

FIG. 25 is a conceptual view showing a second method of noise removing methods;

FIG. 27 shows an inside observation apparatus as an example of a seventh embodiment;

FIG. 28 shows an inside observation apparatus as an example of an eighth embodiment;

FIG. 29 shows an inside observation apparatus as an example of a ninth embodiment;

FIG. 30 is a view schematically showing an example of an object to be picked up side distal end of the observation apparatus;

FIG. 41 is a block diagram showing an example of a configuration of a control unit.

DETAILED DESCRIPTION OF THE INVENTION

Figure 1:
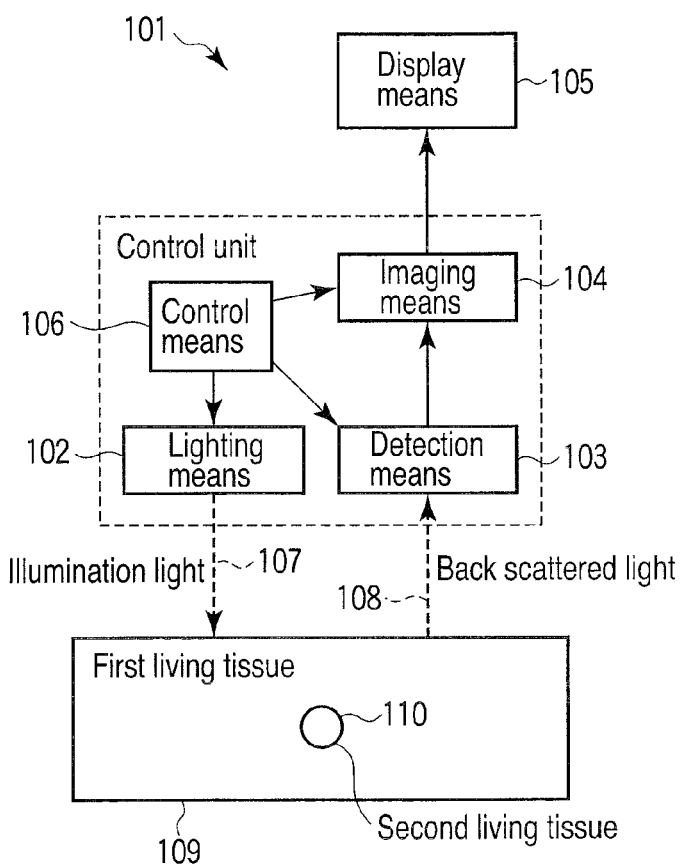
FIG. 1 is a block diagram showing a configuration of an apparatus for observing the interior of living body.

An apparatus for measuring the interior of turbid media of the invention will be explained below. In the invention, a turbid media means an arbitrary turbid media configured of a scattering medium, and a living body may be exemplified as an example of the turbid media. The apparatus for measuring the interior of turbid media of the invention measures an object to be measured which exists in a scattering medium in an inside of a turbid media. Although an object to be measured in the invention may be, for example, a blood vessel and the like, the object to be measured is not limited thereto. In the description, "an inside observation apparatus for an object having a light scattering property" means an apparatus for observing an inside of a turbid media acting as the object described above. Further, "the apparatus for measuring the interior of turbid media" and "an apparatus for observing the interior of living body" mean apparatuses which observe, in particular, an inside of a living body in objects having the light scattering property, and are synonymous with the apparatuses, and can be exchangeably used with the apparatuses. Further, "an inside observation endoscope" means, in particular, an apparatus having a mode of an endoscope in the observation apparatuses described above.

Embodiments of the invention will be explained below according to the drawings. Note that, in the following explanation, components having approximately the same functions and configurations are denoted by the same reference numerals, and a duplicate explanation will be made only when it is necessary.

<First Aspect>

An embodiment of the invention will be explained below as to an inside observation apparatus using a living tissue, which is an object to be observed having a light scattering property, as an example referring to the drawings.

FIG. 1 shows a block configuration view of the embodiment. As shown in the drawings, an observation apparatus 101 includes an illumination device (in the drawings, an lighting means) 102, a detection device (in the drawings, a detection means) 103, an imaging device (in the drawings, an imaging means) 104, a display device (in the drawings, a display means) 105, and a control device (in the drawings, a control means) 106 configured to control these devices.

The illumination device 102 irradiates a light 107 to a living tissue based on a control from the control device. The detection device 103 detects a back-scattered light 108 generated by the illumination light 107 and converts the back-scattered light 108 to an electric signal. The illumination and detection are performed to determine whether or not a second living tissue (an object to be observed having heterogeneous scattering characteristics in an inside of a living body) 110 exists in a first living tissue 109. For the purpose, the illumination light 107 uses a light including at least a wavelength having optical characteristics, which are different in the first living tissue 109 and in the second living tissue 110. The imaging device 104 creates a two-dimensional distribution of a light intensity detected by the detection device 103 as a shaded image and a color image and displays the image on the display device 105.

In the case where the second living tissue 110 existing in the first living tissue 109 is optically observed, it is necessary to observe the second living tissue 110 by making use of a light which enters into the living tissue. However, a living tissue is a medium configured of a countless number of cells, the organelle of the cells, and the like. Accordingly, the living tissue optically has a scattering property except some living tissues such as an eye ball and the like. Further, there is a light absorbed by the living tissue. Accordingly, an amount of a light, which enters into an inside of a living tissue and further returns backward, that is, an amount of the back-scattered light 108 is greatly attenuated, and greatly weakened as compared with a reflected light on a surface and a surface diffused light. As a method of detecting a weak light with a high S/N ratio, there is a method of increasing an exposure time and a method of using a highly sensitive detector. However, the former method has a problem in that an image pick-up time is increased and the latter method has a problem in that the detector is expensive.

Figure 2:
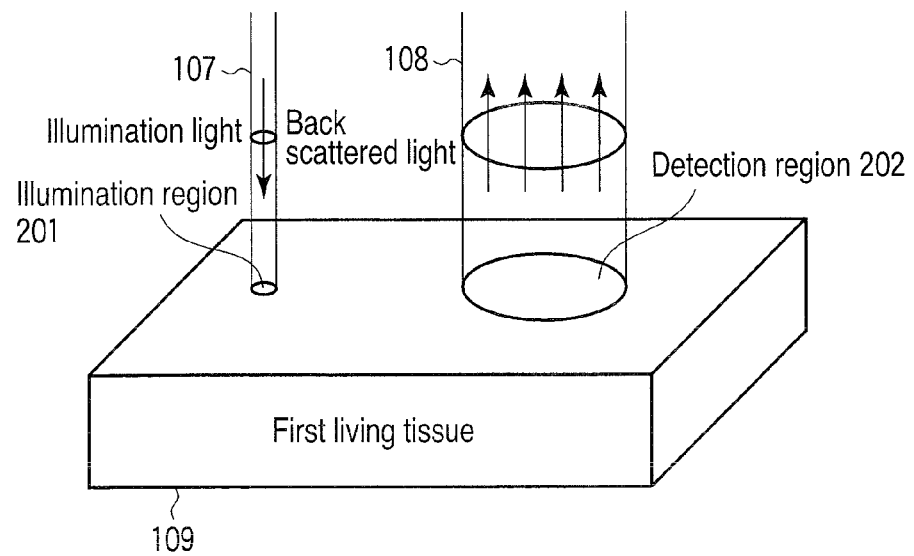
FIG. 2 is a schematic view showing a principle of an observation method of the invention.

FIG. 2 shows a schematic view of a detection region. An illumination region 201 shows a circular region when the illumination light 107 impinges on an surface of the first living tissue 109. A detection region 202 shows a circular region detected by the detection device 103 on the surface of the first living tissue 109. That is, only a light which outgoes from the detection region 202 in the back-scattered light 108 is detected. A shape of the illumination region 201 and the detection region 202 is not necessarily a circular shape. For example, the shape may be a square shape, a rectangular shape, a polygonal shape, a perfect circular shape, an oval shape, an arc-like block shape, and the like.

Here, a larger area of the detection region 202 can detect a larger amount of the back-scattered light 108 as well as can detect even the back-scattered light 108, which is very weakened, by increasing an S/N ratio. In an ordinary detection of scattered light, the detection region 202 having an area approximately as large as the illumination region 201 is used. However, in the mode, the S/N ratio is increased by a simple configuration of making the detection region 202 larger than the illumination region 201.

In the case where the second living tissue 110 existing in the first living tissue 109 is optically observed, the back-scattered light 108, which enters into the inside of the living tissue and further returns backward, is the very weak light as described above. Accordingly, even if the back-scattered light 108 is detected by increasing the S/N ratio as much as possible, since the back-scattered light 108 is buried in the signals of a reflected light and a diffused light on the surface, it is difficult to read a change of the back-scattered light 108.

Figure 3:
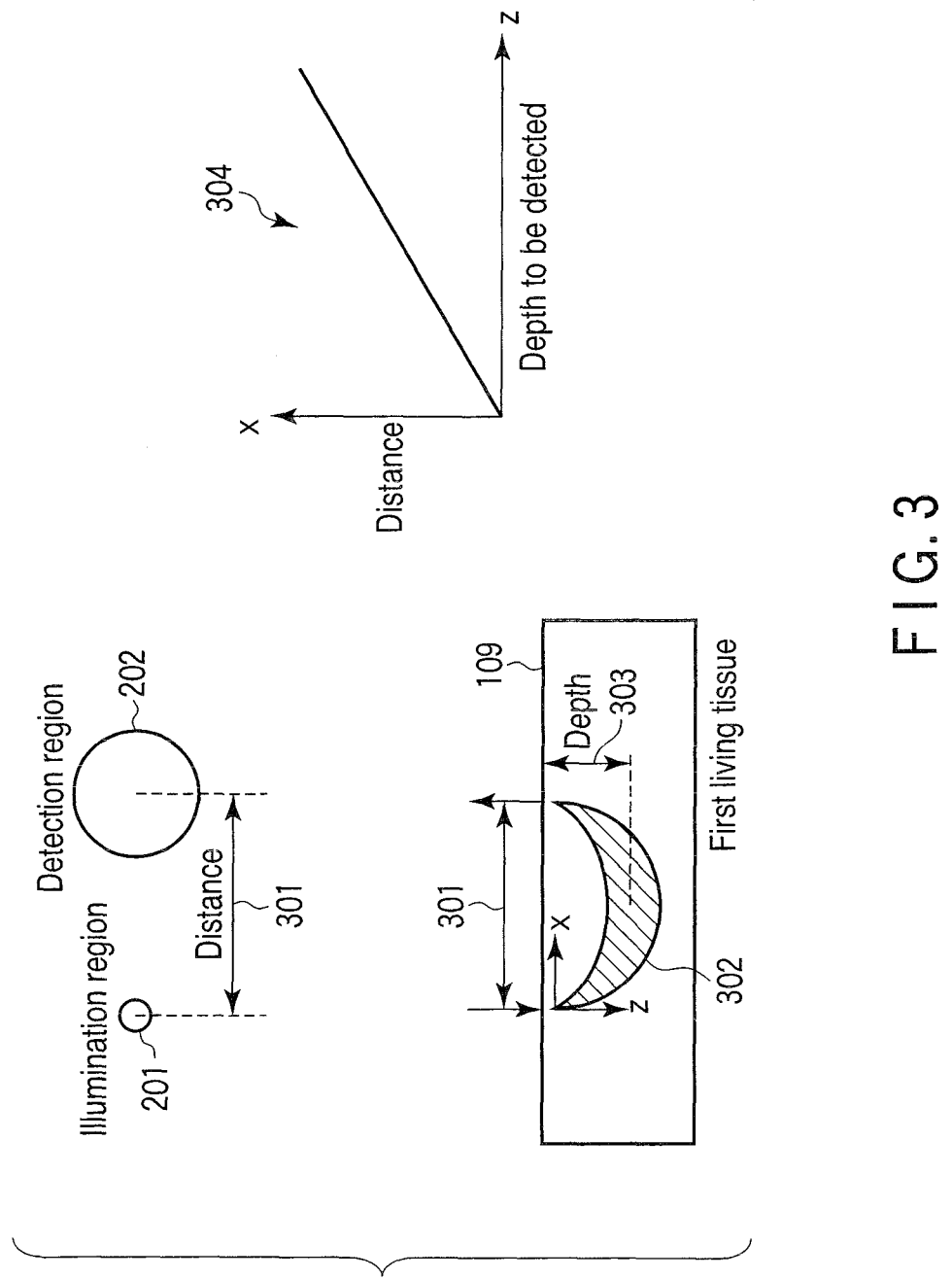
FIG. 3 is a view explaining an inter-center distance between an illumination region and a detection region and an observation depth.

FIG. 3 shows a schematic view of a disposition of the illumination region 201 and the detection region 202. As shown in the drawing, the back-scattered light 108 can be detected avoiding the reflected light and the diffused light by disposing the illumination region 201 away from the detection region 202 at a predetermined distance 301. At the time, in the first living tissue 109, a light detected by the detection region 202 mainly comprises a light passing through an illustrated region 302. Accordingly, when the distance 301 changes, inside information in a different depth 303 is detected. Accordingly, information in a predetermined depth can be imaged by designing the illumination device 102 and the detection device 103 so that the distance 301 is set to the predetermined distance.

In contrast, when the size of the detection region 202 is excessively increased although the distance 301 is prescribed, the illumination region 201 enters into the detection region 202. As a result, the reflected light and the diffused light are detected at the same time. Accordingly, the size of the detection region 202 and the distance 301 must be designed in consideration of the circumstances so that the illumination region 201 does not enter into the detection region 202.

Scattering characteristics in a living tissue are different depending on a region and an individual difference. However, it can be found from an experiment that an approximate proportional relation is established between the distance 301 and the depth 303 to be detected in any case as shown in a graph 304 in the drawing. A proportionality coefficient at the time is approximately x=2.8×z in a living tissue (x shows the distance 301, and z shows the depth 303 to be detected).

From what is described above, it is necessary to set the distance 301 to the predetermined distance or more to detect the second living tissue 110 existing in a depth. Specifically, it is found that it is sufficient to set the distance 301 to satisfy the following numerical expression to obtain a signal in an inside of the first living tissue 109 located in the depth z.

$$x \geq 2.8 \times z$$

In particular, it is found that it is sufficient to set the distance 301 to about 8 mm or more to obtain information in a depth of 3 mm or more whose acquisition is difficult by a conventional optical observation.

Figure 5:
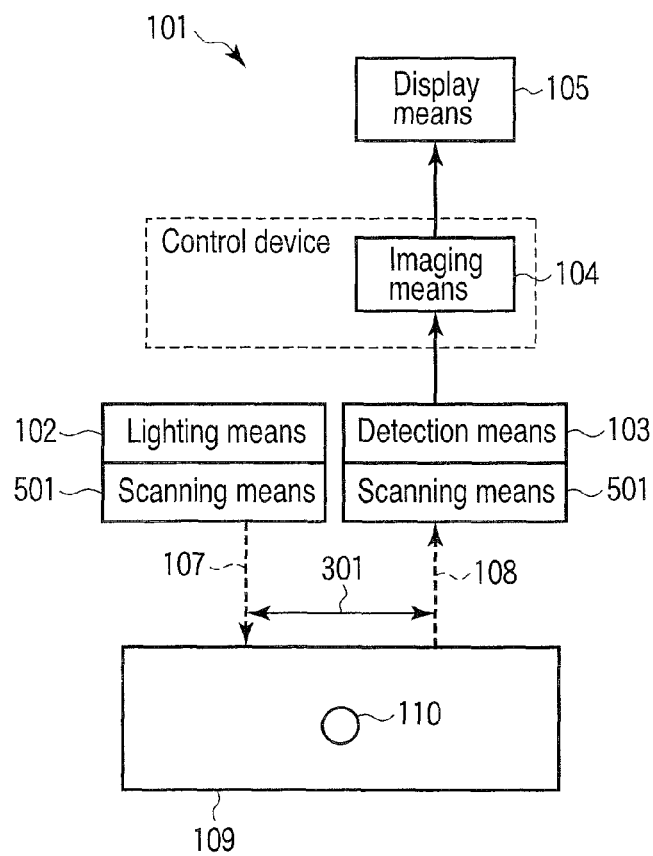
FIG. 5 is a block diagram showing a configuration of an apparatus for observing the interior of living body to which a scanning device is added.

FIG. 5 shows a block configuration view of the observation apparatus to which a scanning device 501 is added.

When the detection method is used, a change of light amount depending on presence or absence of the second living tissue 110 can be detected in a region between the illumination region 201 and the detection region 202. Accordingly, a two-dimensional distribution of the second living tissue 110 can be detected by adding the scanning device 501 to the illumination device 102 and the detection device 103 and performing scanning while prescribing the distance 301. At the time, a scanning direction is not limited to a linear direction. Further, two or more sets of the illumination region 201 and the detection region 202 may be disposed to illuminate and detect two or more points at the same time. With the configuration, an observation can be performed in a wider range. In the case, a separate distance between the respective sets may be arbitrarily determined, that is, the respective sets may be disposed adjacent to each other or may be disposed to the illumination regions and/or the detection regions which are away from each other.

When the imaging device 104 display light intensity signals detected at respective scanning points by causing scanning points to correspond to pixel positions in a display image, the imaging device 104 can display a two-dimensional distribution of the second living tissue 110 as a two-dimensional image. At the time, the light intensity signals may be displayed by being converted to color shade information or may be displayed by being converted to color information.

Figure 6:
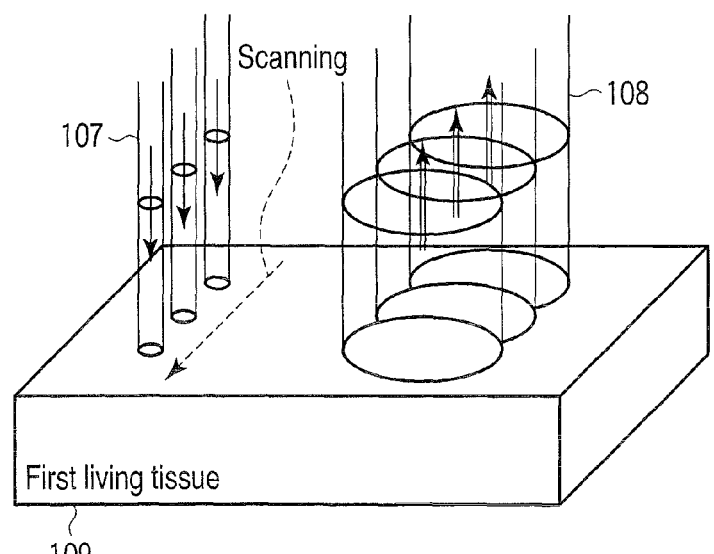
FIG. 6 is a schematic view showing a principle of an observation method of the invention when the scanning device is added.
Figure 7:
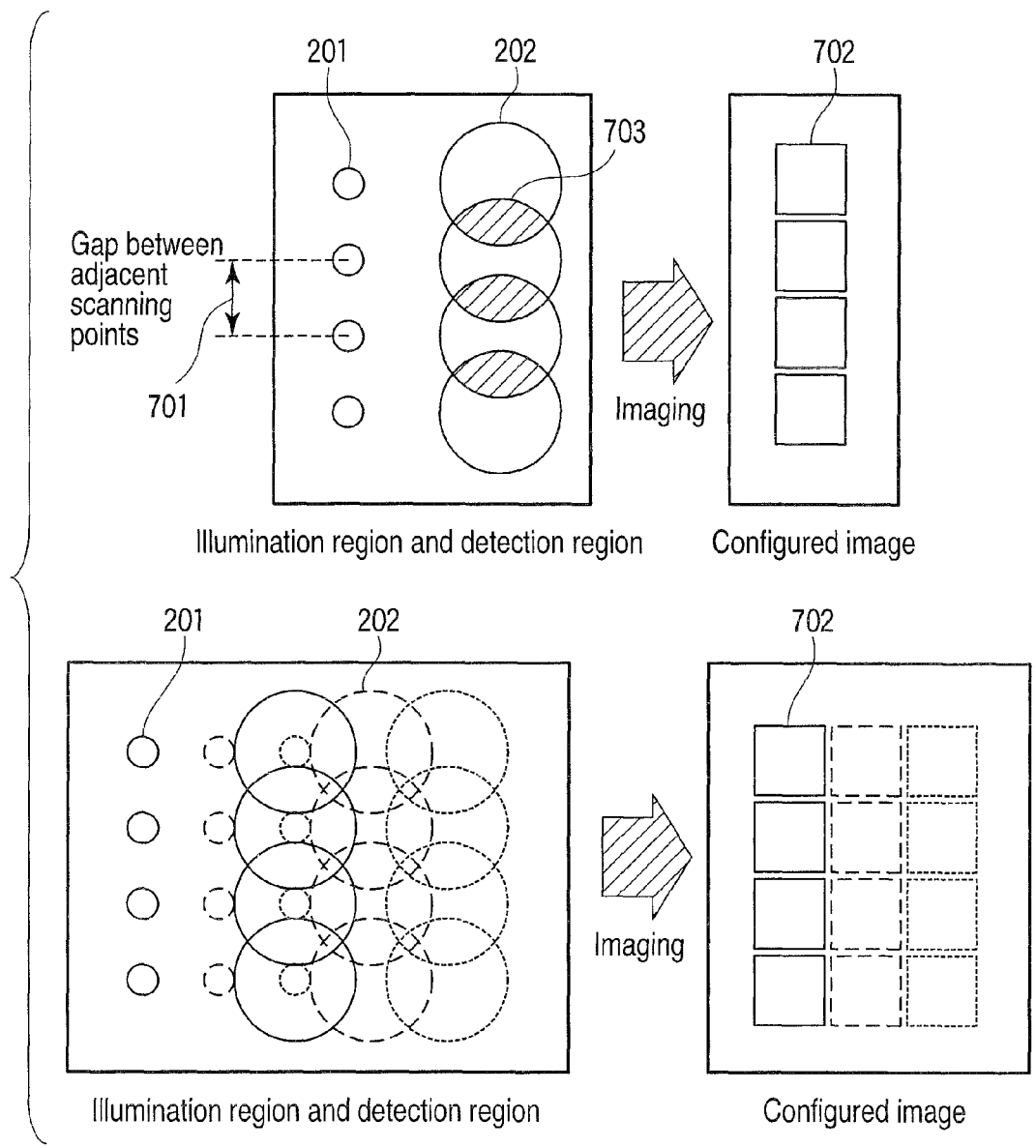
FIG. 7 is a schematic view of a surface of a first living tissue and a configured image when scanning is performed.

FIG. 6 and FIG. 7 show schematic views of movements of the illumination region 201 and the detection region 202 when scanning is performed. Pixels 702 of an image configured by the imaging device 104 are disposed according to a disposition of the scanning points. That is, a gap 701 of adjacent scanning points corresponds to a gap of the pixels 702.

At the time, when the size of the detection region 202 is made larger than the gap between the scanning points, intersecting portions 703 can be formed between the adjacent scanning points in the detection region. As a result, since a light amount between adjacent detection regions is smoothly changed, the same noise reduction effect as that when a smoothing process is performed on an image can be obtained.

At the time, when an image is configured in the gap of the scanning points regardless of the size of the detection region 202, an influence on the imaging device 104 caused by enlarging the detection region 202 can be avoided.

At the time, when it is intended to obtain the noise reduction effect and a detected light amount increase effect, the size of the detection region 202 is more increased. However, when the illumination region 201 enters into the detection region 202, the reflected light and the diffused light are detected at the same time. Thus, it becomes difficult to detect the back-scattered light. Accordingly, the size of the detection region 202 must be set in a range in which the illumination region 201 does not enter into the detection region 202.

To what extent it is necessary to enlarge a detection area (S) to permit even the weak back-scattered light 108 to optically detect the second living tissue 110 is determined by the overall characteristics of an observation system, an object to be observed, and a detection system. When a band width of the illumination light 107 is shown by BWL [Hz], a light density in the detection region 202 is shown by P [W/cm$^2$], a photoelectric conversion efficiency of a detector is shown by G [V/W], noise characteristics of the detector is shown by N [V], a change ratio of the light intensity depending on presence or absence of the second living tissue 110 is shown by r, an exposure time for detection is shown by t [s], the detection area S must satisfy the following relation expression. Otherwise, information of presence or absence of the second living tissue 110 is buried in a noise.

$$S \geq \frac{N}{(1-r) \cdot P \cdot G \cdot BWL \cdot t}$$

Figure 4:
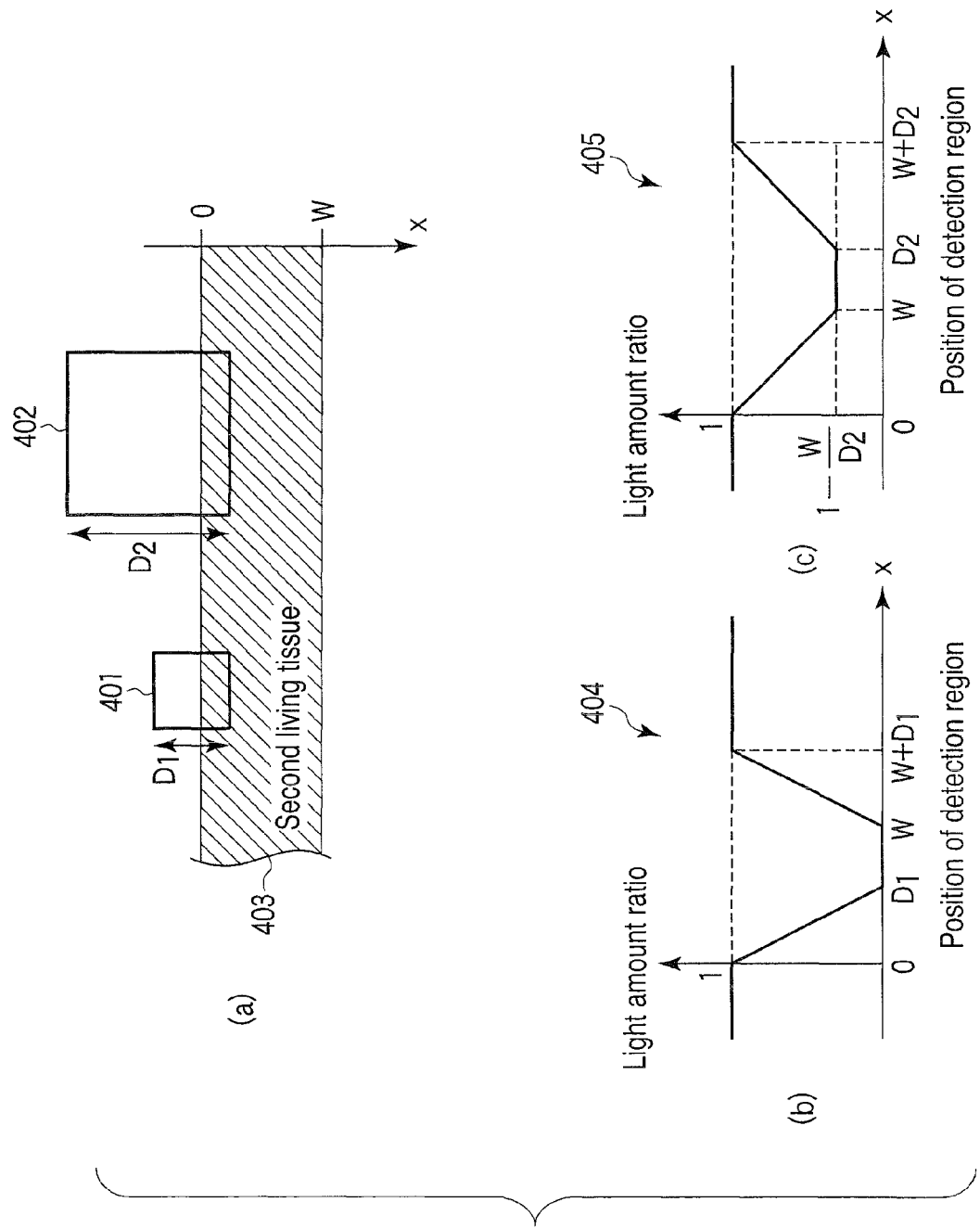
FIG. 4 is a view explaining a relation between a size of a second living tissue as an object to be detected and a size of a detection region and a change of light amount at the time.

Parts (a), (b), and (c) of FIG. 4 show a schematic view when the detection region traverses on an existing position of a second living tissue 403. It is assumed that the second living tissue, which is desired to be detected in a shape shown in the drawing, has a size W. The drawing shows two types of detection regions 401, 402. For the purpose of simplification, it is assumed that the detection regions are formed in square shape and both the detection regions 401, 402 are scanned in an x-axis direction of the drawing. The smaller detection region 401 has a side length set to D1<W, and the larger detection region 402 has a side length set to D2>W. Further, it is assumed that a light amount detected on the second living tissue 403 is 0, and a light amount detected at the other positions is 1.

When a calculation is performed in the virtual state, a change of detected light amounts is as shown in the parts (a) and (b) of FIG. 4. When the changes 404, 405 of the two light amount ratios are examined, it can be found that when the sizes of the detection regions 401, 402 become larger than the second living tissue W, a change ratio of the light amount ratios is lowered. That is, a signal contrast is lowered. When the contrast is lowered, it becomes difficult to detect the second living tissue.

As can be found also from the deduction achieved by the virtual model, when the detection region 202 is enlarged to increase a detected light amount, a higher detection capability can be kept by setting the detection region 202 to a size which can be accommodated in the second living tissue 110.

(First Embodiment)

Figure 8:
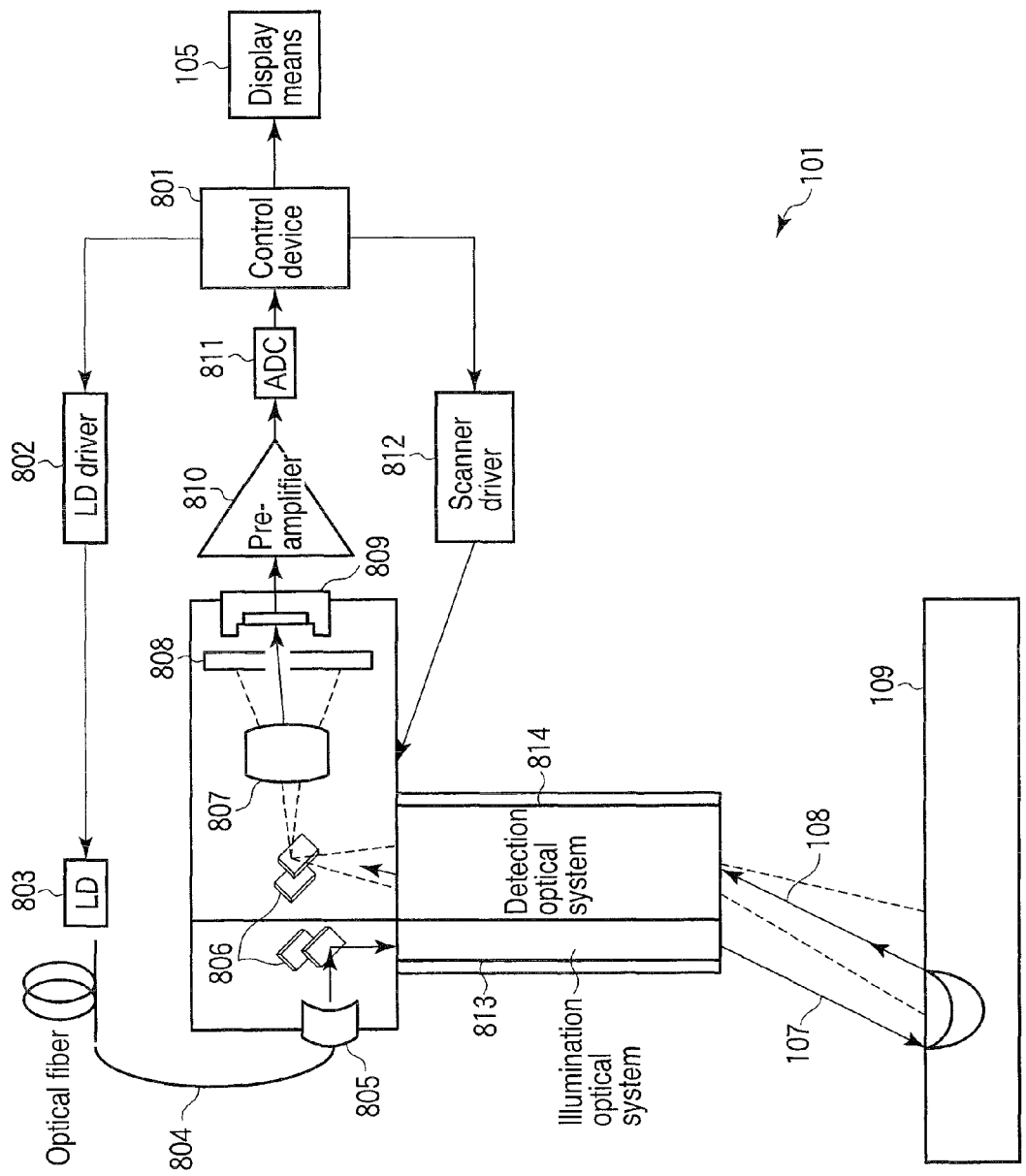
FIG. 8 is a configuration view of a first embodiment.

FIG. 8 shows an example of an apparatus to which a scanning device 501 is assembled.

A laser light is used as an illumination light, and an illumination device 102 of the laser light comprises an LD 803 and an LD driver 802 for driving the LD 803. The size of an illumination region 201 on a surface of a living tissue 109 can be simply reduced by using the laser light. The illumination light is transmitted by an optical fiber 804 and impinges on scanner mirrors 806 via an NA adjustment optical system 805. The light impinged on the scanner mirrors 806 is irradiated onto the surface of the living tissue 109 via an illumination optical system 813. Since a light outgoing from optical fiber passes via the NA adjustment optical system 805, the light can be converted to an illumination light having a desired NA and a minimized loss, for example, to a parallel light and can be irradiated onto the surface of the living tissue 109.

A detection device 103 changes a light intensity to a digital signal by a photodiode 809, a preamplifier 810, and an AD converter 811. The photodiode 809 may be an APD, and a photomultiplier tube, and the like. The light, which is incident on the photodiode 809, is a back-scattered light 108 transmitted from the surface of the living tissue 109 via a detection optical system 814. At the time, the back-scattered light 108 must be a light outgoing from a detection region 202 and further must be scanned together with an illumination light 108. Accordingly, after the back-scattered light 108 passes via a detection optical system, the back-scattered light 108 impinges on the scanner mirrors 806 as a scanning device and is incident on the photodiode 809 after the back-scattered light 108 passes via an aperture 808 to which an opening having a size and a shape via which only a light from the detection region 202 passes is formed. Lights from the portions other than the detection region 202 are entirely shielded and cut by the aperture 808. In the embodiment, although the scanner mirrors are employed as the scanning device, any means, which changes an optical axis such as a system for vibrating an optical fiber, a system for switching a plurality of light sources and detectors, and the like may be employed.

At the time, it is preferable to dispose a magnification adjustment optical system 807 (for example, a beam enlargement objective lens) and to adjust a beam diameter of an obtained detected light so that the beam diameter approximately agrees with the size of the opening of the aperture 808 so that the light can be easily shielded with high accuracy.

Further, when the aperture 808 is disposed at a position conjugate with the detection region 202 in the detection optical system 814, the light can be easily shielded with high accuracy. With the configuration of the detection system, a positional relation between the detection region 202 and the illumination region 201 can be simply designed. The positional relation between the detection region 202 and the illumination region 201 is as described above.

The scanner mirrors 806 are operated in response to a signal from a scanner driver 812 and controlled by a control device 801. The control device 801 configures an image in which a scanner position is related to a light intensity signal and causes a display device 105 to display the image. The display device 105 is a device capable of displaying an image, and a liquid crystal screen and a cathode-ray tube are assumed as the display device 105.

With the configuration of the embodiment, the back-scattered light 108 can be detected with high sensitivity and high accuracy although the configuration is simple, and a distribution of a second living tissue 110 in an inside of a first living tissue 109 can be picked up as a two-dimensional image at a high speed. Since an image can be picked up at the high speed, a moving image can be also picked up. Further, since the configuration is simple, the apparatus can be reduced in weight in its entirety.

(Second Embodiment)

Figure 9:
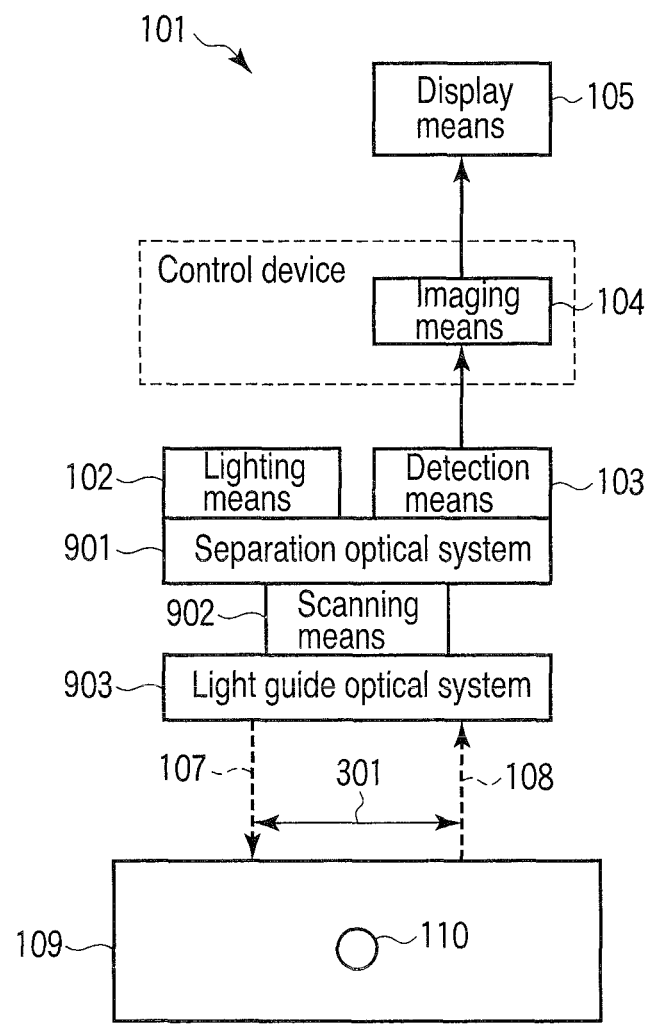
FIG. 9 is a configuration view of a second embodiment.

FIG. 9 shows, as one of embodiments, a block diagram of a configuration in which an illumination light 107 and a back-scattered light 108 are caused to pass via the same optical system.

The illumination light 107 and the back-scattered light 108 are scanned by a scanning device 902 by disposing a separation optical system 901 on an illumination device 102 side and on a detection device 103 side. A light guide optical system 903 is disposed on the scanning device 902 side, the illumination light 107 is irradiated onto a surface of a first living tissue 109, and the back-scattered light 108 is captured. With the configuration, since each one set of the scanning device and the light guide optical system can be employed, an apparatus can be made compact at a low price.

Figure 10:
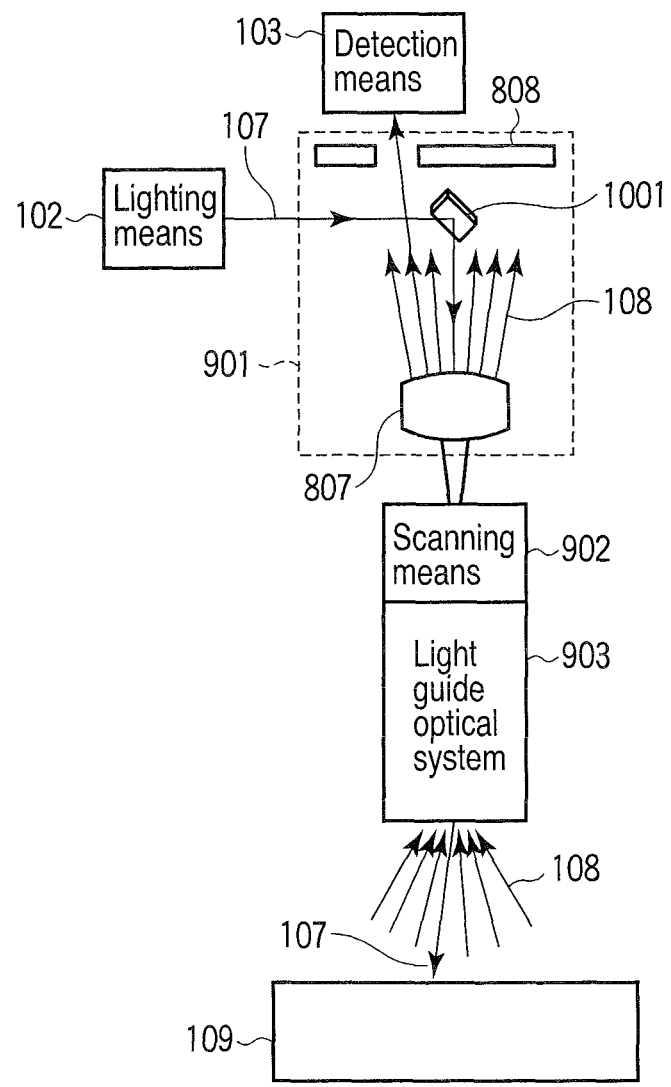
FIG. 10 is a view explaining a configuration of a separation optical system.

FIG. 10 shows a specific configuration of an apparatus to which the separation optical system 901 is assembled. A configuration, which detects only a light outgoing from a detection region 202 by causing the back-scattered light 108 captured by the light guide optical system 903 to be incident on the detection device 103 via a magnification adjustment optical system 807 and an aperture 808, is the same as the configuration of FIG. 8 described above. An optical element 1001, which separates an optical axis of the illumination light 107 from an optical axis of the back-scattered light 108, is disposed in the separation optical system 901, and a distance 301 between the illumination light 107 and the back-scattered light 108 can be prescribed by the optical element 1001. The optical element 1001 is an element which controls an optical axis, for example, a mirror and a prism. In the embodiment, although the optical axis of the illumination light 107 is controlled and causes the optical axis to join to the optical axis of the back-scattered light 108, the optical axis of the back-scattered light 108 may be controlled on the contrary or both the axes may be controlled.

Figure 11:
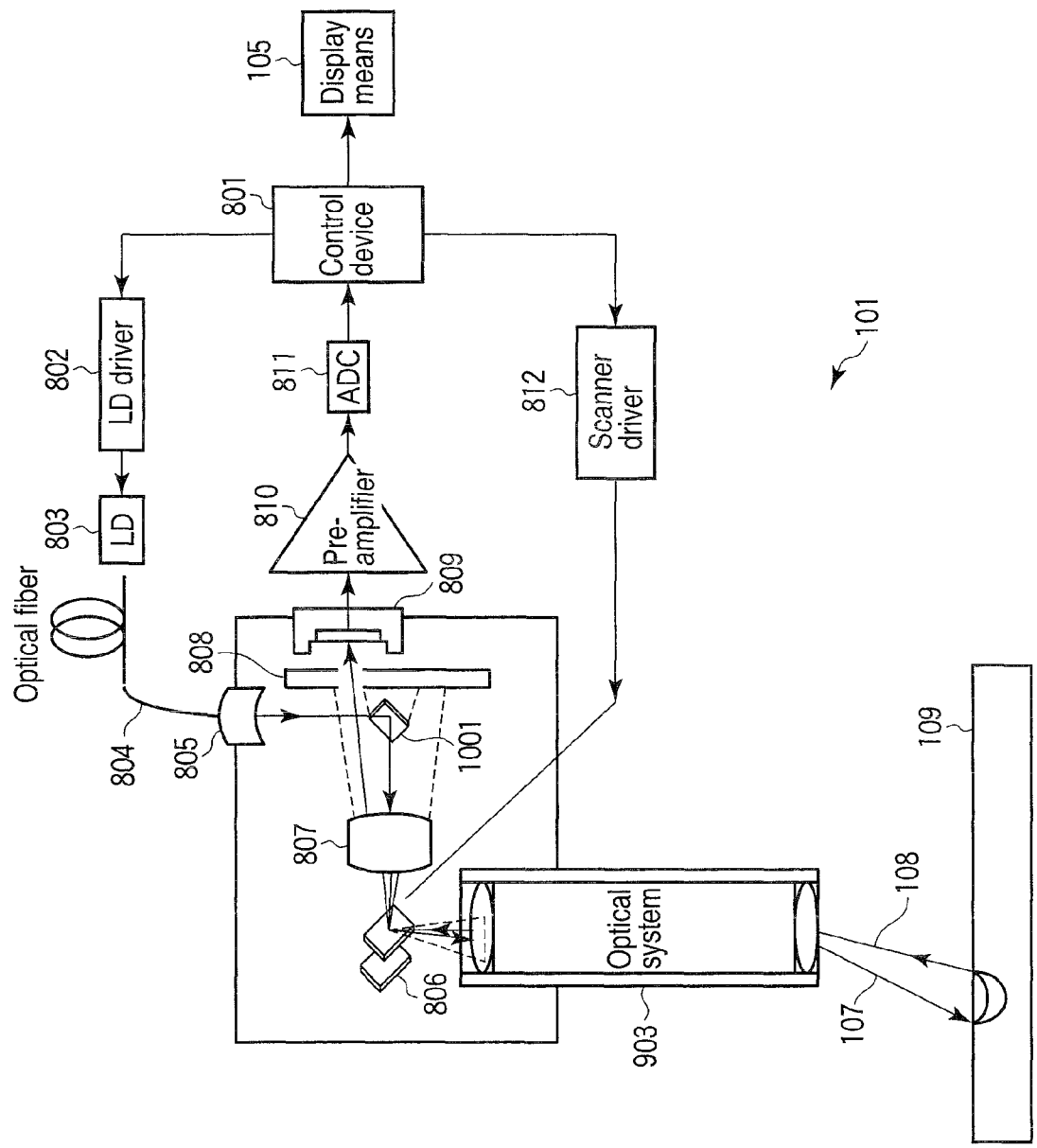
FIG. 11 is a configuration view showing an example of an observation apparatus according to the mode.

FIG. 11 is a view showing an example of an overall configuration of an observation apparatus 101 having the optical system shown in FIG. 10. With the configuration, since only one set of the scanning device 902 is employed and the light guide optical system 903 comprises a single optical axis, the apparatus can be reduced in weight and size in its entirety.

FIG. 12 shows a molar extinction coefficient of hemoglobin, and FIG. 13 shows an absorption coefficient of water.

When a blood, which mainly contains red blood cells mainly comprising hemoglobin, is observed as a second living tissue 110, if only a light, which passes via a position at which the blood exists, is absorbed, an existing position at which the blood exists can be drawn as if the position is a shadow picture. Accordingly, when a light including a wavelength having a large absorption coefficient of hemoglobin, which is a component of the blood, and moisture is employed as the illumination light 107, the existing position of the blood can be drawn as if it is the shadow picture. Specifically, as shown in the drawing, it is sufficient to employ a light including at least a wavelength 1201 in a range of 400 to 600 nm, a wavelength 1202 in a range of 800 to 1000 nm, or a wavelength 1301 in a range of 1350 to 1550 nm.

At the time, when a first living tissue 109 also contains a large amount of moisture, it is difficult to detect the second living tissue 110 by the light including the wavelength 1301 in the range of 1350 to 1550 nm. Further, when the second living tissue 110 exists at a deep position of 3 mm or more, an infrared light, which is less influenced by a light scattering due to the first living tissue 109 is preferable. Accordingly, when a blood or a blood vessel is observed as the second living tissue 110, it is preferable to use a light including a wavelength 1203 in a range of 900 to 1000 nm.

In the embodiment, the small illumination region 202 is illuminated using the illumination light 107 having the limited wavelength as described above. In the case, it is most simple to use a laser light to create a fine parallel light having a limited wavelength. When the illumination light 107 comprising the fine parallel light is created by the laser light, even if a distance between an optical system 813 and the surface of the first living tissue 109 and a distance between the optical system 903 and the surface of the first living tissue 109 change, the size of the illumination region 201 can be kept constant at all times. Further, when the laser light is guided using an optical fiber, an optical system configured in various modes can be disposed easily, which is preferable in that not only a degree of freedom of a configuration increases but also a soft endoscope can be designed.

With these configurations, according to the invention, there can be provided an apparatus for observing the interior of living body which can observe an inside of an object having a light scattering property with high sensitivity and can efficiently obtain a distribution image of a heterogeneous portion in a deep portion of a living body.

Since a time necessary to create an image can be reduced by efficiently obtaining an image, an observation of an inside portion (deep portion) in a scene, in which a moving object to be observed is picked up, and in an image pick-up scene, in which an observation apparatus itself is liable to move, can be coped with. Therefore, according to the invention, a living body inside observation function can be provided to an image pick-up apparatus which uses a living body in motion as an object, for example, to a medical endoscope, an operation hard mirror (hard endoscope), a capsule endoscope, and an in vivo (or ex vivo) observation microscope.

According to the invention, an inside observation method, which executes the observation principle described above can be also provided to an apparatus in addition to the apparatus described above. Further, to perform the method, there are also provided software for executing various observation apparatuses and a control program for executing an observation operation by the apparatuses.

Further, in a first aspect, it may be understood that respective modes are inventions expressed as shown below. The respective modes (A1) to (A24) will be described together with the effects thereof.

(A1) The inside observation apparatus is characterized in that, in an observation method of irradiating an illumination light onto a surface of an object and detecting a back-scattered light of the illumination light, an area of a specific detection region is made larger than an area of an illumination region.

According to the mode, in an observation of a body to be observed in an inside an object having a light scattering property, a detected light amount can be increased by a simple and less expensive configuration and a time necessary to detection can be reduced.

(A2) The inside observation apparatus is characterized in that the apparatus includes an illumination device and a detection device which are disposed to prescribe the distance between the illumination region and the detection region.

According to the mode, information in a predetermined depth can be imaged.

(A3) The inside observation apparatus is characterized in that the detection region includes the illumination device and the detection device which are disposed so as not to include at least the illumination region.

According to the mode, since there is not a possibility that a reflected light and a diffused light are detected, only a back-scattered light can be detected.

(A4) The inside observation apparatus is an apparatus for observing an object including a first living tissue and a second living tissue and characterized in that an inter-center distance x between the illumination region and the detection region is prescribed to be set as shown by the following numerical expression with respect to an approximate depth z in which it is predicted that the second living tissue exists.

$x \geq 2.8 \times z$

According to the mode, a signal to a desired depth in an inside of an object can be obtained.

(A5) The inside observation apparatus is characterized in that two or more sets of the illumination position and the detection position are disposed on a surface of a first living tissue and images corresponding to the respective positions are configured.

According to the mode, a distribution of a body existing in an inside of an object can be detected.

(A6) The inside observation apparatus is characterized in that the apparatus includes a scanning device configured to scan the illumination position and the detection position and to perform imaging for configuring images corresponding to the illumination position and the detection position.

According to the mode, a distribution of a body existing in an inside of an object can be detected and imaged.

(A7) The inside observation apparatus is characterized in that the apparatus makes the size of the detection region larger than an inter-center distance between the detection region and an adjacent detection region so that an intersecting portion is created between detection regions.

According to the mode, since a light amount between adjacent detection regions changes smoothly, the same noise reduction effect as that when a smoothing process is performed on an image can be realized.

(A8) The inside observation apparatus is characterized in that the apparatus determines the size of a detection region so that the illumination region does not enter into the detection region.

According to the mode, only a back-scattered light can be detected excluding a reflected light and a diffused light from a surface of an object.

(A9) The inside observation apparatus is characterized in that the apparatus configures an image in correspondence to a gap when a scanning is performed.

According to the mode, an influence on an imaging device caused by enlarging a detection region can be avoided.

(A10) The inside observation apparatus is characterized in that the apparatus causes the size of the detection region to satisfy the following numerical expression.

$D \leq W$ (The size of the detection region in one direction is shown by D, and the size of the second living tissue desired to be found is shown by W.)

According to the mode, it can be realized that only a light from the detection region can be caused to be incident on a detector.

(A11) The inside observation apparatus is characterized in that the apparatus disposes an aperture, which extracts only a back-scattered light from the detection region, to the detection device.

According to the one mode, lights from the portions other than the detection region can be shielded with high accuracy.

(A12) The inside observation apparatus is characterized in that the apparatus disposes an aperture at a position conjugate with the detection region in an optical system for guiding a back-scattered light from a surface of the first living tissue up to the detection device.

According to the one mode, the lights from the portions other than the detection region can be easily shielded with high accuracy.

(A13) The inside observation apparatus is characterized in that the apparatus disposes a magnification adjustment optical system between the scanning device and the aperture.

According to the one mode, since the scanning device and a light guide optical system can be configured as one device, the inside observation apparatus can be manufactured compactly at a low price.

(A14) The inside observation apparatus is characterized in that the apparatus includes a light guide optical system for guiding the illumination light and the back-scattered light to the same optical system and a separation optical system for causing an illumination light to be incident on the light guide optical system and extracting only a back-scattered light from the detection region.

According to the mode, it can be simply realized to limit a wavelength band region of an illumination light and to reduce an illumination region to a small size.

(A15) The inside observation apparatus is characterized in that the apparatus uses a laser light source as an illumination light.

According to the mode, a degree of freedom of a configuration of the apparatus can be improved.

(A16) The inside observation apparatus is characterized in that the apparatus uses an optical fiber to guide an illumination light.

According to the mode, it can be realized that the size of an illumination region is kept to a predetermined size without depending on an observation distance.

(A17) The apparatus for observing the interior of living body is characterized in that the object is a first living tissue and the body is a second living tissue.

According to the mode, a body to be observed can be observed as to a depth of 3 mm or more in an inside of a living tissue as an object.

(A18) The apparatus for observing the interior of living body is characterized in that the apparatus prescribes an inter-center distance between the illumination region and the detection region to 8 mm or more.

According to the mode, a signal can be obtained as to a depth of 3 mm or more in an inside of a living tissue.

(A19) The apparatus for observing the interior of living body is characterized in that the apparatus causes an area S of the detection region to satisfy the following numerical expression.

$$S \geq \frac{N}{(1-r) \cdot P \cdot G \cdot BWL \cdot t}$$

(A band width of the illumination light is shown by BWL, a detection light density in the detection region is shown by P, a conversion coefficient for converting the detected light to the light intensity data is shown by G, a noise floor of the detection device is shown by N, an exposure time in the detection is shown by t, and a change ratio of the light intensity data depending on presence or absence of the second living tissue is shown by r.)

According to the one mode, information of presence or absence of a second living tissue can be detected without being buried in a noise.

(A20) The inside observation apparatus is characterized in that the apparatus includes an NA adjustment optical system so that the illumination light is made to a parallel light in an irradiation end to the first living tissue (from a time at which a light outgoes from an illumination device to a time at which the light is incident on a tissue).

According to the mode, the detection region can be enlarged in a range in which a detection capability is not lowered.

(A21) The apparatus for observing the interior of living body is characterized in that the illumination light is a light having a wavelength of at least 400 to 600 nm, 800 to 1000 nm, or 1350 to 1550 nm.

According to the mode, an existing position of a blood can be drawn.

(A22) The apparatus for observing the interior of living body is characterized in that the illumination light is a light having a wavelength of at least 900 to 1000 nm.

According to the mode, even when the first living tissue contains a large amount of moisture, a blood or a blood vessel existing in a depth of 3 mm or more can be detected.

(A23) The endoscope is characterized in that the endoscope is assembled to a medical endoscope.

According to the mode, an observation in an inside of a living body can be applied to a medical site.

(A24) The endoscope is characterized in that the endoscope is assembled to an operation hard endoscope.

According to the mode, an observation in an inside of a living body can be applied to a medical site.

Further, the following conventional problems can be solved by the modes described above.

To obtain a tomographic image, a measurement must be performed at many measurement points. A conventional apparatus includes a plurality of detection elements disposed to an apparatus main body. A user performs a measurement while moving the apparatus to respective measurement points. Accordingly, the conventional apparatus and method have a problem in that a long time is necessary in the measurement.

Further, the method and the apparatus described in Jpn. Pat. Appln. KOKAI Publication No. 2006-200943 performs a measurement by causing a light source and a detection element to be in contact with a surface of a living body. Accordingly, in the method and the apparatus, each time the apparatus is moved to respective measurement points, an image must be obtained by causing the light source and the detection element to be in contact with the surface of the living body. Accordingly, the method and the apparatus have a problem in that a longer time is necessary.

The problem is also solved by the modes described above according to the invention. With these modes, there is provided an inside observation apparatus which can efficiently obtain a distribution image of a heterogeneous portion. With these modes, there is provided an inside observation apparatus which can observe a specific depth region in an inside of an object with sensitivity higher than a conventional inside observation apparatus. With these mode, there is provided an inside observation apparatus which can observe an inside of an object in a region deeper than a conventional region.

Further, with these modes, there can be provided a method and an apparatus which can efficiently obtain a tomographic image in a depth where a heterogeneous portion contained in an inside of an object having a light scattering property exists.

With these modes, there can be provided a method and an apparatus which can simply obtain a lot of information in a short time as well as can easily create a tomographic image by moving an irradiation position.

With these modes, there can be provided an inside observation apparatus which can observe a specific depth region in an inside of an object with sensitivity higher than a conventional inside observation apparatus.

Further, with these modes, there can be provided a method and an apparatus which can observe a region deeper than a conventional region as to an inside of an object.

Accordingly, with these modes, there can be provided a method and an apparatus which can observe an inside of a living body better than a conventional method and apparatus.

<Second Aspect>

One or more modes of a second aspect of the invention described below may be used in combination with one or more modes of the first aspect described above. Further, one mode shown in the second aspect may be independently used or one or more modes shown in the second aspect may be used in combination.

(Third Embodiment)

Figure 14:
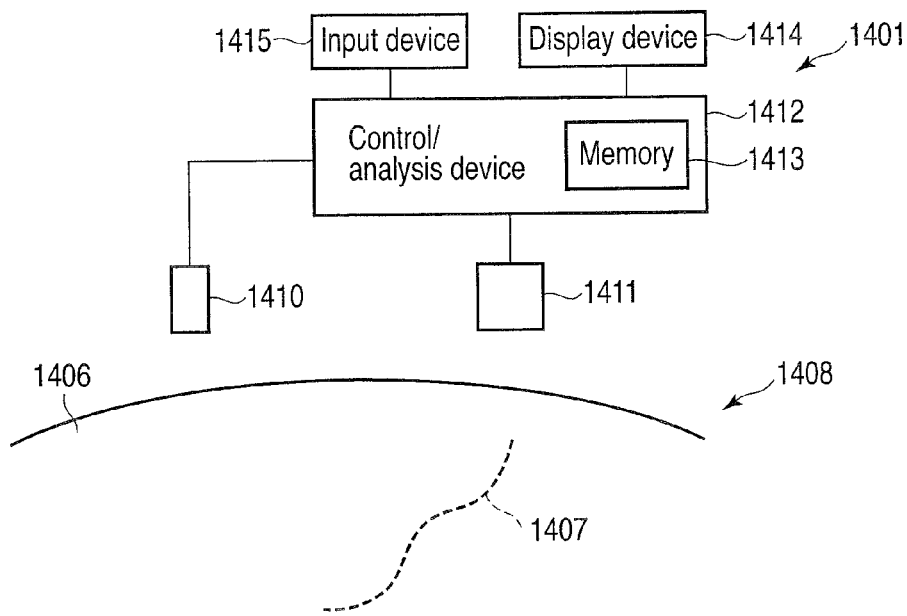
FIG. 14 is a block configuration view of an apparatus for measuring the interior of turbid media according to a third embodiment.

FIG. 14 is a block configuration view of a an apparatus for measuring the interior of turbid media 1401 according to a third embodiment of the invention. As shown in the drawing, the apparatus for measuring the interior of turbid media 1401 includes a movable light irradiation device 1410, a detection device 1411, a control/analysis device 1412, a memory 1413, a display device 1414, and an input device 1415.

The light irradiation device 1410 is an lighting means which irradiates a light having optical characteristics which differ in an object to be measured 1407 in an inside of a turbid media 1408 and in a scattering medium 1406 in the vicinity of the object to be measured 1407. Although an LD and the like can be used as the light irradiation device, the light irradiation device is not limited thereto. A light having a wavelength, which is absorbed by, for example, an object to be measured but is not absorbed by a scattering medium, may be used as a light irradiated from the light irradiation device 1410. The light irradiation device 1410 irradiate a light to the turbid media 1408 based on a control signal from the control/analysis device 1412.

The detection device 1411 detects an intensity of a back-scattered light of a light irradiated by the light irradiation device 1410 after the light is reflected, scattered, and absorbed by the scattering medium 1406 of the turbid media 1408 and by the object to be measured 1407 and outgoes from a surface of the turbid media 1408. The detection device 1411 detects the back-scattered light based on a control from the control/analysis device 1412.

The light irradiation device 1410, the detection device 1411, the display device 1414, and the input device 1415 are connected to the control/analysis device 1412 by a signal circuit via which an electric signal is transmitted.

The control/analysis device 1412 controls the operations of the light irradiation device 1410 and the detection device 1411 as well as analyzes data detected by the detection device 1411 and confirms whether or not the object to be measured 1407 exists in an inside of the turbid media 1408. When the object to be measured 1407 exists in the inside of the turbid media 1408, a position and a depth, at and in which the object to be measured 1407 actually exists in the turbid media 1408, are analyzed from the distance between a light irradiation position and a position, at which the object to be measured 1407 is confirmed, and the like. Further, the control/analysis device 1412 includes the memory 1413 for storing detected data.

From a view point of an view angle of an optical system of an image pickup device, when the detection device 1411 is away from the turbid media 1408 without in contact therewith, the detection device 1411 can measure a wider region. Thus, the light irradiation device 1410 and the detection device 1411 in the embodiment perform an irradiation and a detection away from the turbid media at a predetermined distance without in contact therewith. With the operation, the detection device 1411 can measure a wide region of the turbid media at a time. The region detected by the detection device 1411 at a time is called a measurement region here.

Next, an operation of the apparatus for measuring the interior of turbid media 1401 according to the embodiment will be explained.

Figure 15:
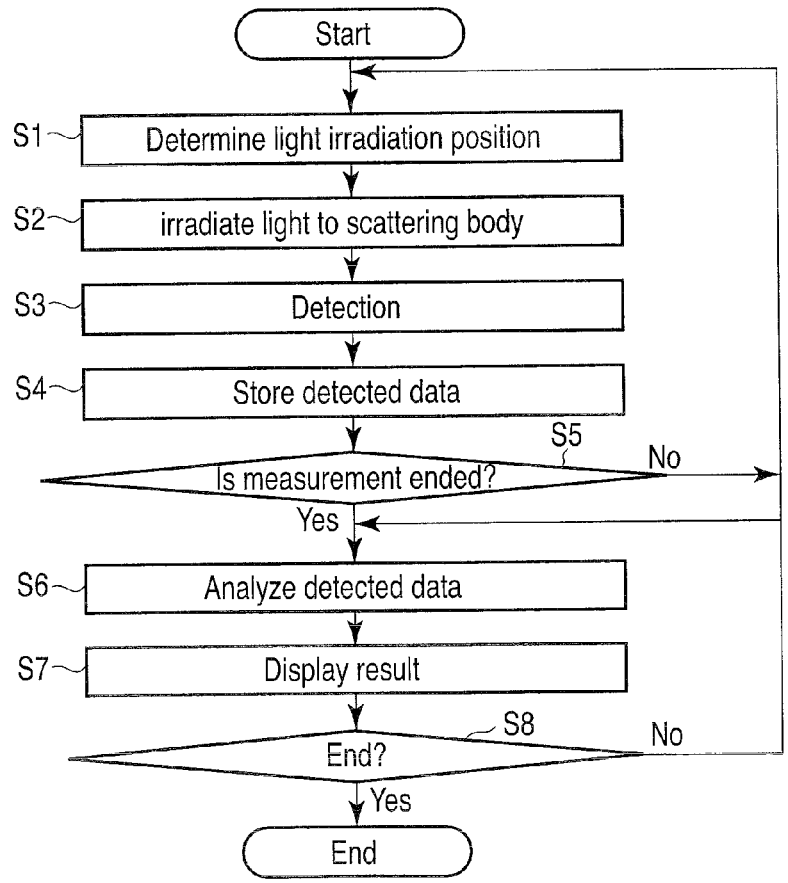
FIG. 15 is a flowchart showing an operation of an apparatus for measuring the interior of turbid media according to the invention.

FIG. 15 is a flowchart showing the operation of the apparatus for measuring the interior of turbid media 1401 according to the invention. At S1, a position at which a light is irradiated to the turbid media is determined. At S2, the light is irradiated to the turbid media from the light irradiation device 1410. At S3, the detection device 1411 detects the intensity of the back-scattered light which is reflected, scattered, and absorbed by the scattering medium 1406 in the inside of the turbid media 1408 and returns to the surface of the turbid media again. Detected data is stored in the memory 1413 at S4. At S5, it is determined whether or not a measurement is finished, and when the measurement is not finished, a process returns to S1 and continues the measurement. When the measurement is finished, the process goes to S6.

At S6, the control/analysis device 1412 analyzes the data stored in the memory 1413. A result of the analysis is displayed on the display device 1414 at S7. At S8, it is determined whether or not the measurement is finished, and when the measurement is not finished, the process returns to S1 and continues the measurement or returns to S6 and continues the analysis.

The analysis at S6 is performed by the following analysis method.

As an analysis method, a position and a depth of an object to be measured are analyzed from the obtained data.

Figure 16:
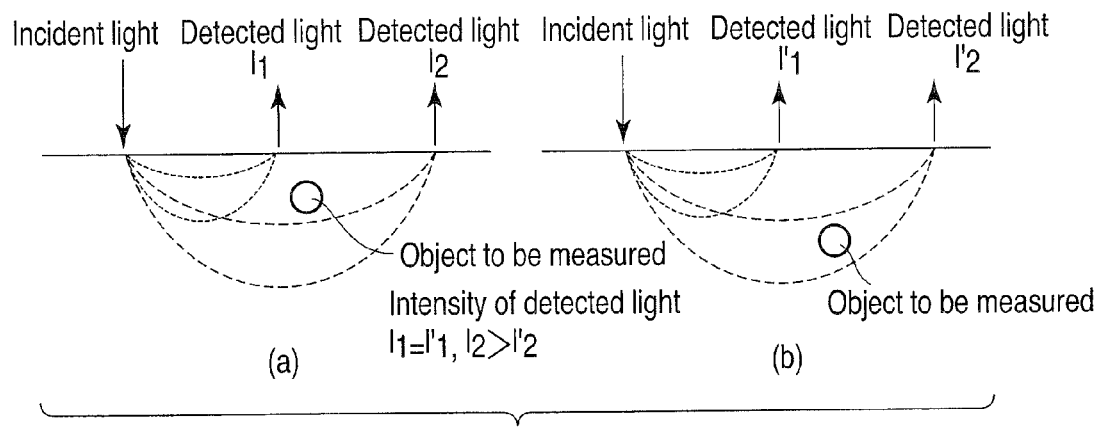
FIG. 16 is a conceptual view showing how a light in an inside of a turbid media is transmitted.

FIG. 16 is a conceptual view showing how a light in the inside of the turbid media is transmitted. In general, a light irradiated to a turbid media loses an anisotropy of scattering while the light repeats scattering and becomes near to isotropic scattering. As a result, it is known that a cross section of an average light path becomes a banana shape.

In parts (a) and (b) of FIG. 16, a lot of light transmitted near to the surface of the turbid media is detected at a position $I_1$ close to an irradiation position of the light. In contrast, a lot of light transmitted in a deeper portion of the turbid media is detected at a position $I_2$ away from the light irradiation position. As described above, a depth, via which the detected light is transmitted, changes depending on a distance from the irradiation position of the light to a detection position. In what depth in the inside of the turbid media the object to be measured exists is analyzed by making use of the property.

For example, in the part (a) of FIG. 16, the object to be measured exists near to a surface between the detection positions $I_1$ and $I_2$. In the case, no change is found in the detected lights at the detection positions $I_1$ and $I_2$. In contrast, in the part (b) of FIG. 16, the object to be measured exists at a deeper position between the detection positions $I'_1$ and $I'_2$. At the time, although no change is found in the detected light at the detection position $I_1$, the detected light at the detection position $I_2$ is lowered and weakened, thereby the position and the depth of the object to be measured are determined.

As described above, when a point at which the intensity of the back-scattered light is weak is found, an analysis is performed based on the distance between the point and the irradiation position of the light, and a depth and a position are calculated.

Further, as another analysis method, a tomographic image in a predetermined depth is created (that is, a construction of an image) from the data of the obtained intensity of the back-scattered light.

Figure 17:
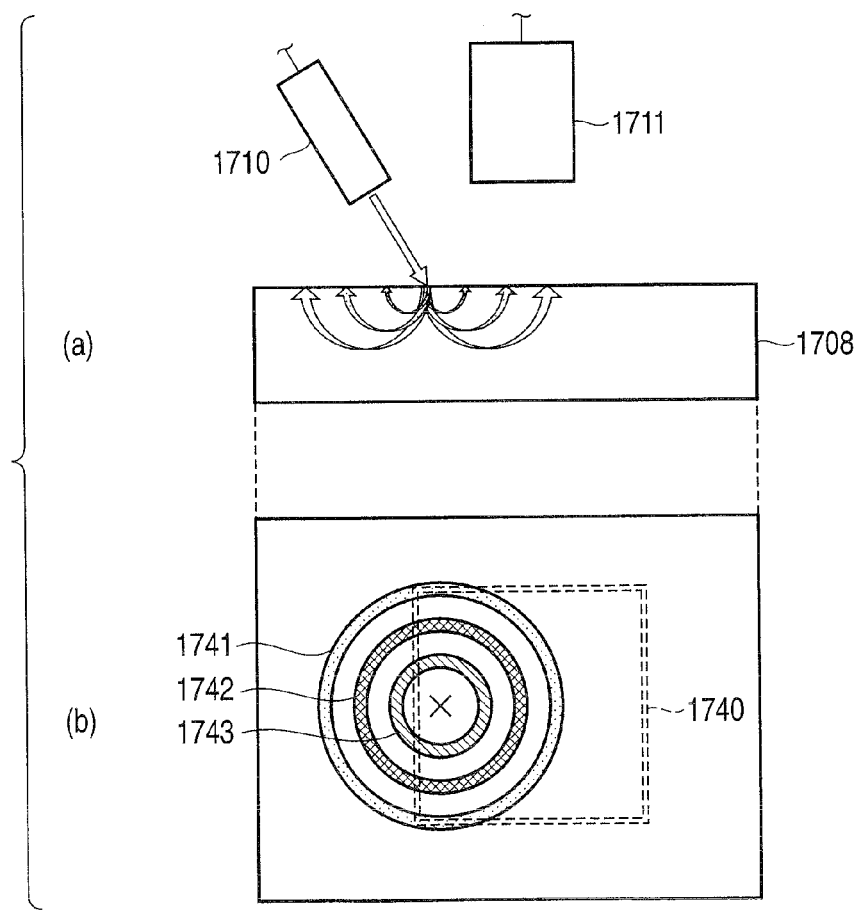
FIG. 17 is a schematic view of two-dimensional image data obtained by the apparatus for measuring the interior of turbid media according to the third embodiment.

Parts (a) and (b) of FIG. 17 show schematic views of a back-scattered light measured in a measurement region. A position at which a light is irradiated onto the turbid media from a light irradiation device 1710 is shown by a cross mark, and a measurement region 1740 which is scanned by a detection device 1711 is shown by dotted lines. A back-scattered light, which is reflected, scattered, and absorbed by a turbid media 1708 and outgoing from the surface of the turbid media is formed in a state of concentric circles about the irradiation position as shown in the drawing. As shown by the part (a) of FIG. 17, a concentric circle having a larger diameter shows a light passing via a deeper portion of the turbid media. In the part (b) of FIG. 17, it can be regarded that concentric regions 1741, 1742, and 1743 show information of approximately same depths, respectively. Further, since the depths correspond to distances from the irradiation position to the concentric circles, the depths are deeper in the order of the concentric regions 1741, 1742, and 1743. Accordingly, in scanning, when the detection device 1711 extracts the data of an intensity of the back-scattered light from at least a part of the concentric regions, image data in a predetermined depth can be selectively taken out, and a tomographic image in the depth can be created from the selected data.

Note that the analysis method can simply obtain a lot of information which can be used for analysis by performing a measurement by changing a position of the light irradiation device 1710.

Figure 18:
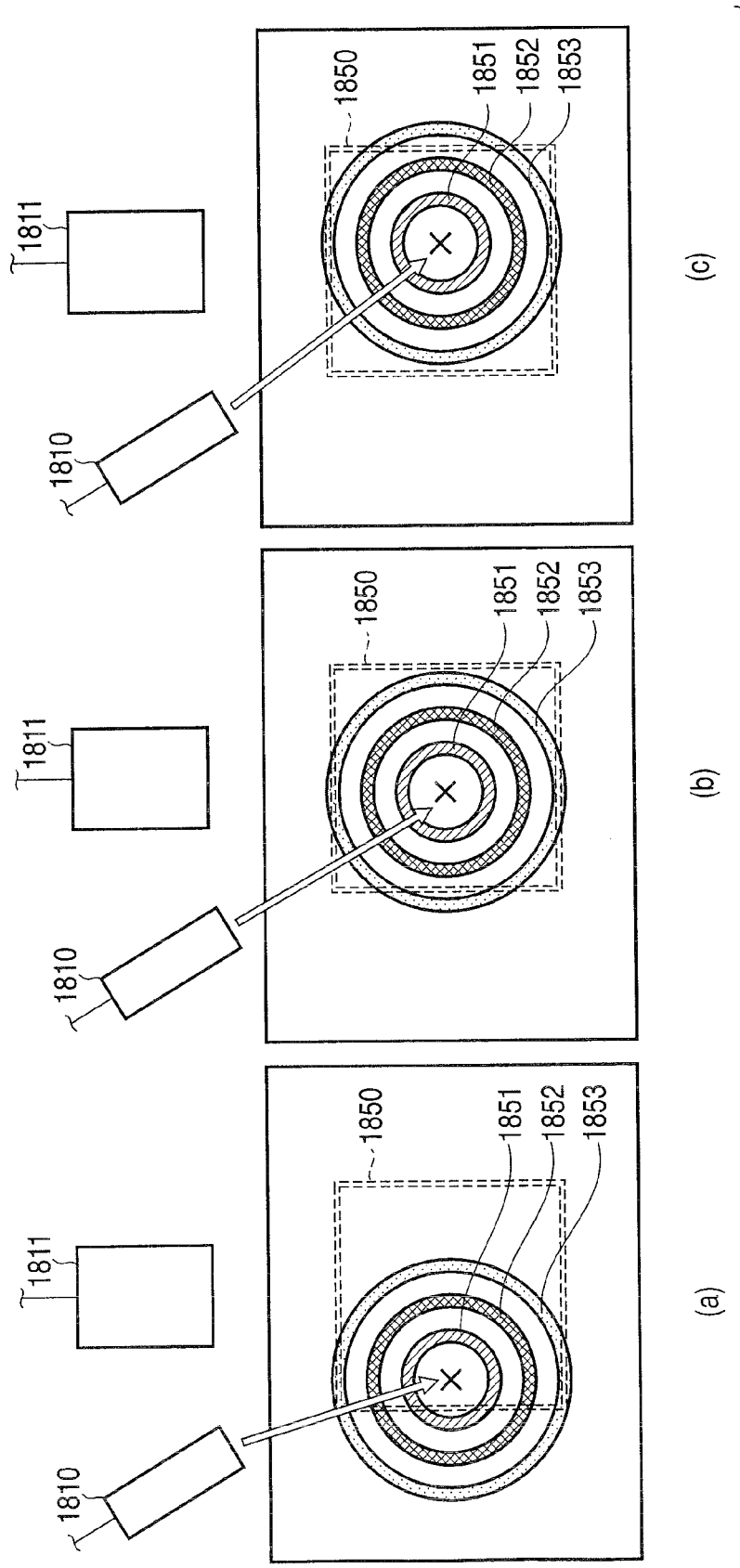
FIG. 18 is a schematic view of two-dimensional image data when a measurement is performed while changing an irradiation position.

Parts (a), (b), and (c) of FIG. 18 show how a measurement is performed by changing an irradiation position to which a light is irradiated by a light irradiation device 1810. A detection device 1811 is fixed, and a measurement region 1850 does not also move. However, a concentric region described above is moved by varying the irradiation position to which light is irradiated by the light irradiation device 1810.

Further, as another analysis method, information in an arbitrary depth at a desired position can be obtained by changing a region to be detected to 1851, 1852, and 1853.

As described above, when the light irradiation device 1810 and the detection device 1811 are scanned and analyzed so as to obtain data at a position away from a desired position by the same distance as the distance between the desired position and the irradiation position, information in an arbitrary depth at the desired position can be simply obtained. In the case, distances between a desired position, an irradiation position, and a position of data to be analyzed are determined depending on a depth where it is desired to obtain information.

Note that, in the respective analysis methods described above, when the distance between the irradiation position and the detection position is determined in the data analysis step S6 of FIG. 15, a focal length, a magnification, and the like of an optical system of the detection device 1411, 1711, or 1811 is taken into consideration.

As described above, in the embodiment, since a degree of freedom of the irradiation position and the detection position is high, information in an arbitrary depth at a desired position can be easily obtained.

(Fourth Embodiment)

Next, a fourth embodiment of the invention will be explained. FIG. 19 is a block configuration view of an apparatus for measuring the interior of turbid media 1900 according to the fourth embodiment. The apparatus for measuring the interior of turbid media 1900 includes a light illumination device 1909 and a detection device 1910 which are movably disposed therein.

According to the apparatus for measuring the interior of turbid media 1900 of the fourth embodiment, the light irradiation device 1909 and the detection device 1910 are moved and disposed at positions where the light irradiation device 1909 and the detection device 1910 have the same distance about a desired position. With the disposition, information in an arbitrary depth at a desired position can be obtained. The depth of the obtained information can be easily changed by appropriately adjusting distances between the desired position and the light irradiation device 1909 and the detection device 1910.

The invention is not limited to the embodiment and may be variously modified and changed in a scope which does not depart from the gist of the invention. Further, a plurality of components disclosed in the embodiment may be appropriately combined. For example, some components may be deleted from all the components shown in the embodiment. Further, components in different embodiments may be appropriately combined.

It may be understood that the mode described above is the following invention.

That is, the invention is an apparatus for measuring the interior of turbid media (that is, a turbid media inside observation apparatus), which obtains information of an object to be measured (that is, an object to be observed) in an inside of a turbid media and a measurement method using the apparatus for measuring the interior of turbid media, wherein the apparatus for measuring the interior of turbid media comprises an illumination device (that is, a light irradiation device) configured to irradiate a light having optical characteristics, which are different in the object to be observed and in the turbid media, to the turbid media, a detection device configured to detect a back-scattered light of the light irradiated by the illumination device, and an analysis device configured to confirm whether or not the object to be measured exists in the data obtained by the detection device and to obtain position information including a depth of the object to be measured in the turbid media from distances to the positions where the irradiation position and the object to be measured are confirmed, and the illumination device and the detection device perform a measurement without contacting the turbid media.

The mode described above can solve also the following conventional problems.

In a conventional apparatus, since a light irradiation device and a light detection device are integrally configured, the distance between an irradiation position and a detection position is fixed. Accordingly, a detection cannot be performed at a position away from the irradiation position at an arbitrary distance.

Further, a back-scattered light to be measured passes via a deepest portion at an intermediate position between the irradiation position and the detection position. That is, information in a deepest portion of information to be observed is obtained at the intermediate point between the irradiation position and the detection position. In the apparatus disclosed in Jpn. Pat. Appln. KOKAI Publication No. 2007-20735 in which the detection devices are disposed at the positions sequentially away from the light irradiation device, a position of a deepest portion to be measured in x, y directions is made farther from the irradiation position as the distances between the light irradiation device and the detection device become longer. Accordingly, the apparatus has a problem in that information whose depth (a z-direction) is changed at a specific position cannot be obtained.

These problems can be solved also by the modes described above.

Further, the modes described above solve these problems and can arbitrarily analyze data positioned in a desired distance from the irradiation position by detecting the back-scattered light. Accordingly, the modes can easily obtain information at a desired position and in a desired depth.

Further, since the modes can simply obtain a lot of information in a short time by moving the irradiation position, the modes can easily create a tomographic image.

With these modes, there can be provided a method and an inside observation apparatus which can analyze information as to an object positioned in a desired distance from an irradiation position.

As a result, there can be provided a method and apparatus which can observe an inside of a living body better than a conventional method and apparatus.

<Third Aspect>

The invention relates further to an apparatus and method which observe an inside of a turbid media by measuring a back-scattered light scattered by a turbid media. One or more modes of a third aspect of the invention explained below may be used in combination with one or more modes of the first aspect and/or the second aspect described above. Further, one mode shown in the third aspect may be independently used or one or more modes shown in the third aspect may be used in combination.

In the third aspect, the turbid media means a body mainly comprising a scattering medium, and a living body is exemplified as an example. The scattering medium exhibits a property for scattering at least a light and mainly scatters the light than absorbs the light.

The turbid media inside observation apparatus of the third aspect is an apparatus for observing a heterogeneous portion existing in a scattering medium in an inside of the turbid media. In the third aspect, the heterogeneous portion is a portion whose optical characteristics such as a transmittance, a refraction index, a reflectance, a scattering coefficient, an absorption coefficient, and the like are different from the optical characteristics of the scattering medium. A blood vessel may be exemplified as an example of the heterogeneous portion, the heterogeneous portion is not limited thereto.

An embodiment of the third aspect will be explained below according to the drawings.

(Fifth Embodiment)

FIG. 20 is a block configuration view of a turbid media inside observation apparatus 2001 according to an embodiment of the third aspect. As shown in the drawing, the turbid media inside observation apparatus 2001 includes a light irradiation device 2010, a detection device 2011, a control device 2012, a display device 2014, and an input device 2015.

The light irradiation device 2010 is an lighting means for irradiating a light including at least a wavelength having optical characteristics, which are different in a heterogeneous portion 2007 in an inside of a turbid media 2008 and in a scattering medium 2006 in the periphery of the scattering medium 2006. Although an LD and the like can be used as the light irradiation device, the light irradiation device is not limited thereto. A light including at least a wavelength, which is absorbed by, for example, a heterogeneous portion but is not absorbed by a scattering medium, may be used as a light irradiated from the light irradiation device 2010. When, for example, a heterogeneous substance having different scattering characteristics in a living body is a blood vessel, a light, which includes a wavelength of a near infrared region having an absorption in hemoglobin, is preferably used as the light including at least the wavelength having the different optical characteristics. The light irradiation device 2010 irradiates a light to the turbid media 2008 based on a control signal from the control device 2012.

The detection device 2011 detects an intensity of a back-scattered light of a light irradiated by the light irradiation device 2010 after the light is reflected, scattered, and absorbed by the scattering medium 2006 of the turbid media 2008 and by the heterogeneous portion 2007 and outgoes from a surface of the turbid media 2008. The detection device 2011 detects the back-scattered light based on a control from the control device 2012.

The control device 2012 includes an imaging device 2016, which controls operations of the light irradiation device 2010 and the detection device 2011 as well as analyzes the data detected by the detection device 2011 and creates a plurality of tomographic images each having a different depth, and an analysis device 2017 which selects a tomographic image in which the heterogeneous portion is shown from the created tomographic images. The tomographic image selected by the analysis device can be displayed by the display device 2014.

The light irradiation device 2010, the detection device 2011, the display device 2014, and the input device 2015 are connected to the control device 2012 by a signal circuit via which an electric signal is transmitted.

Next, an operation of the turbid media inside observation apparatus 2001 according to the embodiment will be explained.

First, a light is irradiated to the turbid media 2008 by the light irradiation device 2010. Next, the intensity of the back-scattered light, which is reflected, scattered, and absorbed by the scattering medium 2006 in the inside of the turbid media 2008 and returns onto the surface of the turbid media again, is detected by the detection device 2011.

Next, the imaging device 2016 analyzes the obtained data and creates tomographic images having different depths, respectively. A principle for creating tomographic image will be explained.

A part (a) of FIG. 21 is a schematic view of a hard mirror 2100 to which the turbid media inside observation apparatus 2100 of the third aspect is applied. The hard mirror 2100 includes an illumination device 2102 and a detection device 2101 and further includes a control device and a display device which are not shown. A part (b) of FIG. 21 shows a schematic cross sectional view of the turbid media, and a part (c) of FIG. 21 is a schematic view when a surface of a turbid media is observed from upward. In the part (c) of FIG. 21, a position at which a light is irradiated from a light irradiation device 2102 onto the turbid media 2108 is shown by a cross mark, and a detection region 2050 in which a back-scattered light is detected by the detection device 2101 is shown by dotted lines.

A back-scattered light of the light irradiated from the light irradiation device 2102 onto the turbid media 2108 is transmitted as shown in the part (b) of FIG. 21. When the back-scattered light is observed from the surface of the turbid media surface, the back-scattered light is formed in a state of concentric circles about the irradiation position as shown in the part (c) of FIG. 21. A concentric circle having a larger diameter shows a back-scattered light passing via a deeper portion of the turbid media. For example, as shown by ring-like regions of reference numerals 2151, 2152, and 2153, concentric regions show back-scattered lights passing via approximately same depths. When light intensity data is extracted in a concentric region, a tomographic image in the depth of the light can be created.

Further, since the distance from the irradiation position to a concentric region corresponds to a depth, a tomographic image of a desired depth can be obtained by changing the distance from the irradiation position to the concentric region.

Further, in a turbid media inside observation apparatus having an illumination device, which can be scanned, in one mode of the third aspect, an illumination point is moved in a detection range 2250 as shown in FIG. 22. At the time, as the illumination point moves, a region in a concentric circle also moves. Accordingly, when light intensity data in a concentric region having a predetermined distance from the illumination point is extracted at all times, information of the same depth can be obtained. This will be explained referring to parts (a) and (a') of FIG. 23A and parts (b) and (c) of FIG. 23B.

Figure 23A:
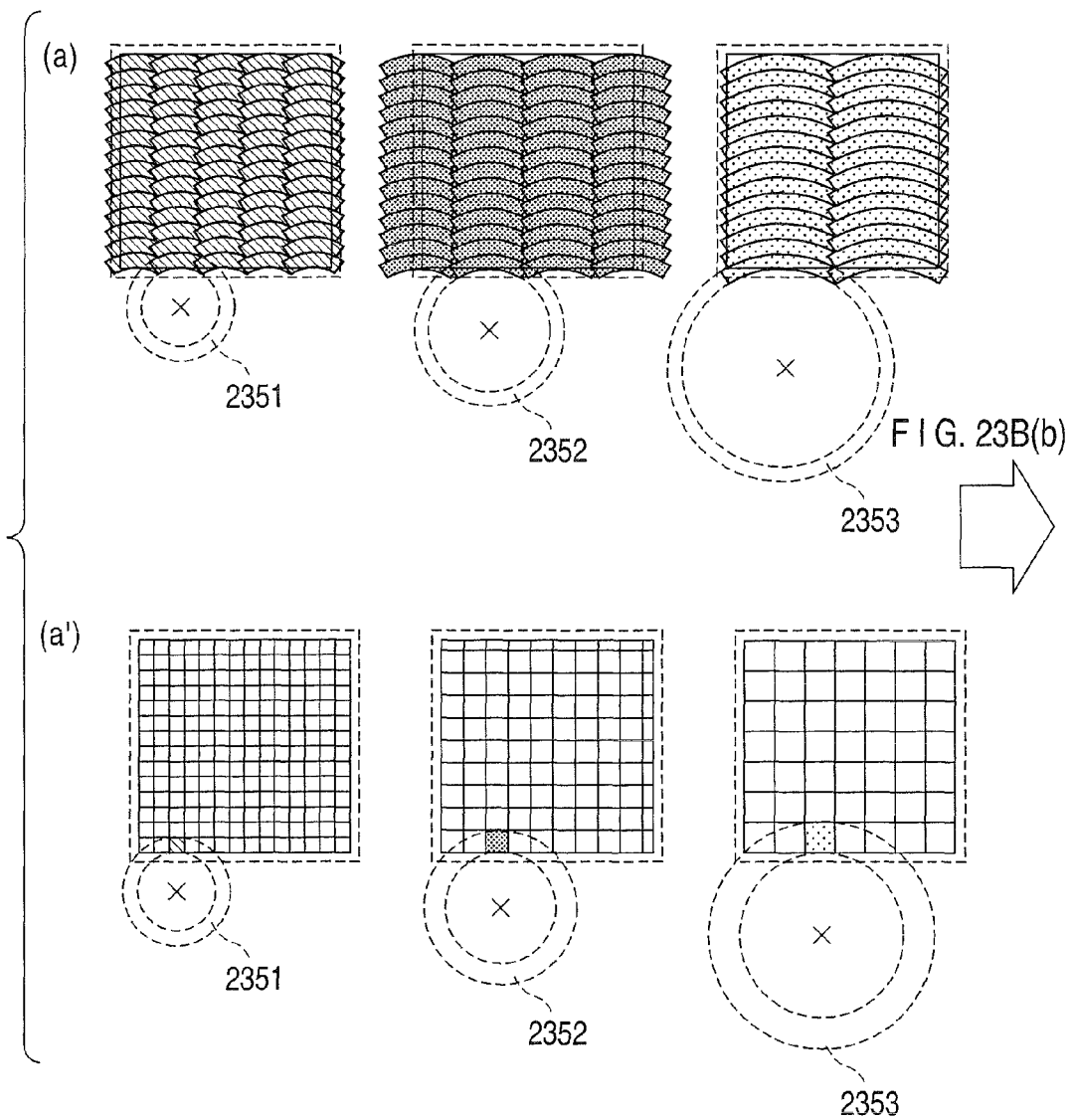
FIG. 23A is a schematic view showing loci of an equi-depth region obtained by scanning an irradiation position.

The parts (a) and (a') of FIG. 23A are views showing that the regions, which are included in the concentric regions 2351, 2352, and 2353 at respective scanning points, are overlapped. In other words, the parts (a) and (a') of FIG. 23A are views showing loci when the concentric regions 2351, 2352 and 2353 are partly moved, respectively. The portions of the concentric regions may be partitioned in any shape. The respective concentric regions have information of the same depths. Accordingly, when a plurality of results of detection are overlapped as shown in the part (a) of FIG. 23A, a tomographic image in the depth can be created as shown in the part (b) of FIG. 23B.

Note that, when data are overlapped, although overlapped data are made, it is sufficient to selectively use arbitrary data from the overlapped data or to use an average value of the overlapped data.

As shown in FIG. 22, FIG. 23A, and FIG. 23B, when an illumination is scanned and detected, a lot of light intensity data can be obtained, and thus a tomographic image having higher accuracy can be obtained.

When a plurality of tomographic images each having a different depth are created based on the principle explained above, next, the analysis device 2017 selects a tomographic image in which the heterogeneous portion is displayed as shown in, for example, the part (c) of FIG. 23B. The selection is performed by determining a tomographic image which satisfies a predetermined contrast condition.

The part (a) of FIG. 23A shows an example in which regions, which are prescribed by the portions corresponding to partial arcs of the respective concentric regions, are employed as light receiving regions. The part (a') of FIG. 23A shows an example in which regions, which are prescribed by the portions corresponding to partial arcs of the respective concentric regions and further prescribed by a part of the regions, for example, by an approximately square shape, are employed as light receiving regions.

When a heterogeneous portion exists in a tomographic image, a light intensity changes in an image. That is, the image becomes heterogeneous and a contrast is generated. At the time, a condition for determining that the contrast is generated on a screen is called "a contrast condition". The analysis device 2017 determines whether or not the respective tomographic images satisfy the contrast condition and determines that the tomographic images which satisfy the contrast condition are tomographic images in which the heterogeneous portion exists.

Although the following methods (1) to (4) may be used as a method of determining whether or not a tomographic image satisfies the contrast condition, the determination method is not limited to the methods (1) to (4) and various methods may be used.

(1) A screen of a tomographic image is divided to some segments and average intensities of the segments are calculated. Next, it is determined whether or not a predetermined difference exists in the average intensities of the segments. In the case, a condition which regards that a difference exists is the contrast condition.

(2) The light intensities of respective images in a screen of a tomographic image are compared with each other and it is determined whether or not a predetermined or more difference of light intensity exists among pixels. In the case, a condition which regards that a difference exists is the contrast condition.

(3) Tomographic images having a different depth are compared with each other and portions having a different light intensity are detected. Portions having the same change of intensity among respective tomographic images may be regarded as noise. When a change of light intensity is different among tomographic images, it may be regarded that a heterogeneous portion exists. In the case, a condition which regards that the change of light intensity is different among the tomographic images is the contrast condition.

(4) A spatial light intensity distribution data image is created from obtained light intensity data, and a change of light intensity is examined. For example, a portion, in which a light intensity largely reduces on a line passing via an arbitrary point on an image, may be regarded as a heterogeneous portion. Further, a portion, in which a degree of reduction of light intensity is small, may be determined as noise.

When a tomographic image, in which a heterogeneous portion is displayed, is selected by any of the methods explained above, the tomographic image is displayed by the display device 2014. At the time, only the selected tomographic image may be displayed or the select tomographic image may be displayed together with other tomographic images with the select tomographic image displayed larger than the other images.

Note that a series of the steps described above are repeatedly and continuously performed while a turbid media is observed, and the displayed tomographic image is sequentially updated.

As described above, according to the mode of the third aspect, a tomographic image of an arbitrary depth can be easily obtained by obtaining light intensity data by operating the light irradiation device 2010 and the detection device 2011 and further an inside of a turbid media can be observed simply and efficiently by automatically selecting a tomographic image in a depth in which a heterogeneous portion exists.

Next, other mode of the third aspect will be explained. A turbid media inside observation apparatus in the mode has such a configuration that a plurality of tomographic images created by an imaging device are displayed and a user can select a desired tomographic image.

The turbid media inside observation apparatus in the mode comprises an illumination device configured to irradiate a light including at least a wavelength having optical characteristics, which are different in a scattering medium configuring the turbid media and in the heterogeneous portion, to the turbid media, a detection device configured to detect a back-scattered light of the light irradiated by the illumination device and to obtain light intensity data of the back-scattered light, an imaging device configured to analyze the obtained light intensity data and to create a plurality of tomographic images each having a different depth, a display device configured to display the created tomographic images, and an input device configured to select a desired tomographic image from the displayed tomographic images and to display the selected desired tomographic image. The illumination device and the detection device used in the mode are the same as those used in the turbid media inside observation apparatus 2001.

The display device can display the tomographic images created by the imaging device at the same time, further can display a tomographic image selected by the user in enlargement or can display only the selected tomographic image in enlargement. For example, although a monitor screen and the like are preferably used as the display device, the display device is not limited to the monitor screen.

The input device is a device via which the user selects a desired tomographic image from the displayed tomographic images and inputs a result of the selection. Although the input device may be, for example, a keyboard and the like via which an image to be selected is instructed or may be a monitor and the like using a touch panel via which an instruction is made by touching a displayed image or surrounding the displayed image with an input pen, the input device is not limited thereto and various input means can be used.

When the turbid media inside observation apparatus in the mode is used, a light is irradiated to a turbid media by the illumination device, a back-scattered light of the irradiated light is detected by the detection device, and the light intensity data of the back-scattered light is obtained. Next, the obtained light intensity data is analyzed by the imaging device, and a plurality of tomographic images each having a different depth are created.

Next, the created tomographic images are displayed by the display device. All the tomographic images may be displayed at the same time or some tomographic images may be displayed at the same time.

Next, the user selects a desired image from the displayed tomographic images and inputs a result of the selection using the input device. The display device displays the selected tomographic image based on an input instruction.

A series of the steps described above are repeatedly and continuously performed while a turbid media is observed, and a displayed tomographic image is sequentially updated. Although the user may periodically select the tomographic images, the condition of the tomographic image selected by the user may be stored and thereafter a tomographic image may be automatically selected according to the condition. The condition of the tomographic image is, for example, a depth and the like.

The turbid media inside observation apparatuses in the respective modes explained above may further include an illumination range recognition device for recognizing the shape of an illumination range to which a light is irradiated by the illumination device and an extraction position determination device for determining an extraction position of light intensity data for creating a tomographic image based on the shape of the illumination range recognized by the illumination range recognition device.

As described above, according to the third aspect, a tomographic image of a turbid media can be efficiently obtained with high accuracy. Further, since a tomographic image in which a heterogeneous portion exists can be simply selected and displayed, a convenience can be improved in a practical use.

The turbid media inside observation apparatus includes an imaging device which includes an illumination range recognition device (that is, an irradiation range recognition device) for recognizing the shape of an illumination range (that is, an irradiation range) irradiated by the illumination device, and an extraction position determination device for determining an extraction position of light intensity data for creating a tomographic image based on the shape of the illumination range recognized by the illumination range recognition device.

The third aspect is not limited to the embodiment and may be variously modified and changed in a scope which does not depart from the gist of the third aspect. Further, components disclosed in the embodiment may be appropriately combined. For example, some components may be deleted from all the components shown in the embodiment. Further, components in different embodiments may be appropriately combined.

Furthermore, it may be understood that the third aspect is an invention as shown in the following (B1) to (B12).

It may be understood that the third aspect is an invention as shown in the following (B1) to (B14).

(B1) A turbid media inside observation apparatus (that is, a turbid media inside observation apparatus) for obtaining information of a heterogeneous portion (that is, an object to be observed) in an inside of a turbid media comprising:

an illumination device (that is, a light irradiation device) configured to irradiate a light including at least a wavelength having optical characteristics, which are different in a scattering medium configuring the turbid media and in the heterogeneous portion, to the turbid media;

a detection device configured to detect a back-scattered light of the light irradiated by the illumination device and to obtain light intensity data of the back-scattered light;

an imaging device (that is, an image construction device) configured to analyze the obtained light intensity data and to create a plurality of tomographic images each having a different depth;

an analysis device (that is, a selection device) configured to select a tomographic image in which the heterogeneous portion is displayed from the created tomographic images; and a display device configured to display the selected tomographic image.

(B2) A turbid media inside observation method using the turbid media inside observation apparatus of the (B1).

(B3) A turbid media inside observation apparatus for obtaining information of a heterogeneous portion in an inside of a turbid media comprises an illumination device configured to irradiate a light including at least a wavelength having optical characteristics, which are different in a scattering medium configuring the turbid media and in the heterogeneous portion, to the turbid media, a detection device configured to detect a back-scattered light of the light irradiated by the illumination device and to obtain light intensity data of the back-scattered light, an imaging device configured to analyze the obtained light intensity data and to create a plurality of tomographic images each having a different depth, a display device configured to display the created tomographic images, and an input device configured to select a desired tomographic image from the displayed tomographic images and to display the selected desired tomographic image.

(B4) A turbid media inside observation method using the turbid media inside observation apparatus of the (B3).

(B5) The turbid media inside observation apparatus according to the (B2 or B4) further comprising an imaging device which comprises an illumination range recognition device (that is, an irradiation range recognition device) configured to recognize a shape of an illumination range (that is, an irradiation range) irradiated by the illumination device and an extraction position determination device configured to determine an extraction position of light intensity data for creating a tomographic image based on the shape of the illumination range recognized by the illumination range recognition device.

(B6) A turbid media inside observation apparatus for obtaining information of a heterogeneous portion (that is, an object to be observed) in an inside of a turbid media comprising:

an illumination device (that is, a light irradiation device) configured to irradiate a light including at least a wavelength having optical characteristics, which are different in a scattering medium configuring the turbid media and in the heterogeneous portion, to the turbid media;

a detection device configured to detect a back-scattered light of the light irradiated by the illumination device and to obtain light intensity data of the back-scattered light;

an imaging device (that is, an image construction device) configured to analyze the obtained light intensity data and to create a plurality of tomographic images each having a different depth;

an analysis device (that is, a selection device) configured to select a tomographic image in which the heterogeneous portion is displayed from the created tomographic images; and a display device configured to display the selected tomographic image.

(B7) The turbid media inside observation apparatus according to the (B6) in which a tomographic image, in which the heterogeneous portion is displayed, is a tomographic image which satisfies a predetermined contrast condition.

(B8) A turbid media inside observation apparatus for obtaining information of a heterogeneous portion in an inside of a turbid media comprising:

an illumination device configured to irradiate a light including at least a wavelength having optical characteristics, which are different in a scattering medium configuring the turbid media and in the heterogeneous portion, to the turbid media;

a detection device configured to detect a back-scattered light of the light irradiated by the illumination device and to obtain light intensity data of the back-scattered light;

an imaging device configured to analyze the obtained light intensity data and to create a plurality of tomographic images each having a different depth;

a display device configured to display the created tomographic images; and an input device configured to select a desired tomographic image from the displayed tomographic images and to display the selected desired tomographic image.

(B9) The turbid media inside observation apparatus according to any one of the (B6) to the (B8) in which a light including at least the wavelength having the different optical characteristics is a light which includes a wavelength of a near infrared region having an absorption in hemoglobin.

(B10) A turbid media inside observation method of observing a heterogeneous portion in an inside of a turbid media comprises:

(a) a step of irradiating a light including at least a wavelength having optical characteristics, which are different in a scattering medium configuring the turbid media and in the heterogeneous portion, to the turbid media;

(b) a step of detecting a back-scattered light of the irradiated light and obtaining light intensity data of the back-scattered light;

(c) a step of analyzing the light intensity data obtained by the step and creating a plurality of tomographic images each having a different depth;

(d) a step of selecting a tomographic image in which the heterogeneous portion is displayed from the created tomographic images; and (e) a step of displaying the tomographic image selected by the step.

(B11) A method according to the (B10) characterized in that the step (d) includes a step of determining whether or not a created tomographic image satisfies a predetermined contrast condition and selects a tomographic image, which satisfies the predetermined contrast condition, as a tomographic image in which a heterogeneous portion is displayed.

(B12) A method according to the (B10) or the (B11) characterized in that the steps (a) to (e) are repeatedly performed and a displayed tomographic image is updated.

(B13) A turbid media inside observation method of observing a heterogeneous portion in an inside of a turbid media comprises:

(a) a step of irradiating a light including at least a wavelength having optical characteristics, which are different in a scattering medium configuring the turbid media and in the heterogeneous portion, to the turbid media;

(b) a step of detecting a back-scattered light of the irradiated light and obtaining light intensity data of the back-scattered light;

(c) a step of analyzing the light intensity data obtained by the step and creating a plurality of tomographic images each having a different depth;

(d) a step of displaying the created tomographic images; and (e) a step of selecting a desired image from the displayed tomographic images and displaying the selected desired image.

(B14) The method according to (B13) characterized in that:

the steps (a) to (d) are repeatedly performed; and a tomographic image having the same condition as the tomographic image selected by the step (e) is selected and a display is updated.

According to the third aspect described above, the following conventional problems may be solved.

In the conventional apparatus, since the light irradiation device and the light detection device are integrally configured, the distance between the irradiation position and the detection position is fixed. Accordingly, since a depth which can be observed is determined, a problem arises in that a tomographic image can be created only in a predetermined depth.

Further, to obtain a tomographic image, since a measurement must be performed at many measurement points, a long time is necessary to obtain a tomographic image.

These problems can be also solved by the third aspect of the invention.

According to the aspect, a method and turbid media inside observation apparatus, which can efficiently obtain a tomographic image in a depth in which a heterogeneous portion exists, can be provided.

Accordingly, a method and apparatus, which can observe an inside of a living body better than the conventional method and apparatus, can be provided by the mode.

<Fourth Aspect>

In a fourth aspect according to the invention, there is provided a turbid media inside observation apparatus which has a function for removing a noise generated from a vicinity of a surface layer of a turbid media. One or more modes of the fourth aspect of the invention explained below may be used in combination with one or more modes of the first aspect, the second aspect and/or the third aspect described above. Further, one mode shown in the fourth aspect may be independently used or one or more modes may be used in combination.

(Sixth Embodiment)

A turbid media inside observation apparatus in the mode creates a deep-portion-processed image in which a noise in the vicinity of a surface and a surface layer of a turbid media is removed. A back-scattered light detected by a detection device includes also a reflected light reflected from the surface of the turbid media. Since minute irregularities exist on the surface of the turbid media, the reflected light is scattered and made strong and weak and may become a noise when a tomographic image is created. Further, since the detected back-scattered light includes also a back-scattered light from a relatively shallow depth, when a tomographic image is created by a back-scattered light from a deep portion, the back-scattered light from the relatively shallow depth also becomes noise.

To cope with the problem, the turbid media inside observation apparatus in the mode can provide a tomographic image from which a noise is removed.

The tomographic image from which the noise is removed can be created by any of the following methods (1) to (3).

(1) A surface layer tomographic image and a deep portion tomographic image are independently created, and the surface layer tomographic image is subtracted from the deep portion tomographic image. The surface layer tomographic image is a tomographic image which is created from a back-scattered light from a relatively shallow portion of a turbid media and from a reflected light from a surface of the turbid media. In contrast, although the deep portion tomographic image is a tomographic image of a desired depth, the deep portion tomographic image includes also a back-scattered light from the surface layer.

Figure 24:
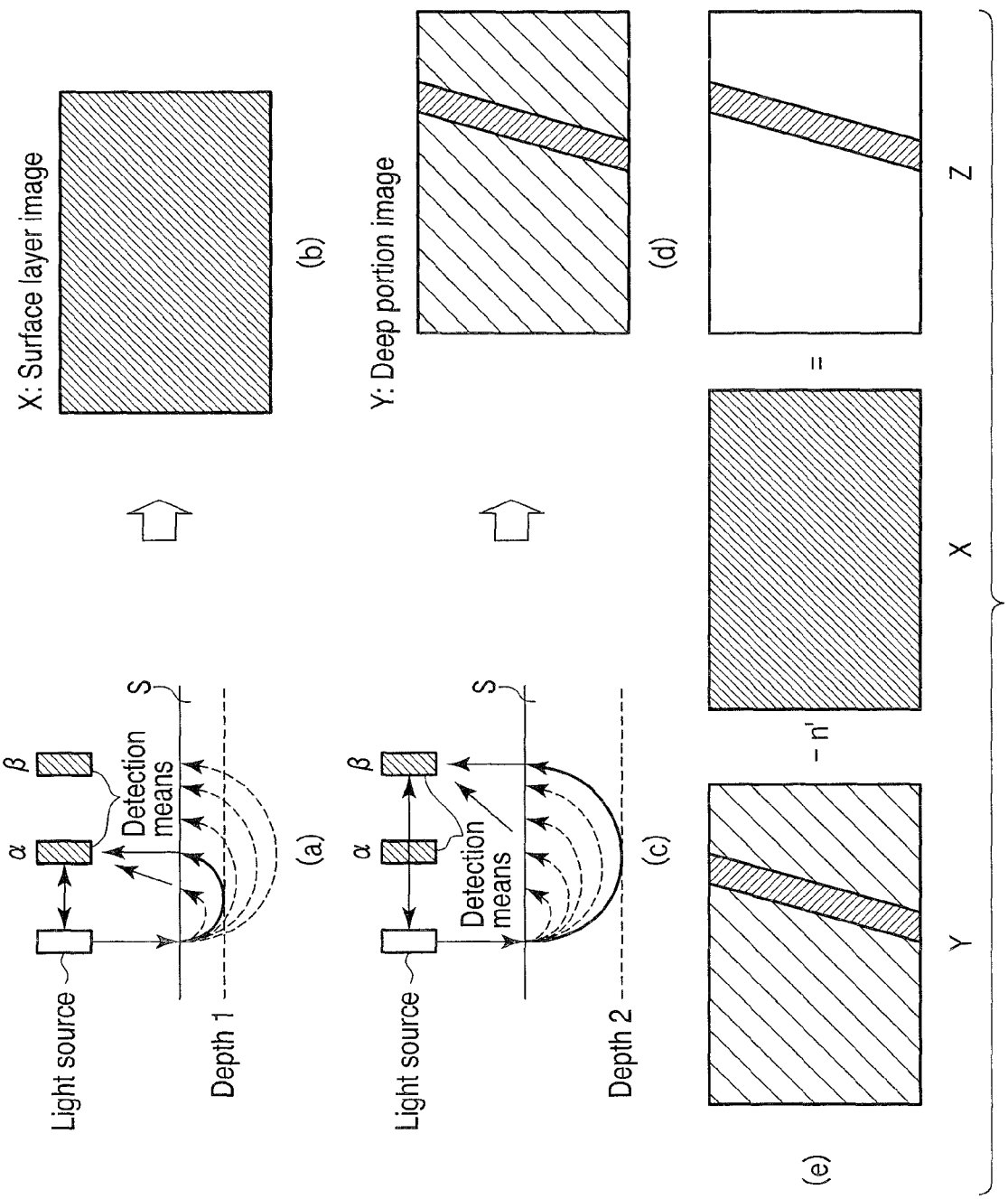
FIG. 24 is a conceptual view showing a first method of noise removing methods.

To independently create the surface layer tomographic image and the deep portion tomographic image, the method changes the distance between an illumination device and a detection device as shown in the parts (a), (b), (c), (d), and (e) of FIG. 24. When the surface layer tomographic image is created, the back-scattered light is detected at a position a as shown in the part (a) of FIG. 24. Thus, a surface layer tomographic image X as shown in the part (b) of FIG. 24 can be obtained. Further, when the deep portion tomographic image is created, the back-scattered light is detected at a position p as shown in the part (c) of FIG. 24. Thus, a deep portion tomographic image Y can be obtained as shown in the part (d) of FIG. 24.

Note that in the parts (a) and (c) of FIG. 24, although the distance between the illumination device and the detection device is changed for the purpose of explanation, the fourth aspect is not limited thereto. That is, the respective tomographic images can be more simply obtained by making the distance of a point at which data for creating the surface layer tomographic image is extract shorter than the distance of a point at which data for creating the deep portion tomographic image is extract when light intensity data obtained by the detection device is analyzed.

Next, as shown in the part (e) of FIG. 24, the surface layer tomographic image X is subtracted from the deep portion tomographic image Y. With the operation, a deep-portion-processed image Z from which a noise of the surface layer is removed can be obtained. Note that since the surface layer tomographic image X has a light intensity larger than the deep portion tomographic image Y, the light intensity is adjusted by multiplying the surface layer tomographic image X by a constant n. It is sufficient to determine the constant n so that the light intensities of the surface layer tomographic image X and the deep portion tomographic image Y have an approximately same average value.

As a calculation method, the tomographic image can be calculated by, for example, calculating a light intensity of each of the pixels on a created image. Further, although the tomographic image may be calculated by calculating an average value of the light intensities of the pixels and using the average value, the calculation method is not restricted thereto and an appropriate method can be selected.

(2) A surface layer tomographic image and a deep portion tomographic image are independently created likewise the method of the (1). In the method, a light having a different wavelength is used as an illumination to create the respective tomographic images. As shown in, for example, a portion (a) of FIG. 25, when a surface layer tomographic image is created, a light source 1 for irradiating a light having a wavelength λ1 is used. Thus, a surface layer tomographic image X as shown in a part (b) of FIG. 25 can be obtained. Further, when a deep portion tomographic image is created, a light source 2 for irradiating a light having a wavelength λ2 is used as shown in a part (c) of FIG. 25. Thus, a deep portion tomographic image Y as shown in a part (d) of FIG. 25 can be obtained. When the surface layer tomographic image is created, a light which scatters more strongly, that is, a light having a short wavelength is used. On the contrary, when the deep portion tomographic image is created, a light which scatters more weakly is used.

Next, as shown in a part of (e) of FIG. 25, the surface layer tomographic image X is subtracted from the deep portion tomographic image Y. A calculation method of the tomographic image is the same as the method (1). As a result, a tomographic image Z from which a noise of a surface layer is removed can be obtained.

Figure 26:
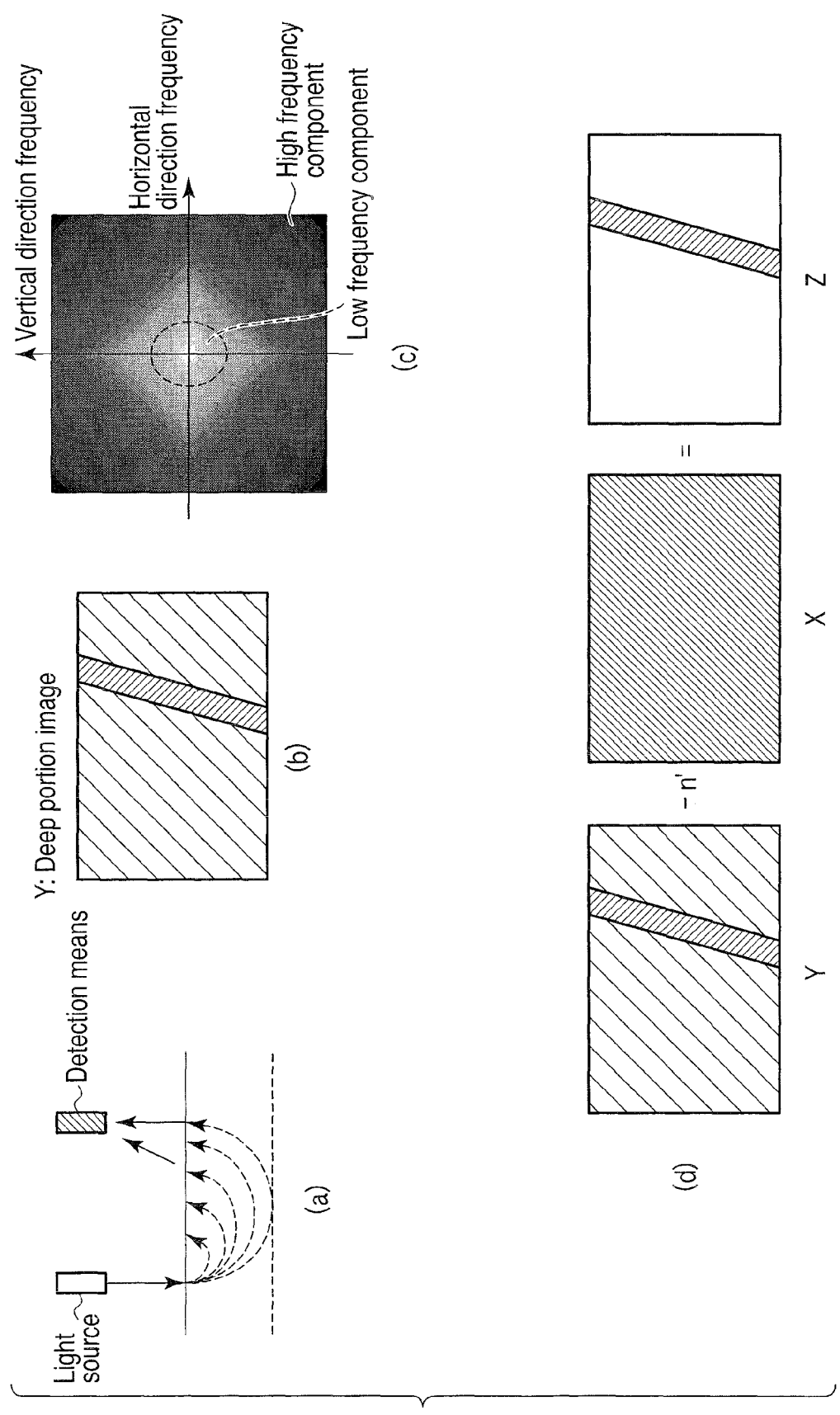
FIG. 26 is a conceptual view showing a third method of noise removing methods.

(3) A back-scattered light is detected in an ordinary manner as shown in a part (a) of FIG. 26, and a deep portion tomographic image Y as shown in a part (b) of FIG. 26 is created. When the deep portion tomographic image Y is subjected to two-dimensional Fourier transformation, an image as shown in a part (c) of FIG. 26 can be obtained in which a horizontal direction frequency of the deep portion tomographic image Y is shown on a horizontal axis, a vertical direction frequency of the deep portion tomographic image Y is shown on a vertical axis, and an amplitude spectrum after the Fourier transformation is shown as a brightness value. Note that the frequency used here means a frequency on an image and calls also a space frequency.

In the image shown in the part (c) of FIG. 26, the low frequency component of a space frequency of the deep portion tomographic image Y corresponds to a center portion of the image shown in the part (c) of FIG. 26, and the high frequency component thereof corresponds to a peripheral portion of the image shown in the part (c) of FIG. 26. In the image, a high frequency portion corresponds to a noise component obtained from a surface and a surface layer of a turbid media. On the contrary, a low frequency portion corresponds to a signal component obtained from a deep portion of the turbid media.

In the image after the Fourier transformation, the deep-portion-processed image Z from which a noise is removed can be obtained by selecting only the low frequency portion and subjecting the low frequency portion to inverted Fourier transformation.

Otherwise, as shown in a part (d) FIG. 26, the deep-portion-processed image Z can be also obtained by subtracting the surface layer tomographic image X, which is obtained by subjecting the high frequency component to the inverted Fourier transformation, from the deep portion tomographic image Y.

Note that a threshold value which separates a high frequency from a low frequency may be appropriately set by the size and the position of a heterogeneous portion to be observed.

The methods explained above can be executed by the turbid media inside observation apparatuses according to the first to fourth embodiments. For example, the deep portion tomographic image and the surface layer tomographic image can be created by an image processing device, and the respective calculations can be performed by an analysis/processing device.

Otherwise, a control device including an imaging device and a calculation device may be provided, and a configuration of the control device may be appropriately selected.

The fourth aspect is not limited to the embodiments and may be variously modified and changed in a scope which does not depart from the gist of the fourth aspect. Further, components disclosed in the embodiments may be appropriately combined. For example, some components may be deleted from all the components shown in the embodiments. Further, components in different embodiments may be appropriately combined.

According to the above explanation, it may be understood that the fourth aspect is an invention expressed in the following (C1) to (C4).

(C1) A turbid media inside observation method of observing a heterogeneous portion in an inside of a turbid media comprises:

a step of irradiating a light including at least a wavelength having optical characteristics, which are different in a scattering medium configuring the turbid media and in the heterogeneous portion, to the turbid media;

a step of detecting a back-scattered light of the irradiated light and obtaining light intensity data of the back-scattered light;

a step of analyzing the light intensity data obtained by the step and determining a detection region on a surface of the turbid media;

a step of detecting a back-scattered light in the detection region determined by the step and obtaining light intensity data; and an image processing step of creating a tomographic image of the turbid media from the light intensity data obtained by the step.

(C2) The method according to (C1) including a step of performing an adjustment so that the determined detection region is included in a detection range in which the back-scattered light is detected.

(C3) The method according to (C2) further including a step of detecting a back-scattered light by causing scanning to be performed while keeping an illumination range, in which a light is irradiated to the turbid media, and the detection range in a predetermined positional relation on a surface of the turbid media and obtaining the light intensity data.

(C4) The method according to any one of the (C1) to the (C3) characterized in that a step of determining the detection region is automatically performed.

The method and apparatus according to the fourth aspect can be used as a method of and/or an apparatus for observing a living body, and in particular, can be used in an endoscope, a hard mirror, and the like.

With the mode, a noise generated from the vicinity of a surface of a turbid media can be removed, thereby it is possible to provide a method and apparatus capable of observing an inside of a living body better than a conventional method and apparatus.

<Fifth Aspect>

According to a fifth aspect, there are provided a method of imaging a back-scattered light well and an apparatus for observing an inside of a living body making use of the imaged back-scattered light.

For example, in the case where a function, which irradiates a light to a point and detects a back-scattered light from a point away from the point at a predetermined distance is mounted on an inside observation apparatus, a light path of an illumination light is not parallel with a light path of a detected light. Accordingly, the distance between an illumination point and a detection point (hereinafter, described as "SD distance") is changed by an observation distance.

A longer observation distance more increases the SD distance, so that a light amount reduces. Accordingly, a ratio of a signal to a noise (hereinafter, described as "SNR") is lowered. Further, a shorter observation distance more reduces the SD distance, so that a surface diffused light increases. Accordingly, a scattered light from an inside of a turbid media is buried and cannot be detected.

According to the fifth aspect, there are provided a method of capable of solving the problem and an apparatus for observing an inside of a living body.

One or more modes of the fifth aspect of the invention explained below may be used in combination with one or more modes of the first aspect, the second aspect, the third aspect and/or the fourth aspect described above. Further, one mode shown in the fifth aspect may be independently used or one or more modes may be used in combination.

A term "object to be picked up" used below may be exchangeably used with terms "an object to be observed" or "an object to be measured". Further, any of the terms may be described as "an object".

First, a basic configuration and an image pick-up method of the inside observation apparatus which can be used in the fifth aspect will be explained.

(Seventh Embodiment)

FIG. 27 shows an inside observation apparatus as an example of a seventh embodiment which can be used in the fifth aspect. FIG. 27 is a block configuration view showing a configuration of the apparatus in its entirety of the embodiment. The observation apparatus includes an input device configured for an operator to input desired information such as a numerical value, a measurement condition, and the like, a light source for irradiating an object to be picked up, an illumination optical system configured to irradiate a light from an irradiation light from the light source to the surface of the object to be picked up via an irradiation port, a detection optical system configured to capture a back-scattered light outgoing from the surface of the object to be picked up, a detector configured to convert the back-scattered light to an electric signal, a scanning mechanism configured to scan an irradiation position and a detection position on the surface of the object to be picked up, a control device configured to control the light source and the scanning mechanism, a measurement device configured to measure an intensity of the electric signal from the detector, an imaging device configured to create an image based on the measured intensity of the electric signal when the scanning is performed, a calculation device configured to calculate a path and contents of adjustment of the scanning, and a display device configured to display the created image.

A light, which is irradiated from the light source is irradiated to onto the object to be picked up from the irradiation port passing via the illumination optical system in response to information input by an operator responding to a desire. At the time, the radiation light is controlled by the scanning mechanism so as to be irradiated to a point and/or a region of a predetermined position of the surface of the object to be picked up. Scanning performed by the scanning mechanism is controlled by the control device. The control by the scanning mechanism is performed by changing the irradiation optical system and/or a position of the irradiation port. A light to be detected from the object to be picked up is captured by a detection port of the detection optical system and sent to the detector passing via the detection optical system. The detection optical system and/or the detection port is scanned by the scanning mechanism controlled by the control device so as to receive a light at a desired position. The light captured by the detection port is sent to the detector passing via the detection optical system and converted to an electric signal in the detector. An intensity of the converted electric signal is measured by the measurement device. The measurement device creates an image from intensities of a plurality of obtained electric signals. Further, the calculation device calculates the path and the contents of adjustment of the scanning.

The input device may be used so that a user selects a desired tomographic image from a plurality of displayed tomographic images and inputs a result of the selection. Although the input device may be, for example, a keyboard and the like via which an image to be selected is instructed or may be a monitor and the like using a touch panel via which an instruction is made by touching a displayed image or surrounding the displayed image with an input pen, the input device is not limited thereto and various input means can be used.

"The light source", "the illumination optical system", and "the irradiation port" may be called "an irradiation device" as a whole. "The detection optical system", "the detection port" and "the detector" may be called "a detection device" as a whole. "The measurement device" may be called "an imaging device" from a view point of creating an image.

The control device, the measurement device, and the calculation device may be independently configured and disposed, respectively, one or more of the control device, the measurement device, and the calculation device may be combined and configured as one unit or all of the control device, the measurement device, and the calculation device may be configured as one unit. Further, the control device may entirely control a conversion from a light to an electric signal in the scanning mechanism and in the detector, a measurement and a creation of image in the measurement device as well as various types of calculation in the calculation device, a plurality of control devices may be disposed to control a part of the operations, or control devices may be plurally disposed so as to correspond to the operations.

The light source is connected to the illumination optical system. A first scanning mechanism is configured to scan the illumination optical system in response to an instruction from the control device. Likewise, a second scanning mechanism is configured to scan the detection optical system in response to an instruction from the control device. The detector is configured to be connected to the detection optical system and to detect a back-scattered light incident on the detection optical system.

With the configuration of FIG. 27, the inside observation apparatus permits scanning by operating the optical systems.

Further, the observation apparatus may include a storage device. The storage device can store information such as a look-up table, an image creation program and/or a scanning protocol, and the like. The control device may perform a desired control to a desired component based on and/or referring to the information. Further, the observation apparatus may include a recording device. The recording device may be configured to temporarily store information or to partly and/or entirely store obtained images.

Further, the seventh embodiment may further make use the same configurations and members as the configurations and members described in the first aspect as well as the first embodiment and the second embodiment.

The third aspect is not limited to the embodiment and may be variously modified and changed in a scope which does not depart from the gist of the third aspect. Further, a plurality of components disclosed in the embodiment may be appropriately combined. For example, some components may be deleted from all the components shown in the embodiment. Further, components in different embodiments may be appropriately combined.

(Eighth Embodiment)

FIG. 28 shows an inside observation apparatus as an example of an eighth embodiment which may be used in the fifth aspect. FIG. 28 is a block configuration view showing a configuration of the apparatus in its entirety of the embodiment.

The observation apparatus is configured to perform scanning by directly moving an optical axis by disposing a scanning mechanism in a midpoint of the optical axis. The eighth embodiment is the same as the seventh embodiment described in FIG. 27 except the above point.

Accordingly, the observation apparatus includes a light source, a first light guide optical system configured to guide a light from the light source to an illumination optical system, an illumination optical system configured to receive a light from the first light guide optical system and to irradiate the light onto s surface of an object to be picked up, at least a first scanning mechanism configured to change an optical axis on a light path for guiding a light from the first light guide optical system to the illumination optical system and to scan an irradiated light, a second light guide optical system for guiding a light incident on a detection optical system to a detector, and at least a second scanning mechanism configured to change an optical axis on a light path for guiding a light from the second light guide optical system to the detector and to scan a light to be detected.

(Ninth Embodiment)

FIG. 29 shows an inside observation apparatus as an example of a ninth embodiment which may be used in the fifth aspect. FIG. 29 is a block configuration view showing a configuration of the apparatus in its entirety of the embodiment.

The observation apparatus is the same as the eighth embodiment described in FIG. 28 except that a first scanning mechanism and a second scanning mechanism are configured by one scanning mechanism and an inter-center distance adjustment optical system, which is configured to be connected to a scanning mechanism to adjust the positional relation between an optical axis of an irradiated light and an optical axis of a light to be detected is provided.

The inter-center distance adjustment optical system may be configured independently of the scanning mechanism, and the inter-center distance adjustment optical system and the scanning mechanism may be configured as one unit. Further, the inter-center distance adjustment optical system may be disposed nearer to a light source and to a detector side than the scanning mechanism and may be disposed nearer to an illumination optical system and to a detection optical system side than the scanning mechanism.

<Object to be Picked Up Side Distal End>

FIG. 30 is a view schematically showing an object to be picked up side distal end of observation apparatuses of the seventh embodiment to the ninth embodiment. An irradiation port of an irradiation optical system, which irradiates a light to an object to be picked up, and a detection port of a detection optical system, which receives a light from the object to be picked up, are shown to the object to be picked up side distal end of the observation apparatuses by circles. The distance between the respective centers of the illumination port and the detection port is called an inter-center distance and shown by d1.

Figure 31:
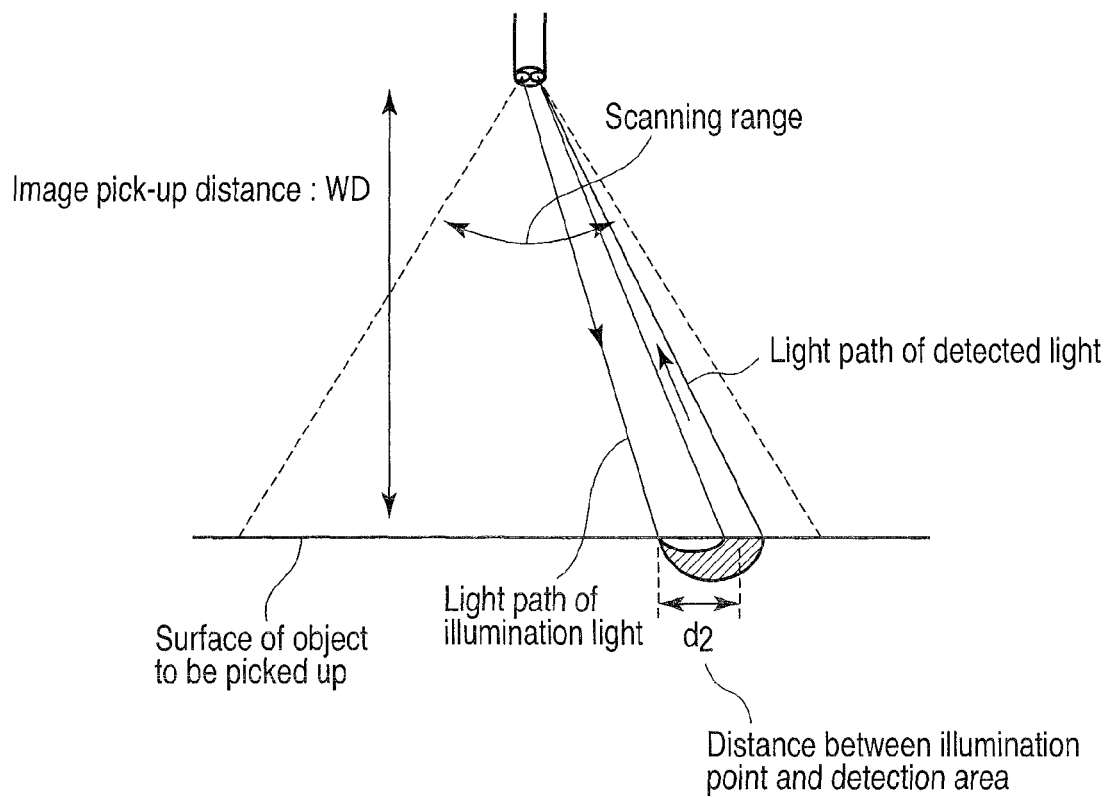
FIG. 31 is a schematic view showing a relation between a distal end of the observation apparatus and an object to be picked up.

FIG. 31 is a view showing a relation among a light irradiated from the observation apparatuses of the seventh embodiment to the ninth embodiment, a light outgoing from the object to be picked up and captured by the detection port included in the detection optical system, and respective portions.

As described above, the inter-center distance between the illumination port and the detection port of the observation apparatuses is shown by d1, and further the distance between the centers of an illumination region and a detection region on a surface of the object to be picked up, that is, an inter-center distance is shown by d2. At the time, since the illumination port is located adjacent to the detection port, d1<d2. The distance from the surface of the object to be picked up to the distal end of the observation apparatuses, that is, to the illumination port and the detection port is an image pick-up distance (WD).

Figure 32A:
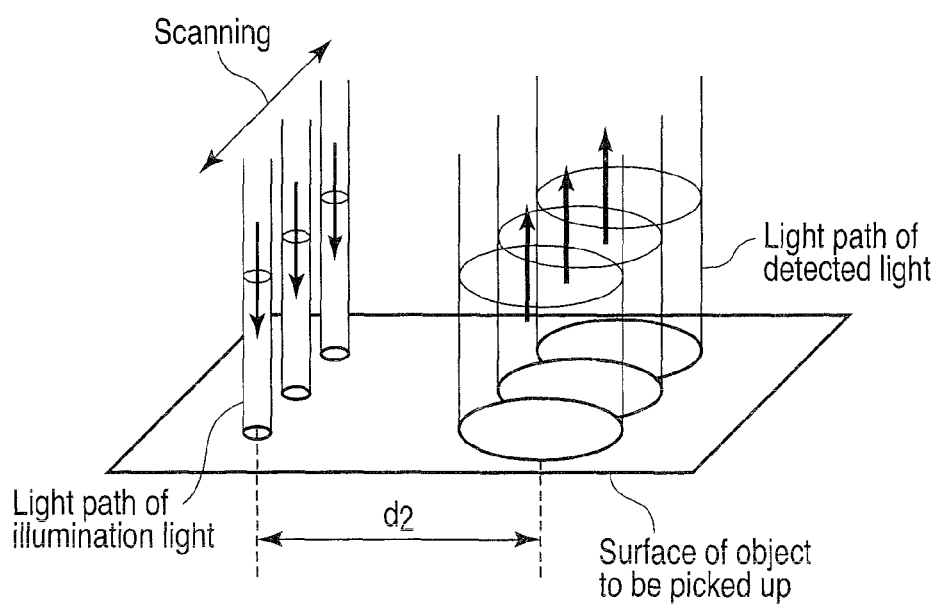
FIG. 32A is a schematic view showing respective light paths, an illumination region, and a detection region.

FIG. 32A is a schematic view when FIG. 31 is observed from obliquely upward as well as a view when the irradiation optical system and the detection optical system are scanned. FIG. 32A schematically shows light paths of respective lights when the irradiation optical system and the detection optical system are scanned, the illumination region and the detection region.

An object to be picked up, which includes a first tissue and a second tissue distributed in the first tissue, can be observed by scanning the irradiation optical system and the detection optical system as described above. That is, a change of light amount depending on presence or absence of the second tissue can be detected as to a region between the illumination region and the detection region. As a result, the distribution of the second tissue in the first tissue can be observed. A two-dimensional distribution of the second living tissue can be detected by performing scanning by adding a scanning device to the illumination device and the detection device while prescribing the distance d2. At the time, a scanning direction is not limited to a linear direction. Further, two or more sets of the illumination region and the detection region may be provided to illuminate and to detect two or more points at the same time. With the configuration, a wider range can be observed. In the case, separate distances between the respective sets may be arbitrarily determined, and the respective sets may be disposed adjacent to each other or may be disposed to an illumination region and/or a detection region which are away from each other.

The observation apparatuses of the seventh embodiment to the ninth embodiment may be further provided with an imaging device. With the configuration, a plurality of electric signals obtained by scanning are imaged in the imaging device. The imaging device can display a two-dimensional distribution as a two-dimensional image by displaying light intensity signals detected at respective scanning points by causing the scanning points to correspond to pixels positions in a displayed image. At the time, the light intensity signals may be displayed by being converted to color shade information or may be displayed by being converted to color information. Further, the observation apparatuses may be provided with an image processing device. With the configuration, a deep portion tomographic image and a surface layer tomographic image may be created and an arbitrary image process may be performed.

FIG. 32A shows a schematic view of motions of the illumination region and the detection region when the illumination region and the detection region are scanned. Pixels of an image configured by the imaging device are disposed according to a disposition of the scanning points. That is, the gaps between adjacent scanning points correspond to the gaps of the pixels.

At the time, when the size of the detection region is made larger than the gaps between the scanning points, intersecting portions may be created between the detection regions at adjacent scanning points. With the configuration, since a light amount between adjacent detection regions changes smoothly, the same noise reduction effect as that when a smoothing process is performed on an image can be obtained.

(Tenth Embodiment)
<Image Pick-Up Method>

An example of a detection method according to the fifth aspect will be explained using a flowchart shown in FIG. 32B.

At S321, an operator turns on an illumination light of an observation apparatus, and a process goes to S322.

At S322, a control device gives an initial value "n=0" to a coordinate n of a detection point, and the process goes to S323.

At S323, the control device reads out a coordinate of an n-th scanning point to be illuminated from a look-up table (hereinafter, described as "LUT") stored in a storage device, and the process goes to S324.

At S324, the control device controls an illumination scanning mechanism based on the coordinate read at S323 and moves and disposes an illumination optical system to the position of the coordinate, and the process goes to S325.

At S325, the control device reads out the coordinate of the n-th scanning point to be detected from the LUT stored in the storage device, and the process goes to S326.

At S326, the control device controls a detection scanning mechanism based on the coordinate read at S325 and moves and disposes a detection optical system to the position of the coordinate, and the process goes to S327.

At S327, the control device irradiates a light from an irradiation port of the illumination optical system disposed to the coordinate and converts a light, which is captured by a detection port of the detection optical system disposed to the coordinate, to an electric signal by a detector, thereby reading out a detection signal as to the n-th scanning point and storing the detection signal in a recording device. The process goes to S328.

At S328, the control device performs a calculation of "n=n+1" as to the coordinate of a detection point, and the process goes to S329.

At S329, the control device determines whether or not the coordinate n of the detection point given at S328 is equal to a terminal value N (n=N), and when the coordinate n is not equal to the terminal value N, the process goes to S323 and moves via a scanning/detection loop until n=N is achieved. When the coordinate n is equal to the terminal value N, the process goes to S330.

At S330, the control device instructs an imaging device to dispose the intensities of the detection signals, which are obtained as to all the coordinates of n=1 to N and stored in the recording device by the control device, to corresponding coordinates so as to create an image, and the process goes to S322.

The image created at S330 may be stored in the recording device and/or may be displayed on a display device.

An illumination position and a detection position to be scanned are held in the storage device and/or in the recording device and the like of the observation apparatus as a LUT which is a series of coordinate data. When scanning is executed, the control device reads out the respective coordinates from the LUT, moves the positions of an illumination device and a detection device by controlling the scanning mechanism and disposes the illumination device and the detection device at desired positions corresponding to the coordinates so as to perform a position control.

The LUT may hold the coordinate data of a position on a surface of an object to be picked up, may hold data of a swing angle between the illumination light and a detected light, or may hold the data of an electric signal (voltage value/current value) used by the scanning mechanism for control. Further, the LUT may separately hold the positional relation (for example, the value d2) between illumination and detection, and a LUT may be used for illumination and the detection.

<Adjustment of Distribution of Observation Distance>

Figure 33:
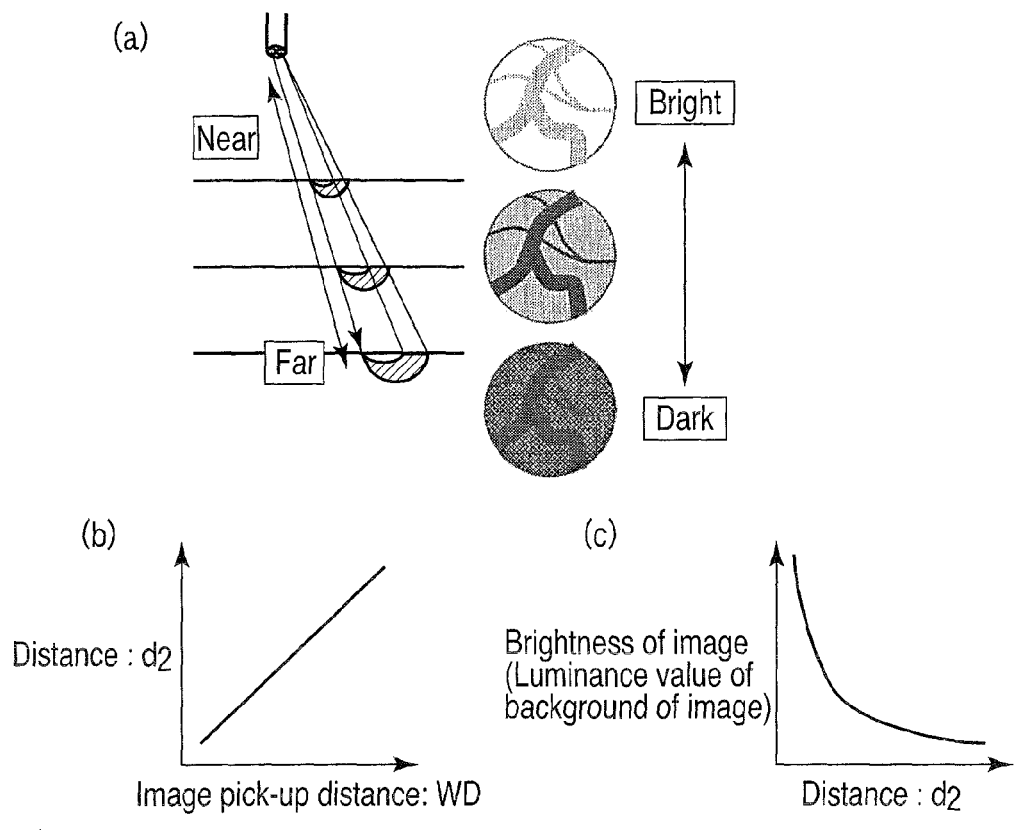
FIG. 33 is a view showing a relation among a distance d2, an image pick-up distance WD, and a brightness of an image.

As described above, in an ordinary observation apparatus, d1<d2 as shown in a part (a) of FIG. 33. Accordingly, a magnitude of d2 changes depending on whether the observation distance (WD) is small (that is, near) or large (that is, far). Accordingly, when the observation distance (WD) between the surface of the object to be picked up and the irradiation port and the detection port is nearer, an image including a background is made brighter, whereas when the distance becomes farther, the image including the background is made darker in its entirety (refer to the right side view of the part (a) of FIG. 33, a part (b) of FIG. 33).

In contrast, the intensity of a back-scattered light is made stronger as the illumination region and the detection region on the surface of the object to be picked up is nearer to each other. Accordingly, when d2 is smaller, a detection intensity becomes larger (refer to a part (c) of FIG. 33).

Accordingly, when the WD is smaller, a detected light amount becomes larger, whereas when the WD is larger, the detected light amount becomes smaller. That is, when an image is observed at a position where the WD is small, the image is made bright, whereas when the image is observed at a position where the WD is large, the image becomes dark.

In an observation of a deep portion, when brightness of an image changes and becomes excessively bright in its entirety, depth information existing in the image is made thin and becomes difficult to be observed. On the contrary, when the image is excessively dark, the depth information is buried in a background image and becomes difficult to be observed.

Figure 34:
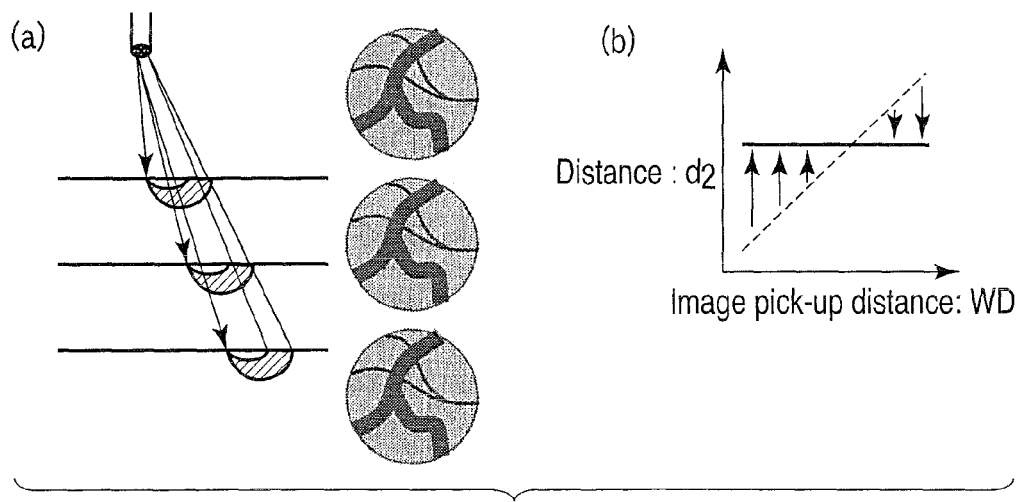
FIG. 34 is a view showing a relation among a distance d2, an image pick-up distance WD, and a brightness of an image.

As shown in a part (a) and a part (b) of FIG. 34, when the illumination position and the detection position are changed so that d2 does not change even if WD changes, an appropriately bright image can be obtained at all times.

Figure 35:
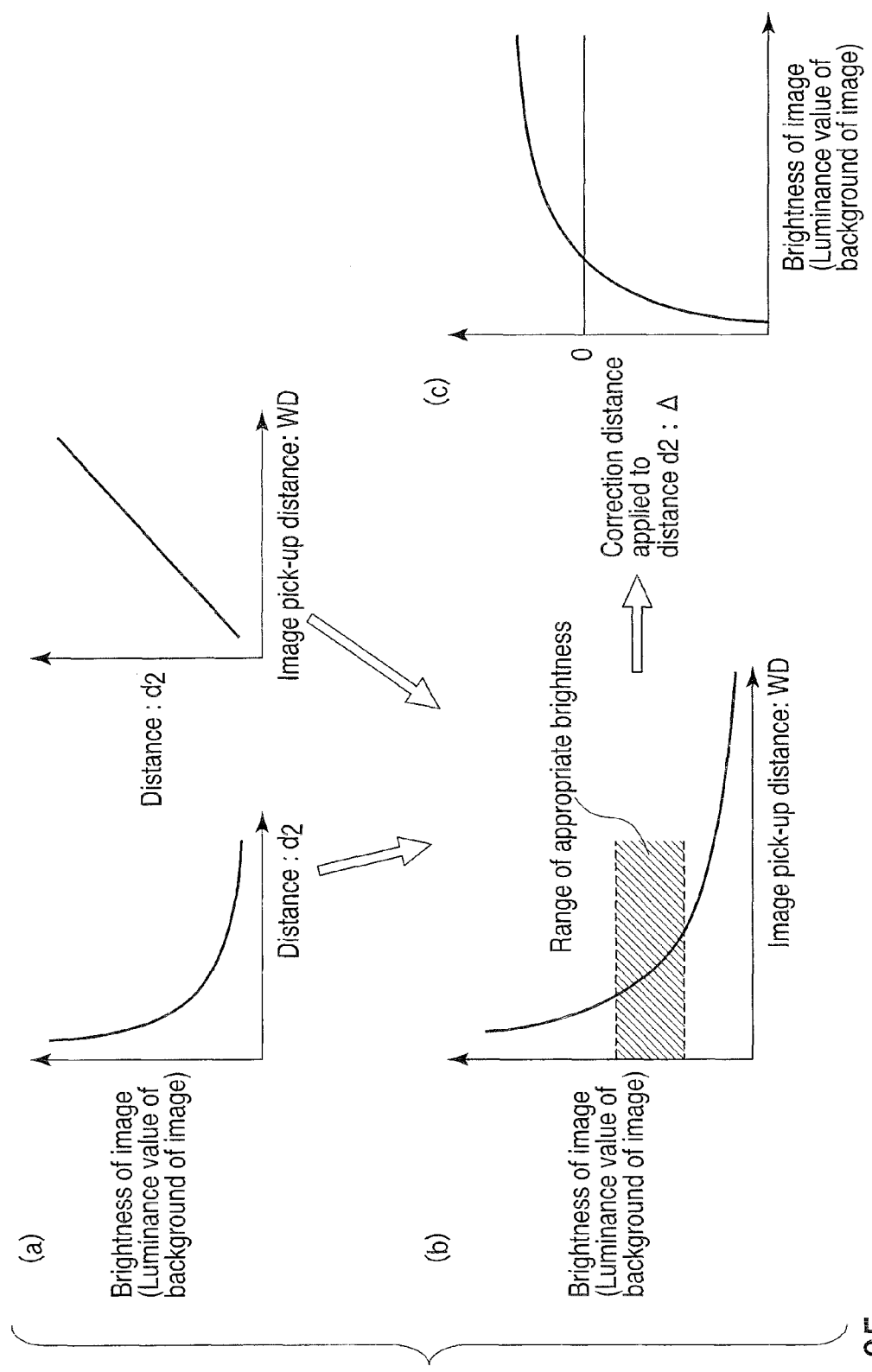
FIG. 35 is a view showing a relation among a distance d2, an image pick-up distance WD, and a brightness of an image.

For example, in order to obtain an appropriate brightness by which a blood vessel can be definitely observed, it is necessary to previously obtain a relation between the distance d2 and the brightness of image experimentally. As shown in parts (a), (b), and (c) of FIG. 35, the image pick-up distance WD can be estimated from the brightness of a screen when the relation between the distance d2 and the image pick-up distance WD (the part (a) of FIG. 35) is also taken into consideration (the part (b) of FIG. 35). Further, a correction value, which is applied to the distance d2 to cause the brightness of the screen fall within an appropriate brightness range, can be also calculated (the part (c) of FIG. 35).

Further, when the inside observation apparatus is used as a scanning type image pick-up apparatus, an observation distance is not fixed even in the same screen and a distribution is generated as to a different distance. Accordingly, it is found that a phenomenon occurs in that deep portion information can be observed in only a part of a screen.

Figure 36:
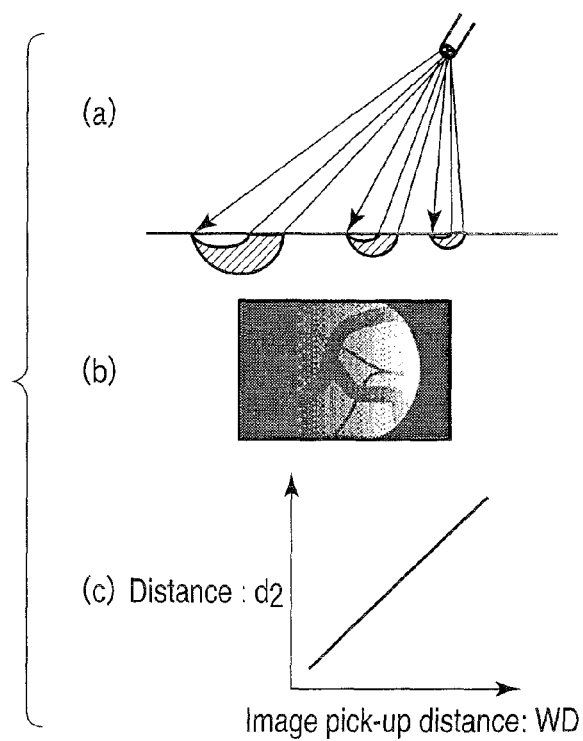
FIG. 36 is a view showing a relation among a distance d2, an image pick-up distance WD, and a brightness of an image.
Figure 37:
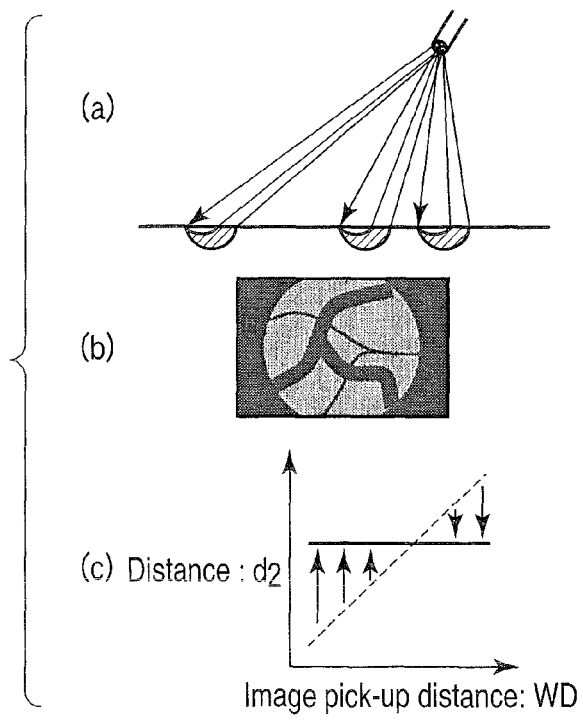
FIG. 37 is a flowchart showing an example of a tenth embodiment.

Parts (a), (b), and (c) of FIG. 36 show an example of the distribution. When the brightness in a screen is uniform, the average value of luminance values of an overall screen can be regarded as the brightness of the screen. However, actually, a brightness is different even in one screen as shown in the (a), (b), and (c) of FIG. 36. That is, even in one screen, there are generated a portion in which the blood vessel is liable to be observed and a portion in which the blood vessel is difficult to be observed. It is found that the state is improved by adjusting the distance d2 at respective image pick-up points in the same screen. It is possible to make the blood vessel to be liable to be observed in the overall screen by the adjustment (parts (a), (b), and (c) of FIG. 37).

(Eleventh Embodiment)

An eleventh embodiment is a method of adjusting the distance d2 at respective image pick-up points in the same screen as described below.

First, an image is picked up. Next, a filtering processing is performed to the image in its entirety. The filtering processing is a processing for erasing an image of a structural member such as a blood vessel and the like existing in an image to obtain only a distribution of detected intensities of a background. For example, it is sufficient to perform the processing using a low-pass filter. Further, it is sufficient to previously experimentally obtain a value according to a structural member of an object to be picked up to be processed as a threshold value of a space frequency for the filtering.

Since a WD at the respective image pick-up points can be calculated from the luminance values at the respective image pick-up points (respective pixels on the image) as a result of the filtering processing, a correction value applied to d2 can be calculated from the WD. Data, which causes the luminance values to correspond to the WD and/or data, which causes the WD to correspond to d2, may be previously stored in the storage device. Further, data, which causes luminance values to correspond to a correction value of d2 may be previously stored in the storage device. The calculation device and/or the control device may perform a desired processing referring to the data.

Finally, the image is picked up again using d2 corrected by the obtained correction value and displayed on the display device.

The method can be performed in the observation apparatuses described in any of the embodiments in any of the aspects. Further, the method is preferably used in combination with the image pick-up method as the tenth embodiment. The method will be explained below referring to some examples. These methods may be used to pick up a still image as well as to pick-up a moving image.

EXAMPLE 1

Figure 38:
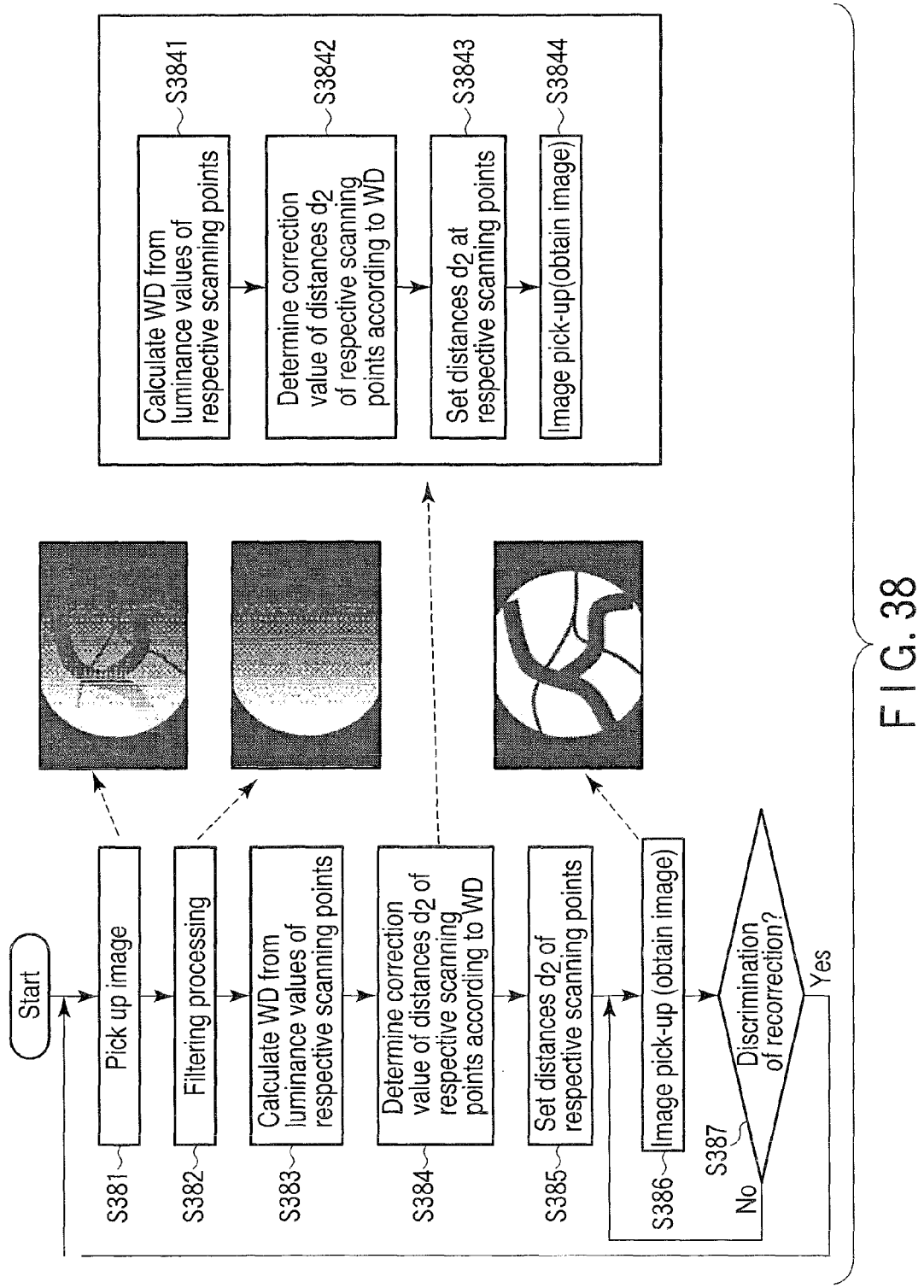
FIG. 38 is a flowchart showing an example of a correction method of performing a filtering processing.

An image pick-up method as an example of the eleventh embodiment will be explained using FIG. 38.

The control device starts an image pick-up in the observation apparatus in response to an instruction of an operator, and a process goes to S381.

Figure 32B:
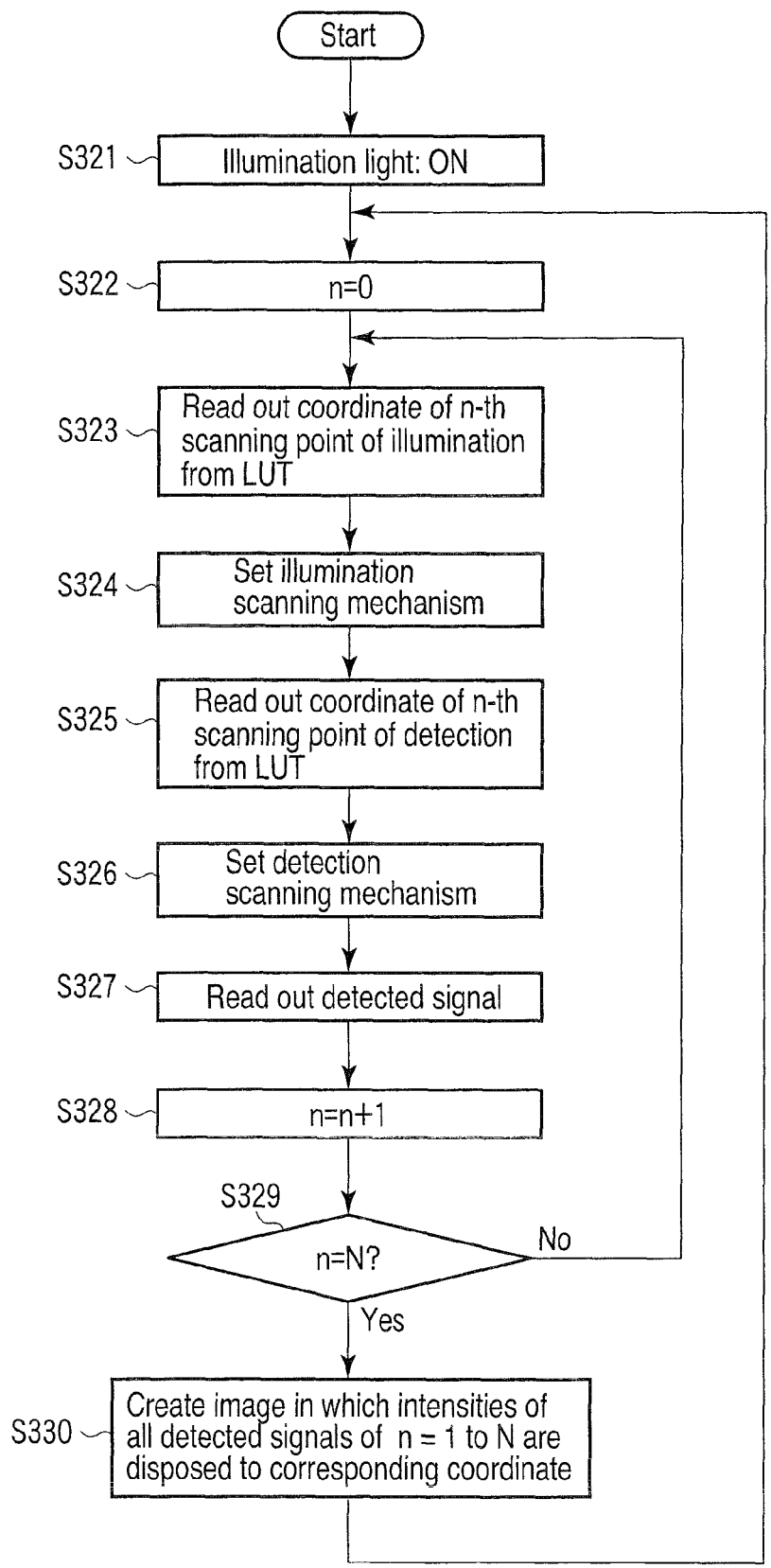
FIG. 32B is a flowchart showing an example of an image pick-up method.

At S381, an image is obtained by repeating S321 to S330 described in FIG. 32B, and the process goes to S382.

At S382, the image processing device applies the filtering processing to the image in its entirety in response to an instruction of the control device, and the process goes to S383.

At S383, in response to an instruction of the control device, the calculation device calculates the WD as to the image in its entirety to which the filtering processing is applied based on the luminance values of respective scanning points, and the process goes to step S384.

At S384, the calculation device determines the correction value of the distances d2 of the scanning points according to the WD, and the process goes to S385.

At S385, the control device receives the correction value from the calculation device and sets the distances d2 at the respective scanning points based on the correction value, and the process goes to S386.

At S386, the control device obtains an image by repeating S321 to S330 described in FIG. 32B in a state where the control device instructs the inter-center distance adjustment optical system and the scanning mechanism to move and dispose the illumination optical system and the detection optical system so that the corrected distances d2 are kept and, and the process goes to S387.

At S387, the control device determines whether or not a recorrection is necessary, and when the recorrection is not necessary, the process goes to S386, whereas when the recorrection is necessary, the process goes to S381 and repeats the respective steps again.

At S386, the control device performs an image pick-up in the state where the control device instructs the inter-center distance adjustment optical system and the scanning mechanism to move and dispose the illumination optical system and the detection optical system so that the corrected distances d2 are kept. Further, the control device causes the display unit to display the obtained image.

When it is not necessary to determine whether or not the recorrection is necessary, it is sufficient that the process goes from S382 to S3841 and executes the steps up to S3844 and that a program is made for the purpose.

Further, examples of the determination of the recorrection are as described below.

(1) Whether or not the recorrection is necessary is determined depending on a length of time which passes from a previous correction time. For example, in the case, it is sufficient for the control device to determine "whether or not 100 ms has passed from the previous correction time". The determination may be executed by, for example, making a program so that the control device resets a timer each time a correction is performed.

(2) Whether or not the recorrection is necessary is determined depending on the number of images picked up after a previous correction. For example, in the case, it is sufficient for the control device to determine "whether or not 10 sheets of images have been picked up after the previous correction". The determination may be executed by, for example, making a program so that the control device resets an image pick-up counter each time a correction is executed.

It is sufficient to determine the correction value of the distances d2 of the respective scanning points according to the WD by, for example, referring to a LUT and the like in which information, which is previously stored in the storage device by the calculation device, for example, the WD is caused to correspond to the correction value, by performing a calculation based on a previously stored calculation expression, by using information, which is obtained by a previous measurement and stored in the recording device, or by combining these processings.

EXAMPLE 2

An example 2 is a modification of the example 1 which is more appropriate when a moving image is picked up. When a moving image is picked up, it is sufficient to perform the filtering processing to obtain an image, to calculate thereby an intensity distribution of background, and to calculate a correction value Δ necessary to the distance d2 from the value of the distribution. At the time, it is also possible to store data, which causes the intensity of the background distribution to correspond to the correction value Δ, in the storage device as a LUT. As a result, the data can be referred to when an image is picked up.

Further, when Δ has a minute value, for example, it is 0.1 mm or less, a program may be made to divert d2 set at a previous time as it is omitting a correction processing.

Although d2 becomes a value different from an initial value as the number of picked up images increases, a program may be made to permit an operator to return the different value to the initial value of d2 at any arbitrary timing by providing the observation apparatus with a reset button.

Figure 39:
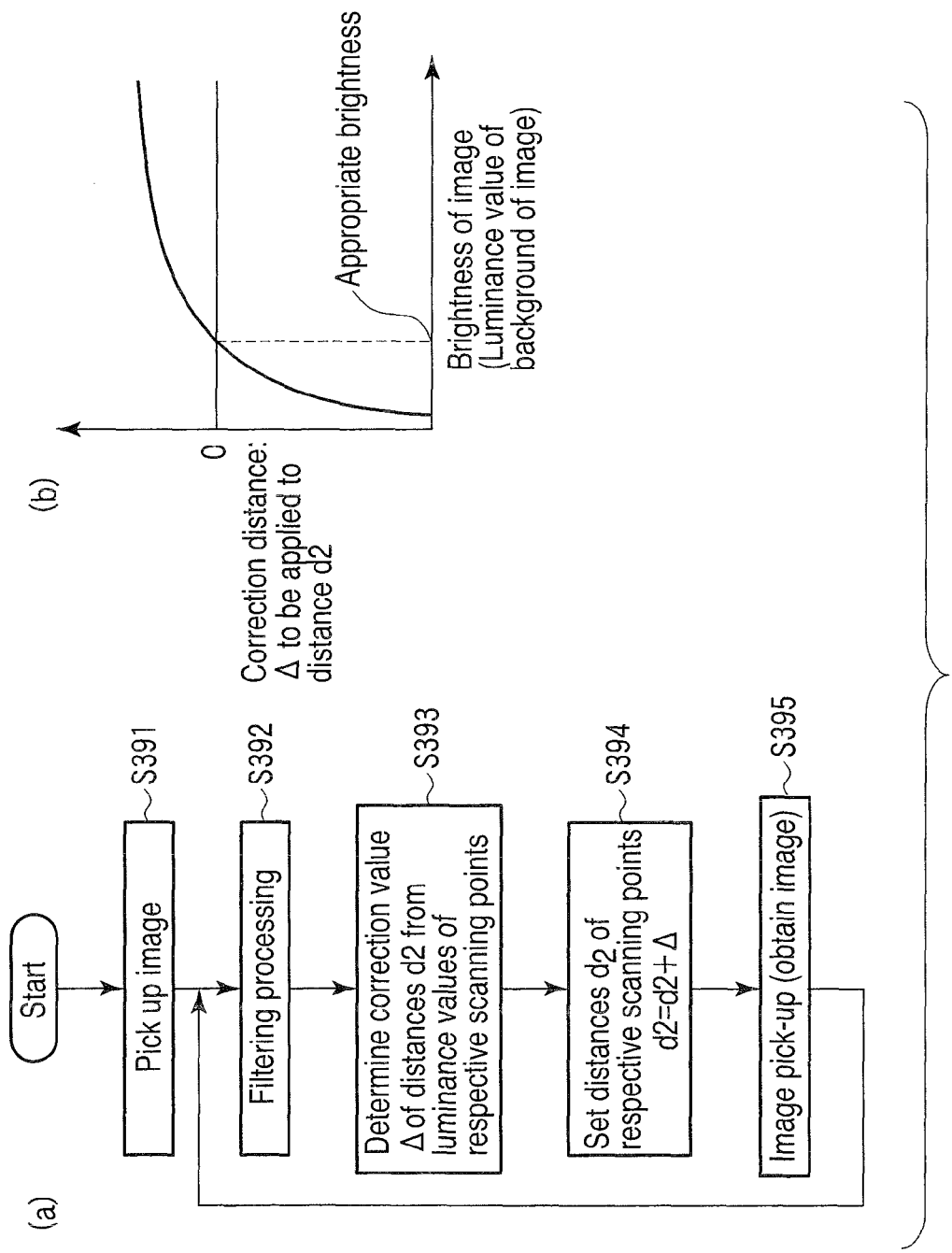
FIG. 39 is a flowchart showing an example of a correction method of performing a filtering processing.

A part (a) of FIG. 39 shows a flowchart of a correction method of performing the filtering processing each time an image is obtained when a moving image is picked up.

The control device starts to pick up an image by the observation apparatus in response to an instruction of an operator, and the process goes to S391.

At S391, an image is obtained by repeating S321 to S330 described in FIG. 32B in response to an instruction of the control device, and the process goes to S392.

At S392, the image processing device performs the filtering processing to an image in its entirety, and the process goes to S393.

At S393, the calculation device determines the correction value Δ of the distances d2 based on the luminance values of the respective scanning points in response to an instruction of the control device, and the process goes to S394.

At S394, the control device receives the correction value Δ from the calculation device, corrects the distances d2 by adding the correction value to the distances d2, and sets the corrected distances d2 at the respective scanning points, and the process goes to S395.

At S395, the control device obtains an image in the state where the control device instructs the inter-center distance adjustment optical system and the scanning mechanism to move and dispose the illumination optical system and the detection optical system so that the corrected distances d2 are kept, and the process goes to S392.

At S392, the control device determines whether or not an instruction for finishing the image pick-up is input to the input device or whether or not a preset condition is satisfied, and repeats an image pick-up loop of S392 to S395 according to a result of the determination, and when the control device admits the instruction for finishing the image pick-up or determines that preset condition is satisfied, the process exits the image pick-up loop and finishes the operation.

A part (b) of FIG. 39 shows a graph showing the relation between the correction distance Δ, which is applied to the distances d2, and a brightness of an image (that is, a luminance value of a background of an image). It is sufficient that the correction distance applied to the distances d2 so that an appropriate brightness can be obtained.

EXAMPLE 3

Figure 40:
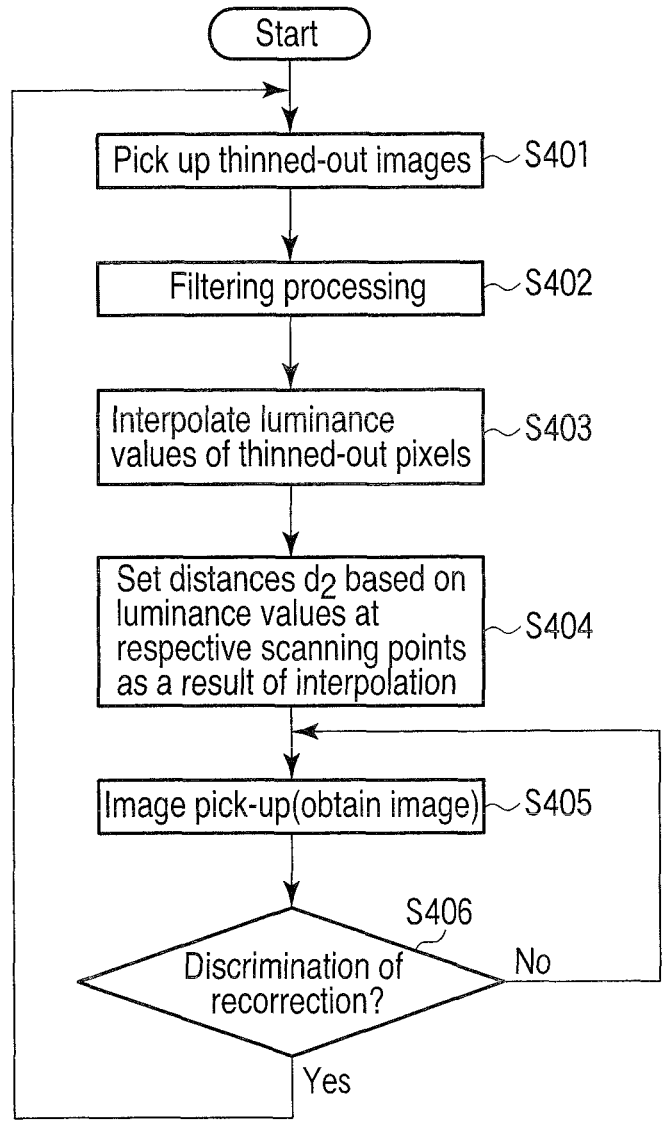
FIG. 40 is a flowchart showing an example of a correction method of performing a filtering processing.

An example 3 is another modification of the example 1 which can obtain the correction value in a short time by providing a configuration for thinning out the scanning points in an image pick-up for measuring a distribution of detection intensities of the background. The modification will be explained referring to FIG. 40.

The control device starts an image pick-up by the observation apparatus in response to an instruction of the operator, and the process goes to S401.

At S401, an image is obtained by repeating S321 to S330 described in FIG. 32B as to only specific scanning points according to a coordinate which is preset and stored in the storage device in response to an instruction of the control device, and the process goes to S382.

At S402, the image processing device performs the filtering processing to the image in its entirety in response to an instruction of the control device, and the process goes to S403.

At S403, the image processing device performs an interpolate processing to the image subjected to the filtering processing in response to an instruction of the control device, and the process goes to S404.

At S404, after the calculation device calculates the WD based on the luminance values of respective scanning points of the interpolated image and determines a correction value of the distances d2 of the respective scanning points according to the WD, the control device receives the correction value from the calculation device and sets the distances d2 at the respective scanning points based on the correction value, and the process goes to S405.

At S405, the control device obtains an image by repeating S321 to S330 described in FIG. 32B in the state where the control device instructs the inter-center distance adjustment optical system and the scanning mechanism to move and dispose the illumination optical system and the detection optical system so that the corrected distances d2 are kept, and the process goes to S406.

At S406, the control device determines whether or not the recorrection is necessary, and when the recorrection is not necessary, the process goes to S405, whereas when the recorrection is necessary, the process goes to S401 and repeats the respective steps.

At S405, the control device picks up an image in the state where the control device instructs the inter-center distance adjustment optical system and the scanning mechanism to move and dispose the illumination optical system and the detection optical system so that the corrected distances d2 are kept. Further, the control device causes the display device to display the obtained image. The process returns to S401.

It is sufficient to make a program for finishing a loop including S401 to S406 in such a manner that the control device determines an interruption of operation during the loop and/or a finish of a series of image pick-up steps according to an input by the operator and/or according to a preset and stored condition and the like and performs a control for the finish or the interruption.

An interpolation processing for a value of detection intensity distribution of the thinned-out scanning points may be performed by any of known methods such as a nearest neighbor method, a linear interpolation method, and the like.

An example of determination of recorrection may be performed likewise the determination described in the example 1. Further, the same condition and procedure as those of the example 1 may be used except execution of the thinning-out.

EXAMPLE 4

An example of a configuration of the control unit will be explained below referring to FIG. 41.

The configuration of FIG. 41 is an example in which the control device, the measurement device and the calculation device are included in one unit.

The control unit includes a storage device (not shown) for storing data such as a table, which corresponds respective information to each other, and the like, an adjusted coordinate data creation device connected to the storage device so as to deliver data between the adjusted coordinate data creation device and the storage device, a d2 correction processing device connected to the data creation device so as to deliver data between d2 correction processing device and the data creation device, an image data creation device connected to the data creation device and the d2 correction processing device so as to deliver data between the image data creation device and the data creation device and the d2 correction processing device, and an image processing device connected to the image data creation device so as to deliver data between the image processing device and the image data creation device, wherein the image processing device is connected to a display device, the adjusted coordinate data creation device and the image data creation device are connected to a timing control device and connected to a illumination side scanning mechanism and a detection side scanning mechanism via arbitrary D/A converters. Further, a detector is connected to the timing control device via an amplifier and a D/A converter, and the timing control device is connected to the image data creation device.

The data of a series of the scanning points, which is used in scanning, is stored in an original coordinate file. The original coordinate file is changed to adjusted coordinate data to which the correction of the distances d2 is added by the adjusted coordinate data creation device based on a detected intensity distribution.

A drive signal is transmitted to the illumination side scanning mechanism and the detection side scanning mechanism based on the adjusted data. When the scanning mechanisms are analog controlled, it is sufficient that scanning mechanisms are controlled via the converters (D/A) as shown in FIG. 41.

The timings of a scanning point control of illumination, a scanning point control of detection, and the exposure time of the detector must be properly controlled. For example, in order to detect an image simultaneously with a start of illumination, the scanning point controls of the illumination and the detection are performed at the same time, and, in order to obtain a predetermined exposure time, a signal from the detector is obtained after the exposure time has passed. After the signal is obtained, the operation shifts to a next control operation. Accordingly, in order to transmit a control signal to the scanning mechanisms and to obtain a detector signal from the detector, a configuration in which the timing control mechanism is interposed as shown in FIG. 41 may be used.

A detected intensity signal is combined with the coordinate data of the scanning points by the image data creation device and made to image data. Thereafter, various image processings are performed to adjust an image quality, and an image is displayed on the display device.

The image data is further sent to also a d2 correction processing device, and a background intensity distribution and a d2 correction value are calculated based on the data.

With method and observation apparatus of the fifth aspect, a better image can be obtained.

In the method according to the aspect, the observation apparatus can be made compact as well as the configuration of the apparatus can be simplified in comparison with a method of using other means such as a means of adjusting an SD distance according to an observation distance by separately mounting a distance measurement mechanism.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for obtaining information of an object in a turbid body, comprising:
    a light irradiation means for irradiating light onto a first light-irradiated region of a surface of the turbid body and an adjacent light-irradiated region of a surface of the turbid body, wherein the irradiating light has a different optical characteristic between the object and the turbid body;
    a detection means for detecting intensity of light backscattered from the turbid body, the detection carried out at a first detection region of the surface of the turbid body, and an adjacent detection region of the surface of the turbid body, which are spaced apart from the first light-irradiated region and adjacent light-irradiated region;
    an analysis means for analyzing position information of the object in the turbid body from the intensity of the backscattered light; and
    a scanning means for scanning the first light-irradiated region, adjacent light-irradiated region, and the first detection region and adjacent detection region on the surface of the turbid body at the same time, wherein a size of each of the first detection region and adjacent detection region is larger than a distance between a center of the first detection region and a center of the adjacent detection region, so that a portion of the first detection region overlaps a portion of the adjacent detection region, forming an overlap region.

2. The apparatus according to claim 1, further comprising an image construction means for creating tomographic images of the turbid body based on the intensity of the backscattered light.

3. The apparatus according to claim 2 further comprising a selection means for selecting the tomographic image of the object from the created tomographic images.

4. The apparatus according to claim 2, wherein the irradiating light includes a wavelength of a near infrared region having an absorption in hemoglobin.

5. The apparatus according to claim 1, wherein the optical characteristic is selected from a transmittance, a refraction index, a reflectance, a scattering coefficient, and an absorption coefficient.

6. A method of obtaining information of an object in a turbid body, the method comprising the steps of:
    irradiating a light onto both a first light-irradiated region of a surface of the turbid body and an adjacent light-irradiated region of a surface of the turbid body, wherein the irradiating light has a different optical characteristic between the object and the turbid body;

detecting intensity of light back-scattered from the turbid body, the detection being in both a first detection region of the surface of the turbid body and an adjacent detection region of the surface of the turbid body, which are spaced apart from the first light-irradiated region and adjacent light-irradiated region;

obtaining position information and depth information of the object in the turbid body from the intensity of the back-scattered light; and scanning both the first light-irradiated region, adjacent light-irradiated region, and scanning both the first detection region and adjacent detection region on the surface of the turbid body at the same time, wherein a size of each of the first detection region and adjacent detection region is larger than a distance between a center of the first detection region and a center of the adjacent detection region, so that a portion of the first detection region overlaps a portion of the adjacent detection region, forming an overlap region.

* * * * *